US008501498B2

(12) United States Patent
Yan et al.

(10) Patent No.: US 8,501,498 B2
(45) Date of Patent: Aug. 6, 2013

(54) MASS TAGS FOR QUANTITATIVE ANALYSES

(75) Inventors: Xiongwei Yan, Dublin, CA (US);
Pau-Miau Yuan, San Jose, CA (US);
Sylvia W. Yuen, San Mateo, CA (US);
Kuo-Liang Hsi, Fremont, CA (US); Joe Y. Lam, Castro Valley, CA (US);
Krishna G. Upadhya, Union City, CA (US); Subhakar Dey, North Billerica, MA (US); Darryl J. C. Pappin, Boxborough, MA (US); Sasi Pillai, Littleton, MA (US); Helena Huang, Boxborough, MA (US); Subhasish Purkayastha, Acton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 526 days.

(21) Appl. No.: 12/618,452

(22) Filed: Nov. 13, 2009

(65) Prior Publication Data

US 2010/0311175 A1    Dec. 9, 2010

Related U.S. Application Data

(63) Continuation of application No. 11/355,904, filed on Feb. 15, 2006, now abandoned, which is a continuation-in-part of application No. 11/179,060, filed on Jul. 11, 2005, now abandoned.

(60) Provisional application No. 60/679,183, filed on May 9, 2005, provisional application No. 60/587,138, filed on Jul. 12, 2004.

(51) Int. Cl.
*G01N 33/532* (2006.01)
*G01N 33/534* (2006.01)
*G01N 33/533* (2006.01)
*G01N 24/00* (2006.01)

(52) U.S. Cl.
USPC ............ 436/544; 436/545; 436/546; 436/173

(58) Field of Classification Search
None
See application file for complete search history.

(56) References Cited

U.S. PATENT DOCUMENTS

| | | | |
|---|---|---|---|
| 5,705,610 A | 1/1998 | Zuckermann et al. | |
| 5,800,992 A | 9/1998 | Foder et al. | |
| 6,027,890 A | 2/2000 | Ness et al. | |
| 6,270,976 B1 | 8/2001 | Schmidt et al. | |
| 6,287,780 B1 | 9/2001 | Schmidt et al. | |
| 6,383,754 B1 | 5/2002 | Kaufman et al. | |
| 6,475,807 B1 | 11/2002 | Geysen et al. | |
| 7,294,456 B2 | 11/2007 | Schmidt et al. | 435/4 |
| 2004/0110186 A1 | 6/2004 | Aebersold et al. | |
| 2004/0115821 A1 | 6/2004 | Beiswenger et al. | 436/86 |
| 2005/0048489 A1 | 3/2005 | Thompson et al. | 435/6 |
| 2005/0049406 A1 | 3/2005 | Lerchen et al. | |
| 2005/0148771 A1 | 7/2005 | Dey et al. | |
| 2005/0148773 A1 | 7/2005 | Pappin et al. | |
| 2007/0023628 A1 | 2/2007 | Hamon et al. | 250/282 |

FOREIGN PATENT DOCUMENTS

| | | |
|---|---|---|
| CA | 2466328 | 5/2003 |
| DE | 103 19 611 A1 | 11/2004 |
| DE | 103 22 077 A1 | 12/2004 |
| EP | 1 304 331 A | 4/2003 |
| EP | 1 475 632 A | 11/2004 |
| EP | 1 477 493 A | 11/2004 |
| WO | WO 97/08190 | 3/1997 |
| WO | WO 97/27331 A | 7/1997 |
| WO | WO 98/26095 | 6/1998 |
| WO | WO 98/26095 A | 6/1998 |
| WO | WO 98/31830 A | 7/1998 |
| WO | WO 00/11208 A | 3/2000 |
| WO | WO 00/20112 | 4/2000 |
| WO | WO 01/68664 A2 | 9/2001 |
| WO | WO 02/14867 A2 | 2/2002 |
| WO | WO 02/29003 A | 4/2002 |
| WO | WO 02/48717 A | 6/2002 |
| WO | WO 03/025576 A | 3/2003 |
| WO | WO 03/040093 A | 5/2003 |
| WO | WO 03/040287 A | 5/2003 |
| WO | WO 03/040288 A | 5/2003 |
| WO | WO 03/056299 A | 7/2003 |
| WO | WO 03/069328 A | 8/2003 |
| WO | WO 03/102220 A2 | 12/2003 |
| WO | WO 2004/007352 A2 | 1/2004 |
| WO | WO 2004/019000 A | 3/2004 |
| WO | WO 2004/070352 A | 8/2004 |
| WO | WO 2004/086050 A | 10/2004 |
| WO | WO 2005/012247 | 2/2005 |
| WO | WO 2005/054871 A2 | 6/2005 |
| WO | WO 2005/068446 A | 7/2005 |
| WO | WO 2006/017208 A1 | 2/2006 |

OTHER PUBLICATIONS

Bottari P et al: "Design and Synthesis of Visible Isotope-Coded Affinity Tags for The Absolute Quantification of Specific proteins in Complex Mixtures" Bioconjugate Chemistry, ACS, Washington, D.C., U.S. vol. 15, No. 2, Feb. 21, 2004, pp. 380-388.
Dunayevskiy, Yuriy M.: "Application of Capillary Electrophoresis—Electrospray ionization Mass Spectrometry in The Determination of Molecular Diversity"; PNAS 1996, Proc. Natl. Acad. Sci. USA 93—Boston, MA, Jan. 30, 1996, pp. 6152-6157.
Gygi S P et al: "Quantitative Analysis of Complex Protein Mixtures using Isotope-Coded Affinity Tags" Nature Biotechnology, nature Publishing Group, New York, NY, U.S. vol. 17, No. 10, Oct. 1, 1999, pp. 994-999.
PCT Partial International Search Report from PCT/US2007/003990 dated Oct. 15, 2007.
Song et al., Jan. 2005, "Automated 96-Well Solid Phase Extraction and Hydrophillic Interaction Liquid Chromatography—Tandem Mass Spectrometric Method for the Analysis of Cetirizine (ZYRTEC®) in Human Plasma—With Emphasis on Method Ruggedness," J. Chromatography B; Biomedical Sciences & Applications, 814(I)105-114.

(Continued)

*Primary Examiner* — Shafiqul Haq

(57) ABSTRACT

This invention pertains to methods, mixtures, kits and/or compositions for the determination of analytes by mass analysis using unique labeling reagents or sets of unique labeling reagents. The labeling reagents can be isomeric or isobaric and can be used to produce mixtures suitable for multiplex analysis of the labeled analytes.

18 Claims, 44 Drawing Sheets

OTHER PUBLICATIONS

Thompson et al., Jan. 2007, "Electrospray Ionisation—Cleavable Tandem Nucleic Acid Mass Tag—Peptide Nucleic Acid Conjugates: Synthesis and Applications to Quantitative Genomic Analysis Using Electrospray Ionisation—MS/MS," Nucleic Acids Res., 35(4):c28/1-c28/13.

Yao et al., Apr. 1999, "Simultaneous Quantitation of d7-Nefazodone, Nefazodone, d7-hydroxynefazodone, hydroxynefazodone, m-chlorophenylpiperazine and triazole-dione in Human Plasma by Liquid Chromatographic—Mass Spectrometry,", Biomed. Chromatogr., 14(2):106-112.

"Applied Biosystems iTRAQ™ Reagents Amino-Modifying Labeling Reagents for Multiplexed Relative and Absolute Protein Quantitation," Protocol, Applied Biosystems, Part No. 4350831, Rev. C, 2004.

Lu et al., "Absolute Quantification of Specific Proteins in Complex Mixtures Using Visible Isotope-Coded Affinity Tags", *Analytical Chemistry*, 46(14):4104-4111 (Jun. 11, 2004).

Bottari et al., "Design and Synthesis of Visible Isotope-Coded Affinity Tags for the Absolute Quantification of Specific Proteins in Complex Mixtures", *Bioconjugate Chemistry*, 15(2):380-388 (Feb. 21, 2004).

Thompson, A. et al., "Tandem Mass Tags: A Novel Quantification Strategy for Comparative Analysis of Complex Protein Mi8xtures by MS/MS", *Analytical Chemistry, American Chemical Society*, 75:1895-1904 (Mar. 1, 2003).

Shehipinov, M. S. et al., "Trityl Mass-Tags for Encoding in Combinatorial Oligonucleotide Synthesis", *Nucleic Acids Symposium Series*, 42:107-108 (1999).

Gygi et al., "Quantitative Analysis of Complex Protein Mixtures Using Isotope-Coded Affinity Tags", *Nature Biotechnology*, 17:994-999 (1999).

Roth, K.D.W. et al., "Charge Derivatization of Peptides for Analysis by Mass Spectrometry", *Mass Spectrometry Reviews*, 17(4):255-274 (1998).

Roussell, C. et al., "Generation of Mass Tags by the Inherent Electrochemistry to Electrospray for Protein Mass Spectrometry", *Journal of American Society for Mass Spectrometry*, 15(12):1767-1779 (Dec. 2004).

Communication pursuant to Article 94(3) EPC dated Jan. 13, 2011 in corresponding European Patent Application No. 07 750 802.6.

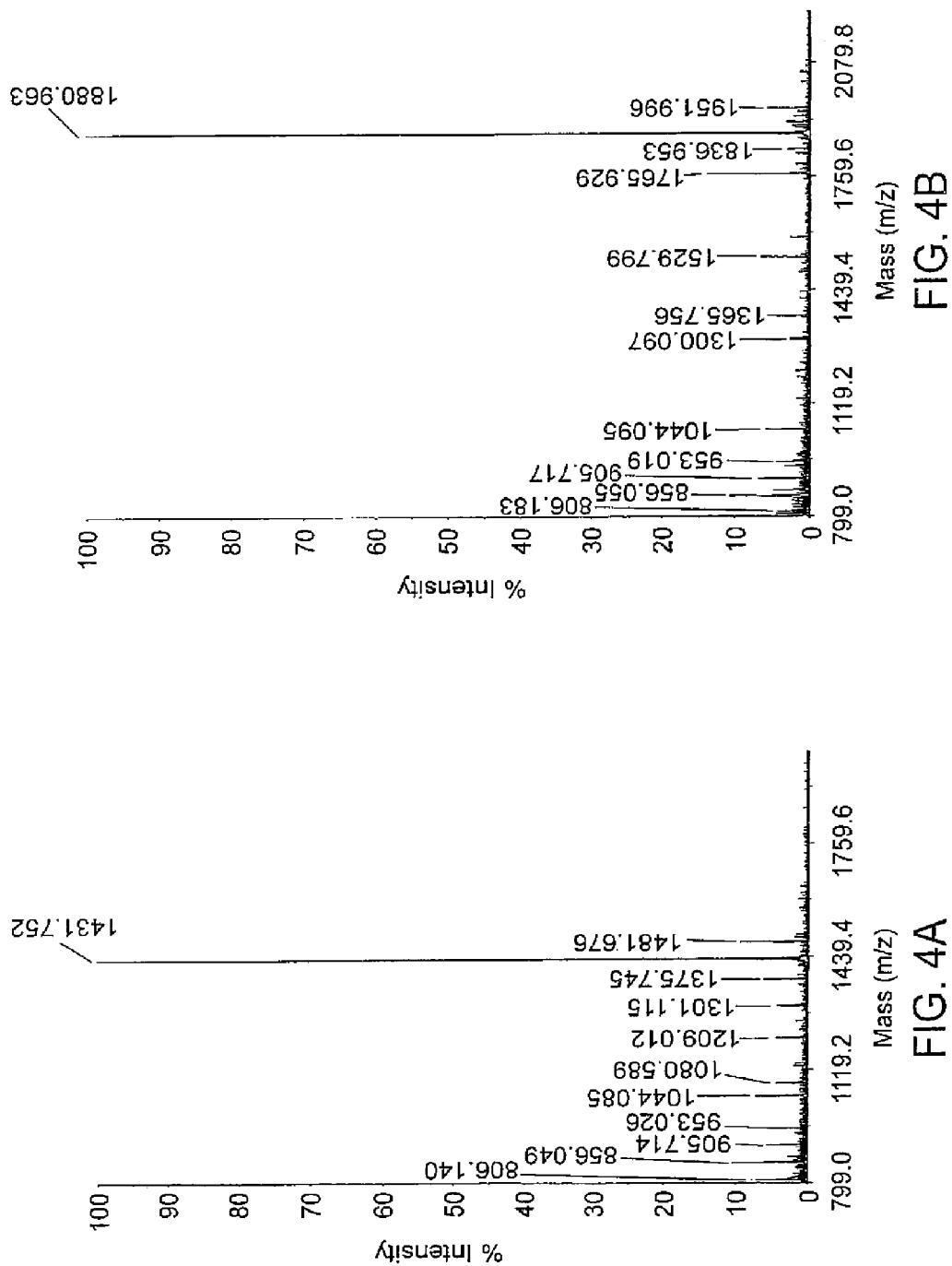

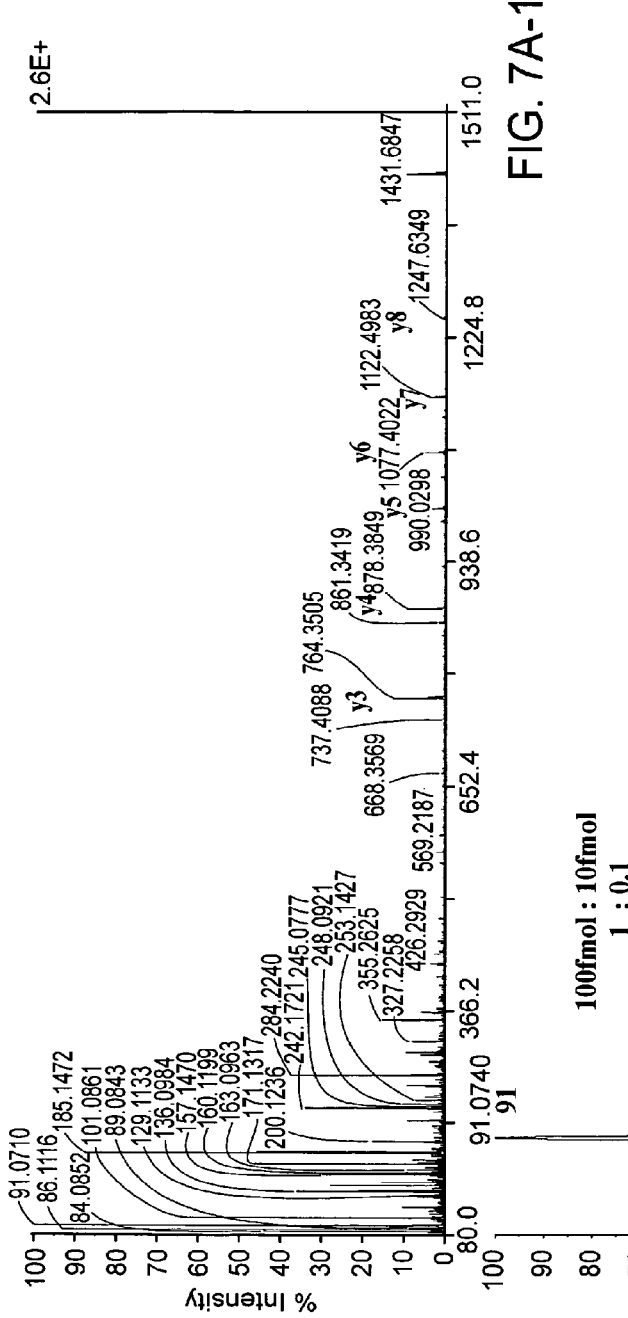
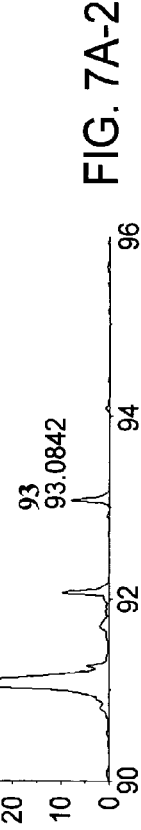
FIG. 7A-1
FIG. 7A-2

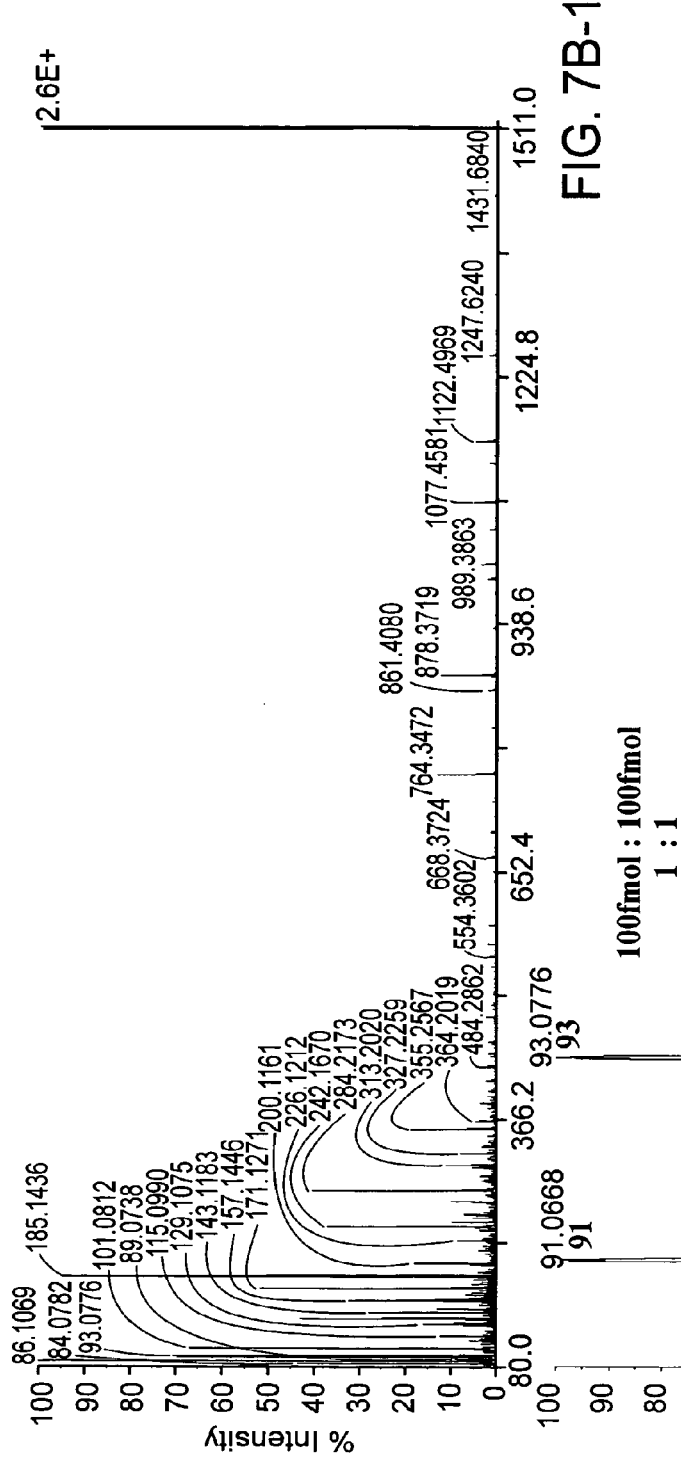

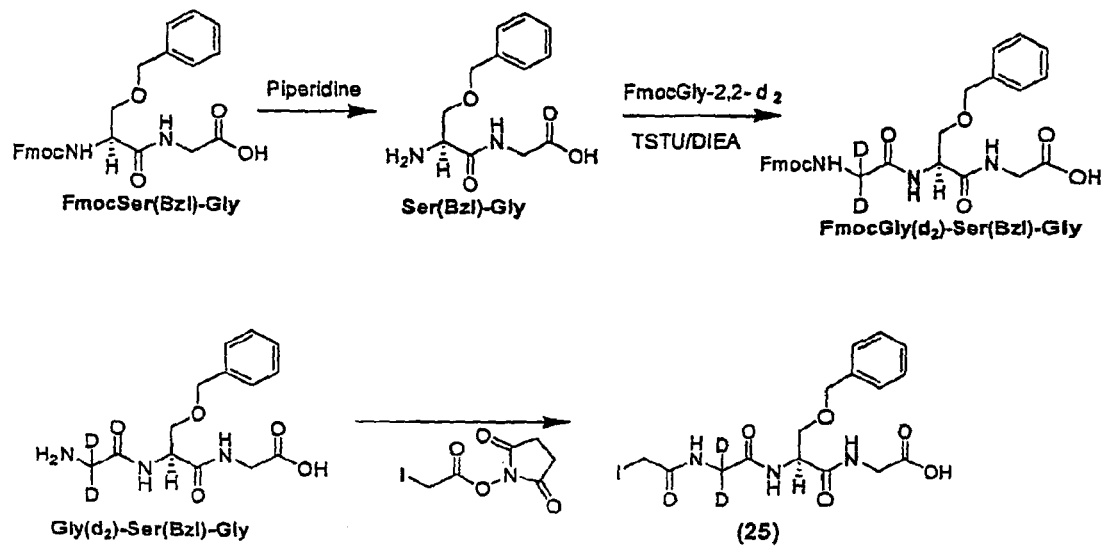
FIG 20
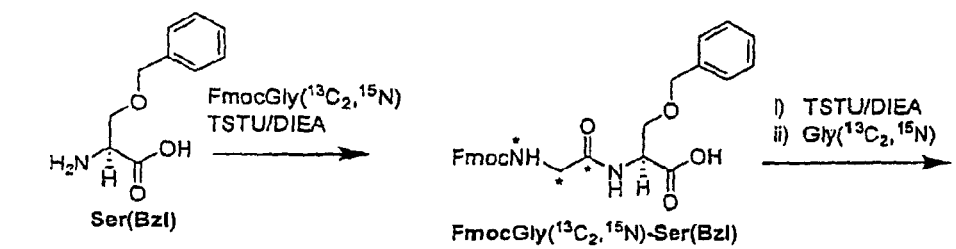
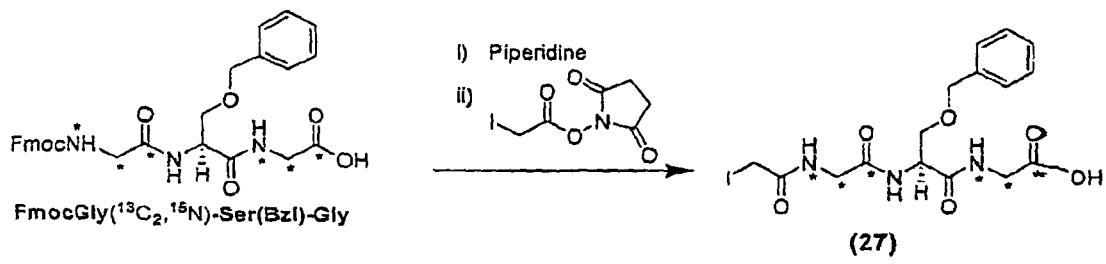
FIG 22

MASS TAGS FOR QUANTITATIVE ANALYSES

RELATED APPLICATIONS

This application is a continuation and claims the right of priority under 35 U.S.C. §120 to U.S. application Ser. No. 11/355,904, filed Feb. 15, 2006, which is a continuation-in-part of U.S. application Ser. No. 11/179,060, filed on Jul. 11, 2005, which claims the benefit of U.S. Application No. 60/679,183, filed on May 9, 2005, and U.S. Application No. 60/587,138, filed on Jul. 12, 2004. The entire teachings of the above applications are incorporated herein by reference.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

BRIEF DESCRIPTION OF THE DRAWINGS

The skilled artisan will understand that the drawings, described below, are for illustration purposes only. The drawings are not intended to limit the scope of the present teachings in any way.

FIG. 4A is a MS analysis of SEQ ID No.: 1, which was alkylated with mass tag (32), using a 4700 Proteomic Analyzer.

FIG. 4B is a MS analysis of SEQ ID No.: 3, which was alkylated with mass tag (32), using a 4700 Proteomic Analyzer.

FIGS. 7A-1 and 7A-2 are mass spectra in the MS/MS mode of the sample in FIG. 6A using a 4700 Proteomic Analyzer.

FIGS. 7B-1 and 7B-2 are mass spectra in the MS/MS mode of the sample in FIG. 6B using a 4700 Proteomic Analyzer.

FIGS. 7C-1 and 7C-2 are mass spectra in the MS/MS mode of the sample in FIG. 6C using a 4700 Proteomic Analyzer.

FIG. 20 illustrates the synthesis of Mass Tag (25).

FIG. 22 illustrates the synthesis of Mass Tag (27).

1. INTRODUCTION

Figure 1A:
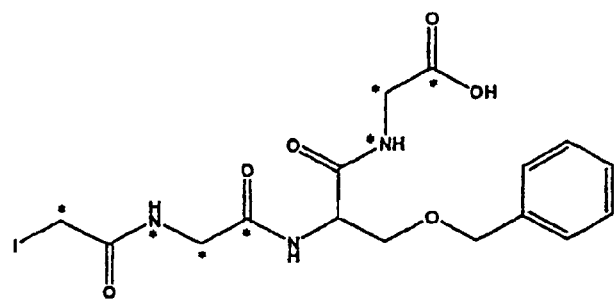
FIGS. 1A-1H show the structural formulae of a set of eight isobaric mass tags each of which have the same molecular weight but which will fragment to yield a signature ion having a different molecular weight when subjected to dissociative energy levels.
Figure 1B:
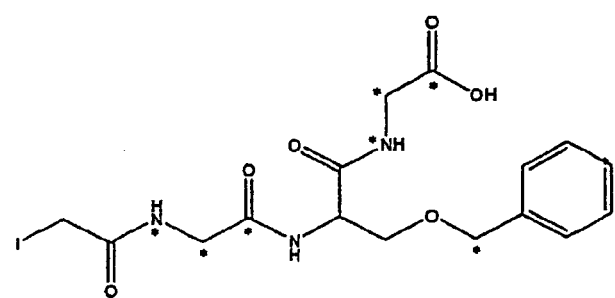

This invention pertains to methods, mixtures, kits and/or compositions for the determination of an analyte or analytes by mass analysis. An analyte can be any molecule of interest. Non-limiting examples of analytes include, but are not limited to, proteins, peptides, oligonucleotides, carbohydrates, lipids, steroids, amino acids and small molecules of less than 1500 daltons.

Labeling reagents and labeled analytes can be represented by a compound of the general formula:

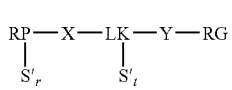

$I^w$ or a salt form and/or hydrate form thereof, wherein RG can be a reactive group that reacts with an analyte or the reaction product of the reactive group and the analyte. A labeled analyte therefore can have the general formula:

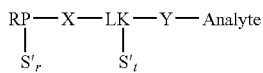

$I^\#$

The compound can be tethered to a solid support or moieties for linking it to a solid support via S'. The variables RG, RP, X, LK, S', r, t, and Y are described, in more detail below.

Sets of isomeric or isobaric labeling reagents can be used to label the analytes of two or more different samples wherein the labeling reagent can be different for each different sample and wherein the labeling reagent can comprise a unique reporter, "RP", that can be associated with the sample from which the labeled analyte originated. Hence, information, such as the presence and/or amount of the reporter, can be correlated with the presence and/or amount (often expressed as a concentration and/or quantity) of the analyte in a sample even from the analysis of a complex mixture of labeled analytes derived by mixing the reaction products obtained from the labeling of different samples. Analysis of such complex sample mixtures can be performed in a manner that allows for the determination of one or a plurality of analytes from the same or from multiple samples in a multiplex manner. Thus, the methods, mixtures, kits and/or compositions of this invention are particularly well suited for the multiplex analysis of complex sample mixtures. For example, they can be used in proteomic analysis and/or genomic analysis as well as for correlation studies related to genomic and/or proteomic analysis.

2. DEFINITIONS

For the purposes of interpreting of this specification, the following definitions will apply and whenever appropriate, terms used in the singular will also include the plural and vice versa. In the event that any definition set forth below conflicts with any other document, including any incorporated herein by reference for all purposes, the definition set forth below shall control:

As used herein, "analyte" refers to any molecule of interest that may be determined. Non-limiting examples of analytes can include, but are not limited to, proteins, peptides, nucleotides, oligonucleotides (both DNA or RNA), carbohydrates, lipids, steroids, amino acids and/or other small molecules with a molecular weight of less than 1500 daltons. The source of the analyte, or the sample comprising the analyte, is not a limitation as it can come from any source. The analyte or analytes can be natural or synthetic. Non-limiting examples of sources for the analyte, or the sample comprising the analyte, include but are not limited to cells or tissues, or cultures (or subcultures) thereof. Non-limiting examples of analyte sources include, but are not limited to, crude or processed cell lysates (including whole cell lysates), body fluids, tissue extracts or cell extracts. Still other non-limiting examples of sources for the analyte include but are not limited to fractions from a separations process such as a chromatographic separation or an electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more analytes that are peptides formed by treatment of the total protein component of a crude cell lysate with a proteolytic enzyme to thereby digest precursor protein or proteins. For the avoidance of doubt, the term analyte can include the original analyte and compounds derived therefrom, unless from the context a clearly contrary meaning is intended. For example, in some embodiments, the term analyte can apply to a protein as well as to the peptides derived therefrom by digestion of said protein.

As used herein, "fragmentation" refers to the breaking of a covalent bond.

As used herein, "fragment" refers to a product of fragmentation (noun) or the operation of causing fragmentation (verb).

It is well accepted that the mass of an atom or molecule can be approximated, often to the nearest whole number atomic mass unit or the nearest tenth or hundredth of an atomic mass unit. As used herein, "gross mass" refers to the absolute mass as well as to the approximate mass within a range where the use of isotopes of different atom types are so close in mass that they are the functional equivalent for the purpose of balancing the mass of the reporter and/or linker moieties (so that the gross mass of the reporter/linker combination is the same within a set or kit of isobaric or isomeric labeling reagents) whether or not the very small difference in mass of the different isotopes types used can be detected.

For example, the common isotopes of oxygen have a gross mass of 16.0 (actual mass 15.9949) and 18.0 (actual mass 17.9992), the common isotopes of carbon have a gross mass of 12.0 (actual mass 12.00000) and 13.0 (actual mass 13.00336) and the common isotopes of nitrogen have a gross mass of 14.0 (actual mass 14.0031) and 15.0 (actual mass 15.0001). Whilst these values are approximate, one of skill in the art will appreciate that if one uses the $^{18}O$ isotope in one reporter of a set, the additional 2 mass units (over the isotope of oxygen having a gross mass of 16.0) can, for example, be compensated for in a different reporter of the set comprising $^{16}O$ by incorporating, elsewhere in the reporter, two carbon $^{13}C$ atoms, instead of two $^{12}C$ atoms, two $^{15}N$ atoms, instead of two $^{14}N$ atoms or even one $^{13}C$ atom and one $^{15}N$ atom, instead of a $^{12}C$ and a $^{14}N$, to compensate for the $^{18}O$. In this way the two different reporters of the set are the functional mass equivalent (i.e. have the same gross mass) since the very small actual differences in mass between the use of two $^{13}C$ atoms (instead of two $^{12}C$ atoms), two $^{15}N$ atoms (instead of two $^{14}N$ atoms), one $^{13}C$ and one $^{15}N$ (instead of a $^{12}C$ and $^{14}N$) or one $^{18}O$ atom (instead of one $^{16}O$ atom), to thereby achieve an increase in mass of two Daltons, in all of the labels of the set or kit, is not an impediment to the nature of the analysis.

Figure 1C:
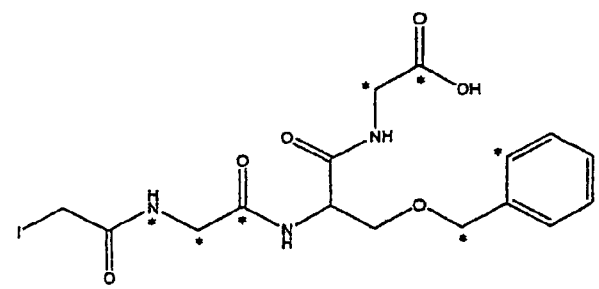
Figure 1D:
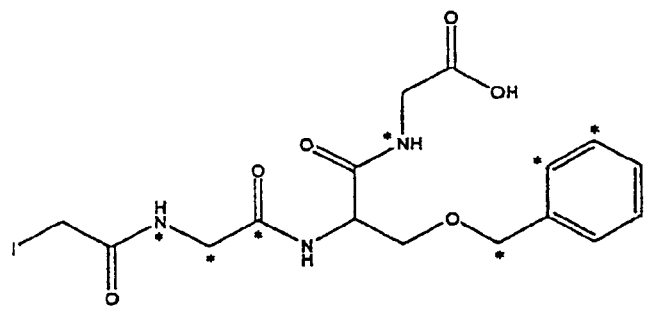
Figure 1E:
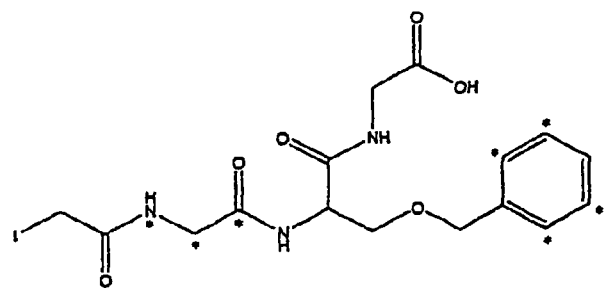
Figure 1F:
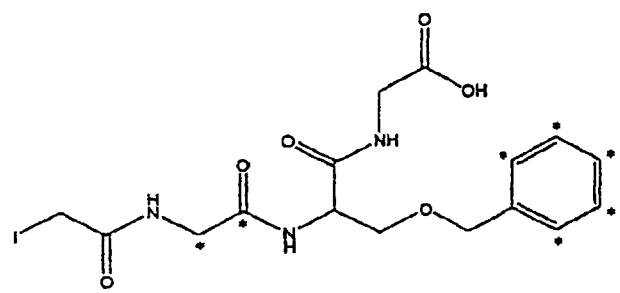
Figure 1G:
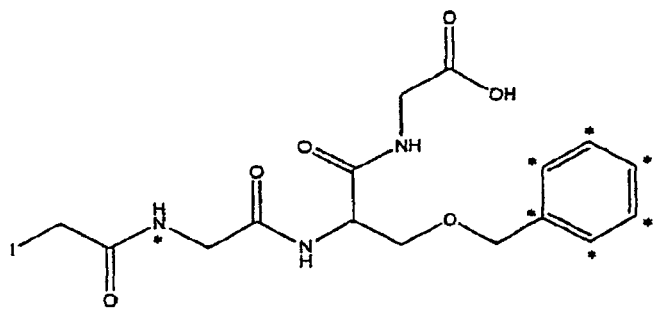
Figure 1H:
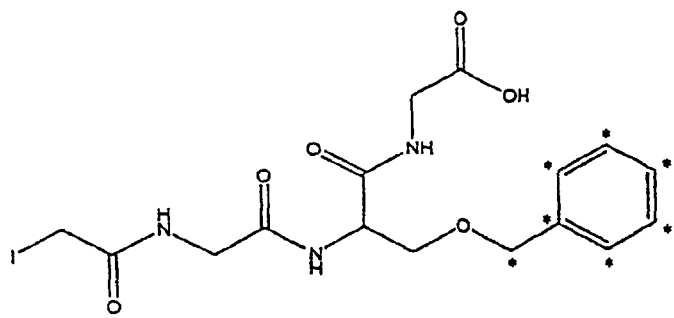

This can be illustrated with reference to FIGS. 1A-1H. In FIG. 1A, the reporter/linker combination (FIG. 1A, not including the reactive iodo group; chemical formula: $C_{11}{}^{13}C_5H_{20}N^{15}N_2O_6$) has two $^{15}N$ atoms and five $^{13}C$ atom and a total theoretical mass of 357.2213. By comparison, the reporter/linker isobar shown in FIG. 1C (chemical formula $C_{10}{}^{13}C_6H_{20}N_2{}^{15}NO_6$) has one $^{15}N$ atom and six $^{13}C$ atom and a total theoretical mass of 357.2279. The compounds in FIGS. 1A and C are isobars that are structurally and chemically indistinguishable, except for heavy atom isotope content, although there is a slight absolute mass difference (mass 357.2213 vs. mass 357.2279, respectively). However, the gross mass of the compounds in FIGS. 1A and 1C is 357.2 for the purposes of this invention since this is not an impediment to the analysis whether or not the mass spectrometer is sensitive enough to measure the small difference between the absolute mass of the isobars in FIGS. 1A and 1C.

From FIGS. 1A-1H, it is clear that the distribution of the same heavy atom isotopes within a structure is not the only consideration for the creation of sets of isomeric and/or isobaric labeling reagents. It is possible to mix heavy atom isotope types to achieve isomers or isobars of a desired gross mass. In this way, both the selection (combination) of heavy atom isotopes as well as their distribution is available for consideration in the production of the isomeric and/or isobaric labeling reagents useful for embodiments of this invention.

As used herein, "isotopically enriched" refers to a compound (e.g. labeling reagent) that has been enriched synthetically with one or more heavy atom isotopes (e.g. stable isotopes such as deuterium, $^{13}C$, $^{15}N$, $^{18}O$, $^{37}Cl$ or $^{81}Br$). Because isotopic enrichment is not 100% effective, there can be impurities of the compound that are of lesser states of enrichment and these will have a lower mass. Likewise, because of over-enrichment (undesired enrichment) and because of natural isotopic abundance, there can be impurities of greater mass. In some embodiments, each incorporated heavy atom isotope can be present in at least 80 percent isotopic purity. In some embodiments, each incorporated heavy atom isotope can be present in at least 93 percent isotopic purity. In some embodiments, each incorporated heavy atom isotope can be present in at least 96 percent isotopic purity.

As used herein, compounds that are "isotopologues" have the same chemical composition but differ in isotopic composition (number of isotopic substitutions), e.g., the methane isotopologues $CH_4$, $CH_3D$, and $CH_2D_2$.

As used herein, compounds that are "isobaric isotopologues" are those that have the same chemical composition and differ in isotopic composition but have the same gross mass as measured by a mass spectrometer (e.g., for the methane isobaric isotopologues $^{14}CH_4$, $^{13}CH_3D$, and $CH_2D_2$, each has a gross mass of 18 atomic mass units).

Some embodiments are an isotopically enriched compound that can have at least two atoms that are isotopically enriched. In various embodiments, the isotopically enriched compound can have 1, 2, 3, 4, 5, 6, 7, 8, 9, 10, 11, 12, 13, 14, 15, 16, 17, 18, 19, 20, 21, 22, 23, 24, 25, or more atoms that are isotopically enriched. The chemical structure of the compound can be represented by any of the preceding formulas wherein the variables are as defined generally and in classes and subclasses described herein.

As used herein, "labeling reagent" refers to a moiety suitable to mark an analyte for determination. The term label is synonymous with the terms tag and mark and other equivalent terms and phrases. For example, a labeled analyte can also be referred to as a tagged analyte or a marked analyte. Accordingly the terms "label", "tag", "mark" and derivatives of these terms, are interchangeable and refer to a moiety suitable to mark, or that has marked, an analyte for determination.

As used herein a "mass tag," as used herein, refers to a labeling reagent that can be used to label or mark an analyte by adding a group having a particular gross mass to the analyte. A set of mass tags includes two or more mass tags, each of which adds a group having the same mass to an analyte that is labeled. However, each of the mass tags in the set of mass tags will fragment when dissociative energy is applied to a signature ion having a different mass from the signature ions of other mass tags in the set. Mass tag and labeling reagent are equivalent terms for the purposes of this description. Thus, a set of mass tags is the equivalent of a set of labeling reagents.

As used herein, "support", "solid support" or "solid carrier" refers to any solid phase material upon which a labeling reagent or analyte can be immobilized. Immobilization can, for example, be used to label analytes or be used to prepare a labeling reagent, whether or not the labeling occurs on the support. Solid support encompasses terms such as "resin", "synthesis support", "solid phase", "surface" "membrane" and/or "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection methods and/or instruments.

As used herein, a "library" is a plurality of different compounds (e.g., labeling reagents, mass tags, labeled analytes, or the like), typically 5, 10, 25, 50, 100, 250 or more different compounds. A library is typically configured for ease of sequential, random, and/or parallel access to one, a plurality, and/or all of the different compounds therein. For example, the plurality of different compounds a library can be in the same flask, or can be immobilized on one or more solid supports, or the like. Typically, a library can have at least two different compounds immobilized at different locations, e.g., on physically distinct supports (e.g., beads, spheres, particles, granules, or the like) or at addressable locations on the same support (e.g., as a random or regular array on a solid support). The different compounds in a library can be contacted with other compounds (e.g., one or more analytes can be reacted with a library of labeling reagents) or can be analyzed (e.g., a library of labeled analytes can be analyzed), or the like. For example, in some embodiments, a library can comprise a plurality of different labeling reagents, wherein each different labeling reagent can be immobilized at a known address in a regular array on a solid support. The library can be used to label a plurality of separate analyte samples with particular labeling reagents by separately spotting (contacting) the analyte samples to each different immobilized labeling reagent, thereby producing a plurality of labeled analytes. In another example, a library of labeling reagents can have a different labeling reagent immobilized on each of a plurality of solid particles. The library can be employed by contacting each solid particle with a different analyte sample, whereby a plurality of labeled analytes are immobilized to the solid particles.

As used herein, an "affinity ligand" refers to a molecule that is a member of a molecular recognition system.

As used herein, a "molecular recognition system" refers to a system of at least two molecules or complexes which have a high capacity of molecular recognition for each other and a high capacity to specifically bind to each other. In a some embodiments, the binding is specific, and the affinity ligand is part of a binding pair.

Unless specified as a covalent bond, the term "bind" or "bound" includes both covalent and non-covalent associations.

"Specific binding," as used herein, refers to when an affinity ligand of a molecular recognition system binds one or more other molecule or complex, with specificity sufficient to differentiate between the molecule or complex and other components or contaminants of a sample. Molecular recognition systems for use in the invention are conventional and are not described here in detail. Techniques for preparing and utilizing such systems are well known in the art and are exemplified in the publication of Tijssen, P., "Laboratory Technique's in Biochemistry and Molecular Biology Practice and Theories of Enzyme Immunoassays" (1988), eds. Burdon and Knippenberg, New York:Elsevier, the entire teachings of which are incorporated herein. Examples of molecular recognition systems include, for example, an antigen/antibody, an antigen/antibody fragment, an avidin/biotin, a streptavidin/biotin, a protein $A/I_g$ or a lectin/carbohydrate.

As used herein, "natural isotopic abundance" refers to the level (or distribution) of one or more isotopes found in a compound based upon the natural prevalence of an isotope or isotopes in nature. For example, a natural compound obtained from living plant matter can typically contain about 1.08% $^{13}C$ relative to $^{12}C$ As used herein, "amino acid" refers to a group represented by —NH—CHR#—C(O)—, wherein R# is hydrogen, deuterium, an aliphatic group, a substituted aliphatic group, an aromatic group or a substituted aromatic group. A "naturally-occurring amino acid" is found in nature. Examples include glycine, alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine. In some embodiments, R# can be a side-chain of a naturally-occurring amino acid. Examples of naturally occurring amino acid side-chains include methyl (alanine), isopropyl (valine), sec-butyl (isoleucine), —$CH_2CH(—CH_3)_2$ (leucine), benzyl (phenylalanine), p-hydroxybenzyl (tyrosine), —$CH_2$—OH (serine), —$CHOHCH_3$ (threonine), —$CH_2$-3-indoyl (tryptophan), —$CH_2COOH$ (aspartic acid), —$CH_2CH_2COOH$ (glutamic acid), —$CH_2C(O)NH_2$ (asparagine), —$CH_2CH_2C(O)NH_2$ (glutamine), —$CH_2SH$, (cysteine), —$CH_2CH_2SCH_3$ (methionine), —$(CH_2)_4NH_2$ (lysine), —$(CH_2)_3NH_2$ (ornithine), —$\{(CH_2)_4NHC(=NH)NH_2$ (arginine) and —$CH_2$-3-imidazoyl (histidine).

The side-chains of other naturally-occurring amino acids comprise a heteroatom-containing functional group, e.g., an alcohol (serine, tyrosine, hydroxyproline and threonine), an amine (lysine, ornithine, histidine and arginine), a thiol (cysteine) or a carboxylic acid (aspartic acid and glutamic acid). When the heteroatom-containing functional group is modified to include a protecting group, the side-chain is referred to as the "protected side-chain" of an amino acid. In some embodiments, $R^w$ is a protected side-chain of an amino acid.

The selection of a suitable protecting group depends upon the functional group being protected, the conditions to which the protecting group is being exposed and to other functional groups that may be present in the molecule. Suitable protecting groups for the functional groups discussed above are well known in the art and many examples are described in Greene and Wuts, "Protective Groups in Organic Synthesis", John Wiley & Sons (1991). The skilled artisan can select, using no more than routine experimentation, suitable protecting groups for use in the disclosed synthesis, including protecting groups other than those described below, as well as conditions for applying and removing the protecting groups.

As used herein, a "peptide" refers to a polymer comprising two or more amino acids linked together by amide (peptide) bonds.

As used herein, the terms "optionally substituted" and "substituted or unsubstituted" are equivalent.

As used herein, a halo group refers to —F, —Cl, —Br, or —I.

As used herein, the term "alkyl," refers to a straight chained or branched $C_1$-$C_{20}$ hydrocarbon or a cyclic $C_3$-$C_{20}$ hydrocarbon that is completely saturated. When used herein the term "alkyl" refers to a group that may be substituted or unsubstituted. In some embodiments, alkyl can be a straight chained or branched $C_1$-$C_6$ hydrocarbon or a cyclic $C_3$-$C_6$ hydrocarbon that is completely saturated.

As used herein, the term "alkylene" refers to a straight or branched alkyl chain or a cyclic alkyl that is optionally substituted and that has at least two points of attachment to at least two moieties (e.g., {—$CH_2$—, methylene}, —{$CH_2CH_2$—, ethylene},

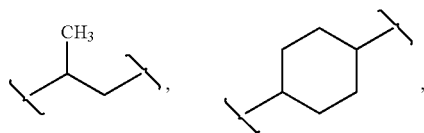

etc., wherein the brackets indicate the points of attachment). When used herein the term "alkylene" refers to a group that may be substituted or unsubstituted.

As used herein, the term "alkenyl" refers to straight chained or branched $C_2$-$C_{20}$ hydrocarbons or cyclic $C_3$-$C_{20}$ hydrocarbons that have one or more double bonds. When used herein the term "alkenyl" refers to a group that can be substituted or unsubstituted. In some embodiments, alkenyl groups can be straight chained or branched $C_2$-$C_6$ hydrocarbon or cyclic $C_3$-$C_6$ hydrocarbons that have one or more double bonds.

As used herein, the term "alkenylene" refers to an alkenyl group that has two points of attachment to at least two moieties. When used herein the term "alkenylene" refers to a group that may be substituted or unsubstituted.

As used herein, the term "alkynyl" refers to straight chained or branched $C_2$-$C_{20}$ hydrocarbons or cyclic $C_3$-$C_{20}$ hydrocarbons that have one or more triple bonds. When used herein the term "alkynyl" refers to a group that can be substituted or unsubstituted. In some embodiments, alkynyl groups can be straight chained or branched $C_2$-$C_6$ hydrocarbon or cyclic $C_3$-$C_6$ hydrocarbons that have one or more triple bonds.

As used herein, the term "alkynylene" refers to an alkynyl group that has two points of attachment to at least two moieties. When used herein the term "alkynylene" refers to a group that may be substituted or unsubstituted.

As used herein, the term "aliphatic" refers to any of the straight, branched, or cyclic alkyl, alkenyl, and alkynyl moieties as defined above. When used herein the term "aliphatic" refers to a group that may be substituted or unsubstituted.

As used herein, the term "heteroalkyl" refers to an alkyl group in which one or more methylene groups in the alkyl chain is replaced by a heteroatom such as —O—, —S—, and —NR—. R can be a hydrogen, deuterium, alkyl, aryl, arylalkyl, alkenyl, alkynyl, heteroaryl, heteroarylalkyl, or heterocycloalkyl. When used herein, the term "heteroalkyl" refers to a group that can be substituted or unsubstituted.

As used herein, the term "heteroalkylene" refers to a group having the formula-{(alkylene-X')$_r$-alkylene}-, wherein X', for each occurrence, is —O—, —NR—, or —S—; and r is an integer from 1 to 10. When used herein the term "heteroalkylene" refers to a group that can be substituted or unsubstituted. In some embodiments, r can be an integer from 1 to 5.

As used herein, the term "azaalkylene" refers to a heteroalkylene wherein at least one X' is —NR—. When used herein, the term "azaalkylene" refers to a group that can be substituted or unsubstituted.

The term "aryl," as used herein, either alone or as part of another moiety (e.g., arylalkyl, etc.), refers to carbocyclic aromatic groups such as phenyl. Aryl groups also include fused polycyclic aromatic ring systems in which a carbocyclic aromatic ring is fused to another carbocyclic aromatic ring (e.g., 1-naphthyl, 2-naphthyl, 1-anthracyl, 2-anthracyl, etc.) or in which a carbocylic aromatic ring is fused to one or more carbocyclic non-aromatic rings (e.g., tetrahydronaphthylene, indan, etc.). As used herein, the term "aryl" refers to a group that may be substituted or unsubstituted.

As used herein, the term "arylene" refers to an aryl group that has at least two points of attachment to at least two moieties (e.g., phenylene, etc.). The point of attachment of an arylene fused to a carbocyclic, non-aromatic ring may be on either the aromatic, non-aromatic ring. As used herein, the term "arylene" refers to a group that may be substituted or unsubstituted.

As used herein, the term "arylalkyl" refers to an aryl group that is attached to another moiety via an alkylene linker. As used herein, the term "arylalkyl" refers to a group that may be substituted or unsubstituted.

As used herein, the term "arylalkylene" refers to an arylalkyl group that has at least two points of attachment to at least two moieties. The second point of attachment can be on either the aromatic ring or the alkylene. As used herein, the term "arylalkylene" refers to a group that may be substituted or unsubstituted. When an arylalkylene is substituted, the substituents may be on either or both of the aromatic ring or the alkylene portion of the arylalkylene.

As used herein, the term "heteroaryl," refers to an aromatic heterocycle which comprises 1, 2, 3 or 4 heteroatoms independently selected from nitrogen, sulfur and oxygen. As used herein, the term "heteroaryl" refers to a group that may be substituted or unsubstituted. A heteroaryl may be fused to one or two rings, such as a cycloalkyl, a heterocycloalkyl, an aryl, or a heteroaryl. The point of attachment of a heteroaryl to a molecule may be on the heteroaryl, cycloalkyl, heterocycloalkyl or aryl ring, and the heteroaryl group may be attached through carbon or a heteroatom. Heteroaryl groups may be substituted or unsubstituted. Examples of heteroaryl groups include imidazolyl, furyl, pyrrolyl, thienyl, oxazolyl, thiazolyl, isoxazolyl, isothiazolyl, thiadiazolyl, oxadiazolyl, pyridinyl, pyrimidyl, pyrazinyl, pyridazinyl, quinolyl, isoquinolinyl, indazolyl, benzoxazolyl, benzisooxazolyl, benzofuryl, benzothiazolyl, indolizinyl, imidazopyridinyl, pyrazolyl, triazolyl, isothiazolyl, oxazolyl, tetrazolyl, benzimidazolyl, benzothiazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl or benzo(b)thienyl, each of which is optionally substituted.

As used herein, the term "heteroarylene" refers to a heteroaryl group that has at least two points of attachment to at least two moieties. As used herein, the term "heteroarylene" refers to a group that may be substituted or unsubstituted.

As used herein, the term "azaarylene" refers to a heteroarylene in which one of the heteroatoms is a nitrogen. Azaarylenes may also comprise 1, 2, or 3 non-nitrogen heteroatoms such as S and O. As used herein, the term "azaarylene" refers to a group that may be substituted or unsubstituted.

As used herein, the term "heteroarylalkyl" refers to a heteroaryl group that is attached to another moiety via an alkylene linker. As used herein, the term "heteroarylalkyl" refers to a group that may be substituted or unsubstituted.

As used herein, the term "heteroarylalkylene" refers to a heteroarylalkyl group that has at least two points of attachment to at least two moieties. The second points of attachment can be on either the hetroaromatic ring or the alkylene. As used herein, the term "heteroarylalkylene" refers to a group that may be substituted or unsubstituted. When a heteroarylalkylene is substituted, the substituents may be on either or both of the heteroaromatic ring or the alkylene portion of the heteroarylalkylene.

As used herein, the term "heterocycloalkyl" refers to a non-aromatic ring which comprise one or more oxygen, nitrogen or sulfur (e.g., morpholine, piperidine, piperazine, pyrrolidine, and thiomorpholine). As used herein, the term "heterocycloalkyl" refers to a group that may be substituted or unsubstituted.

As used herein, the term "heterocycloalkylene" refers to a heterocycloalkyl that has at least two points of attachment to at least two moieties. As used herein, the term "heterocycloalkylene" refers to a group that may be substituted or unsubstituted.

As used herein, the term "azacycloalkylene" refers to a heterocycloalkylene in which one heteroatom is a nitrogen. Azacycloalkylenes may also comprise 1, 2, or 3 non-nitrogen heteroatoms such as S and O. As used herein, the term "azacycloalkylene" refers to a group that may be substituted or unsubstituted.

Suitable substituents for an alkyl, alkylene, alkenylene, alkynylene, heteroalkyl, heteroalkylene, azaalkylene, heterocycloalkyl, heterocycloalkylene, azacycloalkylene, aryl, arylene, arylalkyl, arylalkylene, heteroaryl, heteroarylene, azaarylene, heteroarylalkyl, and heteroarylalkylene groups include any substituent that is stable under the reaction conditions used to label analytes with the mass tags of the invention. Examples of substituents for an alkyl, an alkylene, alkenylene, alkynylene, heteroalkyl, heteroalkylene, azaalkylene, heterocycloalkyl, heterocycloalkylene, azacycloalkylene, aryl, arylene, arylalkyl, arylalkylene, heteroaryl, heteroarylene, azaarylene, heteroarylalkyl, and heteroarylalkylene include deuterium, an aryl (e.g., phenyl) group, an arylalkyl (e.g., benzyl) group, a nitro group, a cyano group, a halo (e.g., fluorine, chlorine, bromine and iodine) group, a alkyl (e.g., methyl, ethyl, isopropyl, cyclohexyl, etc.) group, a haloalkyl (e.g., trifluoromethyl) group, an alkoxy (e.g., methoxy, ethoxy, etc.) group, a hydroxy group, —$NR^wR^w$, —$NR^wC(O)R^o$, —$C(O)NR^wR^w$, —$C(O)R^w$, —$C(O)OR^w$, wherein each $R^w$ is independently, hydrogen, deuterium, an alkyl, an aryl, or an arylalkyl; and $R^o$ for each occurrence is, independently, an alkyl, an aryl, or an arylalkyl. In addition, substituents for an aryl, an arylene, a heteroaryl or a heteroarylene can be a group that includes an affinity ligand or a group that includes a solid support.

In addition, alkyl, alkylene, heteroalkyl, heteroalkylene, azaalkylene, a heterocycloalkyl, a heterocycloalkylene azacycloalkylene groups, and any saturated portion of a alkenyl, alkenylene, alkynyl, alkynylene, arylalkyl, arylalkylene, heteroarylalkyl, and heteroarylalkylene groups, may also be substituted with =O, =S, =N—$R^w$.

When a heterocycloalkyl, heterocycloalkylene, heteroaryl, heteroarylene, heteroarylalkyl, or heteroarylalkylene group contains a nitrogen atom, it may be substituted or unsubstituted. When a nitrogen atom in the aromatic ring of a heteroaryl group has a substituent the nitrogen may be a quaternary nitrogen.

Suitable substituents for an aliphatic group, non-aromatic heterocyclic group, benzylic group, an aryl group ring carbon and a heteroaryl ring carbon are those which do not substantially interfere with the labeling reaction of the reactive group of the disclosed compounds. Examples of suitable substituents can include deuterium, —OH, halogen (—F, —Cl, —Br, —I), —CN, —NO$_2$, —$OR^a$, —$C(O)R^a$, —$OC(O)R^a$, —$C(O)OR^a$, —$SR^a$, —$C(S)R^a$, —$OC(S)R^a$, —$C(S)OR^a$, —$C(O)SR^a$, —$C(S)SR^a$, —$S(O)R^a$, —$SO_2R^a$, —$SO_3R^a$, —$PO_2R^aR^b$, —$PO_3R^aR^b$, —$OPO_3R^aR^b$, —$N(R^aR^b)$, —$C(O)N(R^aR^b)$, —$C(O)NR^aNR^bSO_2R^c$, —$C(O)NR^aSO_2R^c$, —$C(O)NR^aCN$, —$SO_2N(R^aR^b)$, —$NR^aSO_2R^c$, —$NR^cC(O)R^a$, —$NR^cC(O)OR^a$, —$NR^cC(O)N(R^aR^b)$, —$C(NR^c)$—$N(R^aR^b)$, —$NR^d$—$C(NR^c)$—$N(R^aR^b)$, —$NR^aN(R^aR^b)$, —$CR^c$=$CR^aR^b$, —$C$≡$CR^a$, =O, =S, =$CR^aR^b$, =$NR^a$, =$NOR^a$, =$NNR^a$, optionally substituted alkyl, optionally substituted cycloalkyl, optionally substituted aliphatic, optionally substituted cycloaliphatic, optionally substituted non-aromatic heterocyclic, optionally substituted benzyl, optionally substituted aryl, and optionally substituted heteroaryl, wherein $R^a$—$R^d$ are each independently —H, deuterium (D), or an optionally substituted aliphatic, optionally substituted cycloaliphatic, optionally substituted non-aromatic heterocyclic, optionally substituted benzyl, optionally substituted aryl, or optionally substituted heteroaryl, preferably an alkyl, benzylic or phenyl group. In addition, —$N(R^aR^b)$, taken together, can be an optionally substituted heterocyclic group.

A non-aromatic heterocyclic group, benzylic group or aryl group can also have an aliphatic or substituted aliphatic group as a substituent. A substituted aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent.

Suitable substituents for heteroaryl ring nitrogen atoms having three covalent bonds to other heteroaryl ring atoms include —OH and lower alkoxy (preferably C1-C4 alkoxy). Substituted heteroaryl ring nitrogen atoms that have three covalent bonds to other heteroaryl ring atoms are positively charged, which can be balanced by counteranions such as chloride, bromide, formate, acetate and the like. Examples of other suitable counteranions are provided in the section below directed to pharmacologically acceptable salts.

Suitable substituents for nitrogen atoms having two covalent bonds to other atoms (e.g., heteroaryl ring nitrogen atoms having two covalent bonds to other ring atoms) include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —$OR^a$, —$C(O)R^a$, —$OC(O)R^a$, —$C(O)OR^a$, —$SR^a$, —$S(O)R^a$, —$SO_2R^a$, —$SO_3R^a$, —$N(R^aR^b)$, —$C(O)N(R^aR^b)$, —$C(O)NR^aNR^bSO_2R^c$, —$C(O)NR^aSO_2R^c$, —$C(O)NR^aCN$, —$SO_2N(R^aR^b)$, —$SO_2N(R^aR^b)$, —$NR^cC(O)R^a$, —$NR^cC(O)OR^a$, —$NR^cC(O)N(R^aR^b)$, and the like. More typically, the substituents for nitrogen atoms having two covalent bonds to other atoms can be alkyl, substituted alkyl (including haloalkyl), phenyl, substituted phenyl, —$S(O)_2$-(alkyl), —$S(O)_2$—NH(alkyl) and —$S(O)_2$—N(alkyl)$_2$.

A nitrogen-containing heteroaryl or non-aromatic heterocycle can be substituted with oxygen to form an N-oxide, e.g., as in a pyridyl N-oxide, piperidyl N-oxide, and the like.

As used herein, the term "salt form," includes a salt of a compound (labeling reagent), or a mixture of salts of a compound. In addition, zwitterionic forms of a compound are also included in the term "salt form." Salts of mass tags having an amine, or other basic group can be obtained, for example, by reacting with a suitable organic or inorganic acid, such as hydrogen chloride, hydrogen bromide, acetic acid, perchloric acid and the like. Compounds with a quaternary ammonium group may also contain a counteranion such as chloride, bromide, iodide, acetate, perchlorate and the like. Salts of compounds having a carboxylic acid, or other acidic functional group, can be prepared by reacting the compound with a suitable base, for example, a hydroxide base. Accordingly, salts of acidic functional groups may have a countercation, such as sodium, potassium, magnesium, calcium, etc.

The term "hydrate form" comprises any hydration state of a compound or a mixture of more than one hydration state of a compound. For example, a mass tag of the invention can be a hemihydrate, a monohydrate, a dihydrate, etc.

3. GENERAL

Overview

The Reactive Group:

The variable "RG" of the labeling reagent or reagents used in the method, mixture, kit and/or composition embodiments can be either a reactive group, e.g., an electrophilic group or a nucleophilic group that is capable of reacting with one or more reactive analytes of a sample, or the reaction product of the reactive group and the analyte. The reactive group can be preexisting or it can be prepared in-situ. In some embodiments, in-situ preparation of the reactive group can proceed in the absence of the reactive analyte and in some embodiments, it can proceed in the presence of the reactive analyte. For example, a carboxylic acid group can be modified in-situ with water-soluble carbodiimide (e.g. 1-(3-dimethylaminopropyl)-3-ethylcarbodiimide hydrochloride; EDC) to thereby prepare an electrophilic group that can be reacted with a nucleophilic group such as an amine group. In some embodiments, activation of the carboxylic acid group of a labeling reagent with EDC can be performed in the presence of an amine (nucleophilic group) containing analyte. In some embodiments, the amine (nucleophilic group) containing analyte can also be added after the initial reaction with EDC is performed. In some embodiments, the reactive group can be generated in-situ by the in-situ removal of a protecting group. Consequently, any existing or newly created reagent or reagents that can effect the derivatization of analytes by the reaction of nucleophilic groups and/or electrophilic groups are contemplated by the method, mixture, kit and/or composition embodiments of this invention.

Where the reactive group of the labeling reagent is an electrophilic group, it can react with a suitable nucleophilic group of the analyte, or analytes. Where the reactive group of the labeling reagent is a nucleophilic group, it can react with a suitable electrophilic group of the analyte or analytes. Numerous pairs of suitable nucleophilic groups and electrophilic groups are known and often used in the chemical and biochemical arts. Non-limiting examples of reagents comprising suitable nucleophilic or electrophilic groups that can be coupled to analytes (e.g. such as proteins, peptides, nucleotides, carbohydrates, lipids, steroids or other small molecules of less that 1500 daltons) to effect their derivatization, are described in the Pierce Life Science & Analytical Research Products Catalog & Handbook (a Perstorp Biotec Company), Rockford, Ill. 61105, USA. Other suitable reagents are well known in the art and are commercially available from numerous other vendors such as Sigma-Aldrich.

The reactive group of a labeling reagent can be an amine reactive group. For example the amine reactive group can be an active ester. Active esters are well known in peptide synthesis and refer to certain esters that are easily reacted with the N-α amine of an amino acid under conditions commonly used in peptide synthesis. The amine reactive active ester can be an N-hydroxysuccinimidyl ester, a N-hydroxysulfosuccinimidyl ester, a pentafluorophenyl ester, a 2-nitrophenyl ester, a 4-nitrophenyl ester, a 2,4-dinitrophenylester or a 2,4-dihalophenyl ester.

Figure 8:
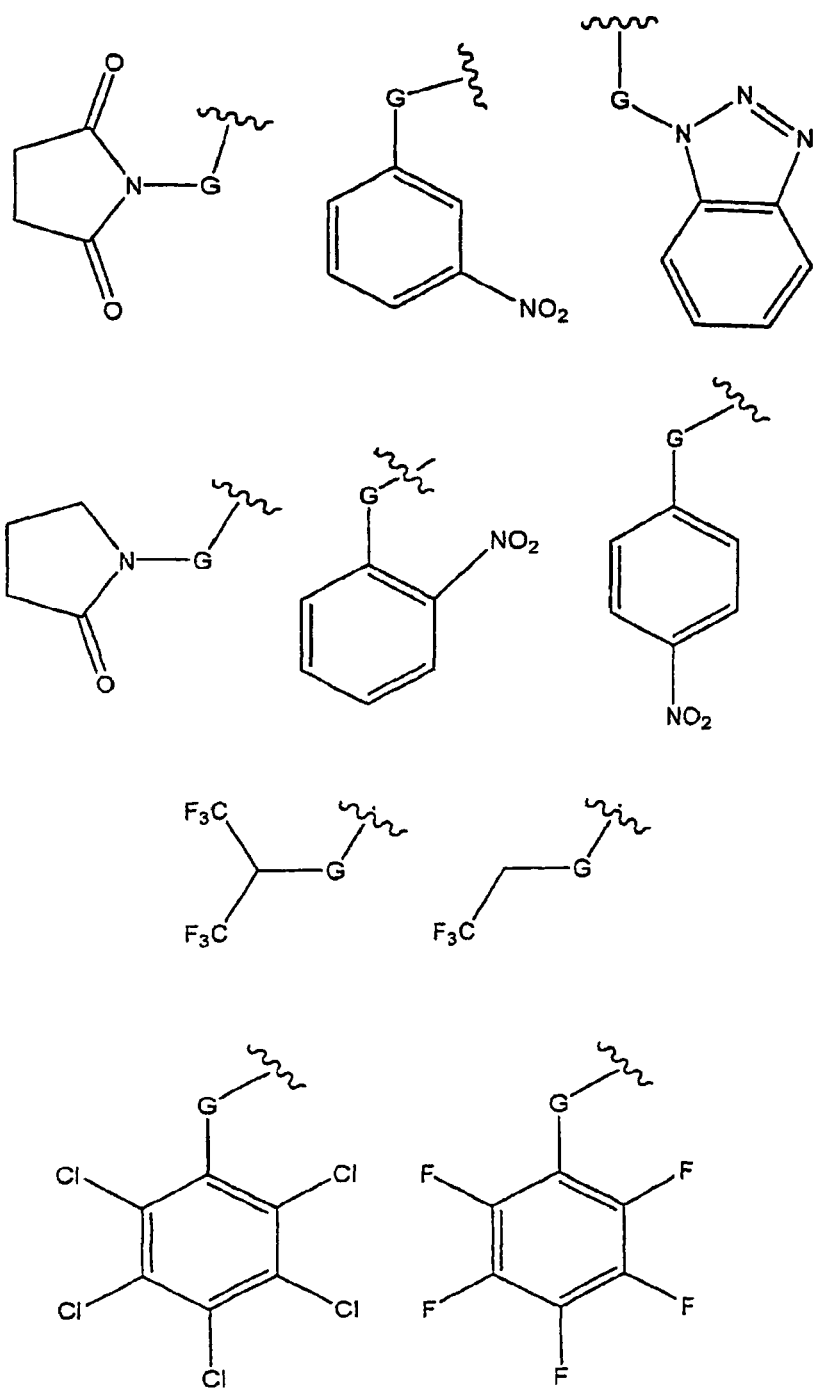
FIG. 8 illustrates exemplary formulas of leaving groups (LG) for the alcohol or thiol group of an active ester wherein each G is independently O or S, typically O.

FIG. 8 illustrates exemplary formulas of leaving groups (LG) for the alcohol or thiol group of an active ester wherein each G is independently O or S, but typically O. All of these groups are alcohol or thiol groups known to form active esters in the field of peptide chemistry wherein said alcohol or thiol group is displaced by the reaction of the N-α-amine of the amino acid with the carbonyl carbon of the ester. It should be apparent that the active ester (e.g. N-hydroxysuccinimidyl ester) of any suitable labelling/tagging reagent described herein could be prepared using well-known procedures (See: Greg T. Hermanson(1996). "The Chemistry of Reactive Groups" in "Bioconjugate Techniques" Chapter 2 pages 137-165, Academic Press, (New York); also see: Innovation And Perspectives In Solid Phase Synthesis, Editor: Roger Epton, SPCC (UK) Ltd, Birmingham, 1990). Methods for the formation of active esters of morpholine acetic acid; piperidine acetic acid, piperazine acetic acid and N-substituted piperazine acetic acids compounds that are representative examples of labeling reagents of the general formula: RP—X-LK—Y—RG are described in co-pending and commonly owned U.S. patent application Ser. No. 10/751,354, filed on Jan. 27, 2004 the entire teachings of which are incorporated herein by reference for all purposes.

In some embodiments, the reactive group of the labeling reagent can be a mixed anhydride since mixed anhydrides are known to efficiently react with amine groups to thereby produce amide bonds.

The reactive group of a labeling reagent can be a thiol reactive group. For example, the thiol reactive group can be a malemide, an alkyl halide, an aryl halide of an α-halo-acyl (a.k.a. acyl halide). Halide and halo refer to atoms of fluorine, chlorine, bromine or iodine. In some embodiments, the RG group is I—(CH$_2$)C(O)—.

The reactive group of a labeling reagent can be a hydroxyl reactive group. For example, the hydroxyl reactive group can be a trityl-halide or a silyl-halide reactive moiety. The trityl-halide reactive moieties can be substituted (e.g. Y-methoxytrityl, Y-dimethoxytrityl, Y-trimethoxytrityl, etc) or unsubstituted wherein Y is defined below. The silyl reactive moieties can be alkyl substituted silyl halides, such as Y-dimethylsilyl, Y-ditriethylsilyl, Y-dipropylsilyl, Y-diisopropylsilyl, etc.) wherein Y is defined below.

The reactive group of the labeling reagent can be a nucleophilic group. In some embodiments, the RG group is an amine group, a hydroxyl group, a thiol group or an —NH—NH$_2$ group, more typically an amine group, a hydroxyl group, or a thiol group.

The reactive group can be a group capable of reacting with a guanidine group on an analyte. In some embodiments, the RG group is

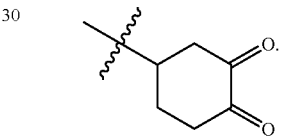

The reactive group can be a photoreactive group. In some embodiments, the RG group is

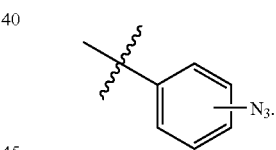

In some embodiments, the labeling reagents of the invention comprise 2 or more RG groups. Thus, a labeling reagent of formula RP—X-LK—(Y—RG)$_y$ is provided wherein y is 1-3. In some embodiments, y is 2.

The Reporter Moiety:

The reporter moiety of the labeling reagent or reagents used in the method, mixture, kit and/or composition embodiments is a group that has a unique mass (or mass to charge ratio) that can be determined. Accordingly, each reporter of a set can have a unique gross mass. Different reporters can comprise one or more heavy atom isotopes to achieve their unique mass. For example, isotopes of carbon ($^{12}$C, $^{13}$C and $^{14}$C), nitrogen ($^{14}$N and $^{15}$N), oxygen ($^{16}$O and $^{18}$O) or hydrogen (hydrogen, deuterium and tritium) exist and can be used in the preparation of a diverse group of reporter moieties. Examples of stable heavy atom isotopes include $^{13}$C, $^{15}$N, $^{18}$O and deuterium. Cost of the labeling reagent can be reduced and isotopic purity increased by avoiding $^{18}$O in the reagent. These examples of isotopes are not limiting as other light and heavy atom isotopes can also be used in the reporter. Basic starting materials suitable for preparing reporters comprising light and heavy atom isotopes are available from various commercial sources such as Cambridge Isotope Laboratories, Andover, Mass. (See: list or "basic starting materials" at www.isotope.com) and Isotec (a division of Sigma-Aldrich). Cambridge Isotope Laboratories and Isotec will also prepare desired compounds under custom synthesis contracts. Id.

A unique reporter can be associated with a sample of interest thereby labeling one or multiple analytes of that sample with a labeling reagent comprising the reporter. In this way information about the reporter can be associated with information about one or all of the analytes of the sample. However, the reporter need not be physically linked to an analyte when the reporter is determined. Rather, the unique gross mass of the reporter can, for example, be determined in a second mass analysis of a tandem mass analyzer, after ions of the labeled analyte are fragmented to thereby produce daughter fragment ions and detectable reporters. The determined reporter can be used to identify the sample from which a determined analyte originated. Further, the amount of the unique reporter, either relative to the amount of other reporters or relative to one or more calibration standards (e.g. an analyte labeled with a specific reporter), can be used to determine the relative or absolute amount (often expressed as a concentration and/or quantity) of analyte in the sample or samples. Therefore information, such as the amount of one or more analytes in a particular sample, can be associated with the reporter moiety that is used to label each particular sample. Where the identity of the analyte or analytes is also determined, that information can be correlated with information pertaining to the different reporters to thereby facilitate the determination of the identity and amount of each labeled analyte in one or a plurality of samples.

The reporter either comprises a fixed charge or is capable of becoming ionized. Because the reporter either comprises a fixed charge or is capable of being ionized, the labeling reagent might be isolated or used to label the reactive analyte in a salt or zwitterionic form. Ionization of the reporter facilitates its determination in a mass spectrometer. Accordingly, the reporter can be determined as a ion, sometimes referred to as a signature ion. When ionized, the reporter can comprise one or more net positive or negative charges. Thus, the reporter can comprise one or more acidic groups or basic groups since such groups can be easily ionized in a mass spectrometer. For example, the reporter can comprise one or more basic nitrogen atoms (positive charge) or one or more ionizable acidic groups such as a carboxylic acid group, sulfonic acid group or phosphoric acid group (negative charge). In some embodiments, the reporter can comprise a substituted or unsubstituted benzyl ion.

The reporter can be selected so that it does not substantially sub-fragment under conditions typical for the analysis of the analyte. The reporter can be chosen so that it does not substantially sub-fragment under conditions of dissociative energy applied to cause fragmentation of both bonds X and Y of at least a portion of selected ions of a labeled analyte in a mass spectrometer. By "does not substantially sub-fragment" we mean that fragments of the reporter are difficult or impossible to detect above background noise when applied to the successful analysis of the analyte of interest. The gross mass of a reporter can be intentionally selected to be different as compared with the mass of the analyte sought to be determined or any of the expected fragments of the analyte. For example, where proteins or peptides are the analytes, the reporter's gross mass can be chosen to be different as compared with any naturally occurring amino acid or peptide, or expected fragments thereof. This can facilitate analyte determination since, depending on the analyte, the lack of any possible components of the sample having the same coincident mass can add confidence to the result of any analysis. Examples of mass ranges where little background can be expected for peptides can be found in Table 1.

TABLE 1

Possible "Quiet Zones" For Selection Of Label Fragment Ion m/z

| M/z start-end |
|---|
| 10-14 |
| 19-22 |
| 24-26 |
| 31-38 |
| 40-40 |
| 46-50 |
| 52-52 |
| 58-58 |
| 61-69 |
| 71-71 |
| 74-83 |
| 89-97 |
| 103-109 |
| 113-119 |
| 121-125 |
| 128-128 |
| 131-135 |
| 137-147 |
| 149-154 |
| 156-156 |
| 160-174 |
| 177-182 |
| 184-184 |
| 188-189 |
| 191-191 |
| 202-207 |
| 210-210 |
| 216-222 |
| 224-226 |

The gross mass of a reporter can be less than 250 Daltons. Such a small molecule can be easily determined in the second mass analysis, free from other components of the sample having the same coincident mass in the first mass analysis. In this context, the second mass analysis can be performed, typically in a tandem mass spectrometer, on selected ions that are determined in the first mass analysis. Because ions of a particular mass to charge ratio can be specifically selected out of the first mass analysis for possible fragmentation and further mass analysis, the non-selected ions from the first mass analysis are not carried forward to the second mass analysis and therefore do not contaminate the spectrum of the second mass analysis. Furthermore, the sensitivity of a mass spectrometer and the linearity of the detector (for purposes of quantitation) can be quite robust in this low mass range. Additionally, the present state of mass spectrometer technology can allow for baseline mass resolution of less than one Dalton in this mass range. These factors may prove to be useful advancements to the state of the art.

The Linker Moiety:

The linker moiety represented by LK, $LK^1$, $LK^2$, $LK^3$, $LK^4$, $LK^5$ and $LK^6$ of the compounds used with the method, mixture, kit and/or composition embodiments links the reporter to the analyte or the reporter to the reactive group depending on whether or not a reaction with the analyte has occurred. The linker can be selected to produce a neutral species when both bonds X and Y are fragmented (i.e. undergoes neutral loss upon fragmentation of both bonds X and Y). The linker can be a very small moiety such as a carbonyl or thiocarbonyl group. For example, the linker can comprise at least one heavy atom isotope and comprise the formula:

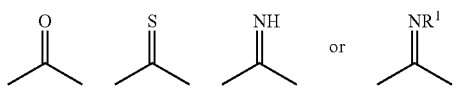

wherein each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms. The linker can be a larger moiety such as amino acid or heteroalkyl. The linker can be a polymer or a biopolymer (e.g., a peptide). The linker can be designed to sub-fragment when subjected to dissociative energy levels; including sub-fragmentation to thereby produce one or more neutral fragments of the linker. In some embodiments, only neutral fragments are produced from the linker.

Figure 9A:
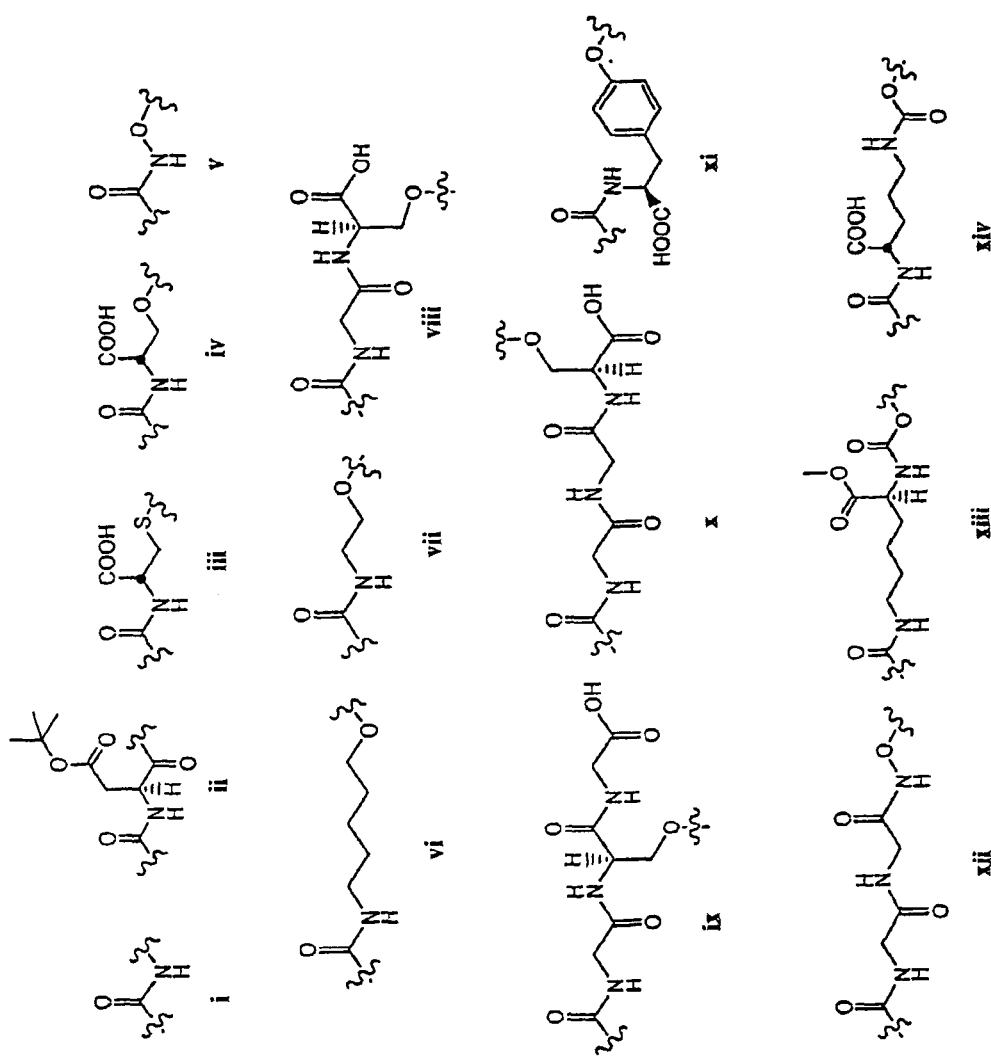
FIGS. 9A-9B illustrate moieties i-xiv, which can be comprised by the LK group in some embodiments.
Figure 9B:
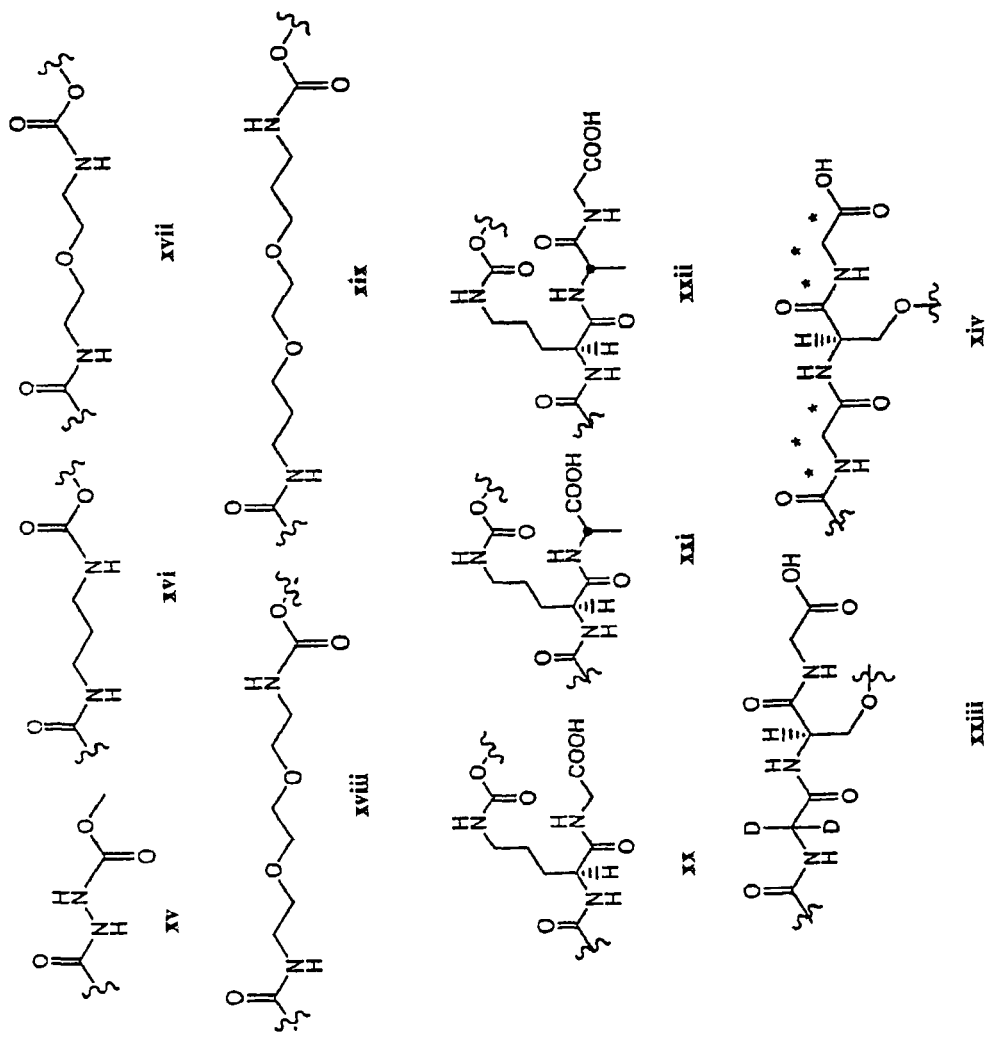

FIGS. 9A-9B depict moieties i-xiv, which can be comprised by the LK group in some embodiments. Each bond terminated with the wavy line indicates the point of attachment to a reporter, support, reactive group or analyte. The linker moiety can comprise one or more heavy atom isotopes such that its mass compensates for the difference in gross mass between the reporters for each labeled analyte of a mixture or for the reagents of set and/or kit. Moreover, the aggregate gross mass (i.e. the gross mass taken as a whole) of the reporter-linker combination can be the same for each labeled analyte of a mixture or for the reagents of set and/or kit. More specifically, the linker moiety can compensate for the difference in gross mass between reporters of labeled analytes from different samples wherein the unique gross mass of the reporter correlates with the sample from which the labeled analyte originated and the aggregate gross mass of the reporter-linker combination is the same for each labeled analyte of a sample mixture regardless of the sample from which it originated. In this way, the gross mass of identical analytes in two or more different samples can have the same gross mass when labeled and then mixed to produce a sample mixture.

For example, the labeled analytes, or labeling reagent (e.g., mass tags) of a set and/or kit for labeling the analytes, can be isomers or isobars. Thus, if ions of a particular mass to charge ratio (taken from the sample mixture) are selected (i.e. selected ions) in a mass spectrometer from an initial mass analysis of the sample mixture, identical analytes from the different samples that make up the sample mixture are represented in the selected ions in proportion to their respective concentration and/or quantity in the sample mixture. Accordingly, the linker not only links the reporter to the analyte, it also can serve to compensate for the differing masses of the unique reporter moieties to thereby harmonize the gross mass of the reporter-linker combination in the labeled analytes of the various samples.

Because the linker can act as a mass balance for the reporter in the labeling reagents such that the aggregate gross mass of the reporter-linker combination is the same for all reagents of a set or kit, the greater the number of atoms in the linker, the greater the possible number of different isomeric/isobaric labeling reagents of a set and/or kit. Stated differently, generally the greater the number of atoms that a linker comprises, the greater number of potential reporter-linker combinations exist since isotopes can be substituted at most any position in the linker to thereby produce isomers or isobars of the linker portion wherein the linker portion is used to offset the differing masses of the reporter portion and thereby create a set of reporter-linker isomers or isobars. Such diverse sets of labeling reagents are particularly well suited for multiplex analysis of analytes in the same and/or different samples.

The total number of labeling reagents of a set and/or kit can be two, three, four, five, six, seven, eight, nine, ten or more. The diversity of the labeling reagents of a set or kit is limited only by the number of atoms of the reporter and linker moieties, the heavy atom isotopes available to substitute for the light isotopes and the various synthetic configurations in which the isotopes can be synthetically placed. As suggested above however, numerous isotopically enriched basic starting materials are readily available from manufacturers such as Cambridge Isotope Laboratories and Isotec. Such isotopically enriched basic starting materials can be used in the synthetic processes used to produce sets of isobaric and isomeric labeling reagents or be used to produce the isotopically enriched starting materials that can be used in the synthetic processes used to produce sets of isobaric and isomeric labeling reagents. Some examples of the preparation of isobaric labeling reagents suitable for use in a set of labeling reagents can be found in the Examples section, below.

The Reporter-Linker Combination:

The labeling reagents described herein comprise reporters and linkers that are linked through the bond X. As described above, the reporter-linker combination can be identical in gross mass for each member of a set and/or kit of labeling reagents. Moreover, bond X of the reporter-linker combination of the labeling reagents can be designed to fragment, in at least a portion of the selected ions, when subjected to dissociative energy levels thereby releasing the reporter from the analyte. Accordingly, the gross mass of the reporter (as a m/z ratio) and its intensity can be observed directly in MS/MS analysis.

The reporter-linker combination can comprise various combinations of the same or different heavy atom isotopes amongst the various labeling reagents of a set or kit. In the scientific literature this has sometimes been referred to as coding or isotope coding. For example, Abersold et al. has disclosed the isotope coded affinity tag (ICAT; see WO 00/11208). In one respect, the reagents of Abersold et al. differ from the labeling reagents of this invention in that Abersold does not teach two or more same mass labeling reagents such as isomeric or isobaric labeling reagents.

Mass Spectrometers/Mass Spectrometry (MS):

The methods of this invention can be practiced using tandem mass spectrometers and other mass spectrometers that have the ability to select and fragment molecular ions. Tandem mass spectrometers (and to a lesser degree single-stage mass spectrometers) have the ability to select and fragment molecular ions according to their mass-to-charge (m/z) ratio, and then record the resulting fragment (daughter) ion spectra. More specifically, daughter fragment ion spectra can be generated by subjecting selected ions to dissociative energy levels (e.g. collision-induced dissociation (CID)). For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and high-energy CID using MALDI-TOF (time of flight)-TOF MS. For a recent review of tandem mass spectrometers please see: R. Aebersold and D. Goodlett, *Mass Spectrometry in Proteomics. Chem. Rev.* 101: 269-295 (2001). Also see U.S. Pat. No. 6,319,476, herein incorporated by reference for all purposes, for a discussion of TOF-TOF mass analysis techniques.

Fragmentation by Dissociative Energy Levels:

It is well accepted that bonds can fragment as a result of the processes occurring in a mass spectrometer. Moreover, bond fragmentation can be induced in a mass spectrometer by subjecting ions to dissociative energy levels. For example, the dissociative energy levels can be produced in a mass spectrometer by collision-induced dissociation (CID). Those of ordinary skill in the art of mass spectrometry will appreciate that other exemplary techniques for imposing dissociative energy levels that cause fragmentation include, but are not limited to, photo dissociation, electron capture and surface induced dissociation.

The process of fragmenting bonds by collision-induced dissociation involves increasing the kinetic energy state of selected ions to a point where bond fragmentation occurs. For example, kinetic energy can be transferred by collision with an inert gas (such as nitrogen, helium or argon) in a collision cell. The amount of kinetic energy that can be transferred to the ions is proportional to the number of gas molecules that are allowed to enter the collision cell. When more gas molecules are present, a greater amount of kinetic energy can be transferred to the selected ions, and less kinetic energy is transferred when there are fewer gas molecules present.

It is therefore clear that the dissociative energy level in a mass spectrometer can be controlled. It is also well accepted that certain bonds are more labile than other bonds. The lability of the bonds in an analyte or the reporter-linker moiety depends upon the nature of the analyte or the reporter-linker moiety. Accordingly, the dissociative energy levels can be adjusted so that the analytes and/or the labels (e.g. the reporter-linker combinations) can be fragmented in a manner that is determinable. One of skill in the art will appreciate how to make such routine adjustments to the components of a mass spectrometer to thereby achieve the appropriate level of dissociative energy to thereby fragment at least a portion of ions of labeled analytes into ionized reporter moieties and daughter fragment ions.

For example, dissociative energy can be applied to ions that are selected/isolated from the first mass analysis. In a tandem mass spectrometer, the extracted ions can be subjected to dissociative energy levels and then transferred to a second mass analyzer. The selected ions can have a selected mass to charge ratio. The mass to charge ratio can be within a range of mass to charge ratios depending upon the characteristics of the mass spectrometer. When collision induced dissociation is used, the ions can be transferred from the first to the second mass analyzer by passing them through a collision cell where the dissociative energy can be applied to thereby produce fragment ions. For example the ions sent to the second mass analyzer for analysis can include all, some, or a portion, of the remaining (unfragmented) selected ions, as well as reporter ions (signature ions) and daughter fragment ions of the labeled analyte.

Analyte Determination by Computer Assisted Database Analysis:

In some embodiments, analytes can be determined based upon daughter-ion fragmentation patterns that are analyzed by computer-assisted comparison with the spectra of known or "theoretical" analytes. For example, the daughter fragment ion spectrum of a peptide ion fragmented under conditions of low energy CID can be considered the sum of many discrete fragmentation events. The common nomenclature differentiates daughter fragment ions according to the amide bond that breaks and the peptide fragment that retains charge following bond fission. Charge-retention on the N-terminal side of the fissile amide bond results in the formation of a b-type ion. If the charge remains on the C-terminal side of the broken amide bond, then the fragment ion is referred to as a y-type ion. In addition to b- and y-type ions, the CID mass spectrum may contain other diagnostic fragment ions (daughter fragment ions). These include ions generated by neutral loss of ammonia (−17 amu) from glutamine, lysine and arginine or the loss of water (−18 amu) from hydroxyl-containing amino acids such as serine and threonine. Certain amino acids have been observed to fragment more readily under conditions of low-energy CID than others. This is particularly apparent for peptides containing proline or aspartic acid residues, and even more so at aspartyl-proline bonds (Mak, M. et al., *Rapid Commun. Mass Spectrom.*, 12: 837-842) (1998). Accordingly, the peptide bond of a Z-pro dimer or Z-asp dimer, wherein Z is any natural amino acid, pro is proline and asp is aspartic acid, will tend to be more labile as compared with the peptide bond between all other amino acid dimer combinations.

For peptide and protein samples therefore, low-energy CID spectra contain redundant sequence-specific information in overlapping b- and y-series ions, internal fragment ions from the same peptide, and immonium and other neutral-loss ions. Interpreting such CID spectra to assemble the amino acid sequence of the parent peptide de novo is challenging and time-consuming. The most significant advances in identifying peptide sequences have been the development of computer algorithms that correlate peptide CID spectra with peptide sequences that already exist in protein and DNA sequence databases. Such approaches are exemplified by programs such as SEQUEST (Eng, J. et al. *J. Am. Soc. Mass Spectrom.*, 5: 976-989 (1994)) and MASCOT (Perkins, D. et al. *Electrophoresis*, 20: 3551-3567 (1999)).

In brief, experimental peptide CID spectra (MS/MS spectra) are matched or correlated with 'theoretical' daughter fragment ion spectra computationally generated from peptide sequences obtained from protein or genome sequence databases. The match or correlation is based upon the similarities between the expected mass and the observed mass of the daughter fragment ions in MS/MS mode. The potential match or correlation is scored according to how well the experimental and 'theoretical' fragment patterns coincide. The constraints on databases searching for a given peptide amino acid sequence are so discriminating that a single peptide CID spectrum can be adequate for identifying any given protein in a whole-genome or expressed sequence tag (EST) database. For other reviews please see: Yates, J. R. Trends, *Genetics*, 16: 5-8 (2000) and Yates, J. R., *Electrophoresis* 19: 893-900 (1998).

Accordingly, daughter fragment ion analysis of MS/MS spectra can be used not only to determine the analyte of a labeled analyte, it can also be used to determine analytes from which the determined analyte originated. For example, identification of a peptide in the MS/MS analysis can be can be used to determine the protein from which the peptide was cleaved as a consequence of an enzymatic digestion of the protein. It is envisioned that such analysis can be applied to other analytes, such as oligonucleotides.

Bonds X and Y:

X is a bond between an atom of the reporter and an atom of the linker. Y is a bond between an atom of the linker and an atom of either the reactive group or, if the labeling reagent has been reacted with a reactive analyte, the analyte. Bonds X and Y of the various labeling reagents (i.e. RP—X-LK—Y—RG) that can be used in the embodiments of this invention can fragment, in at least a portion of selected ions, when subjected to dissociative energy levels. Therefore, the dissociative energy level can be adjusted in a mass spectrometer so that both bonds X and Y fragment in at least a portion of the selected ions of the labeled analytes (i.e. RP—X-LK—Y-Analyte). Fragmentation of bond X releases the reporter from the analyte so that the reporter can be determined independently from the analyte. Fragmentation of bond Y releases the reporter-linker combination from the analyte, or the linker from the analyte, depending on whether or not bond X has already been fragmented. Bond Y can be more labile than bond X. Bond X can be more labile than bond Y. Bonds X and Y can be of the same relative lability.

In some embodiments, bond X can be more labile than bond Y. In some embodiments, bond X cleaves and bond Y remains intact. In still other embodiments, bond X cleaves and bond Y cleaves.

When the analyte of interest is a protein or peptide, the relative lability of bonds X and Y can be adjusted with regard to an amide (peptide) bond. Bond X, bond Y or both bonds X and Y can be more, equal or less labile as compared with a typical amide (peptide) bond. For example, under conditions of dissociative energy, bond X and/or bond Y can be less prone to fragmentation as compared with the peptide bond of a Z-pro dimer or Z-asp dimer, wherein Z is any natural amino acid, pro is proline and asp is aspartic acid. In some embodiments, bonds X and Y will fragment with approximately the same level of dissociative energy as a typical amide bond. In some embodiments, bonds X and Y will fragment at a greater level of dissociative energy as compared with a typical amide bond.

In some embodiments, bonds X and Y can also exist such that fragmentation of bond Y results in the fragmentation of bond X, and vice versa. In this way, both bonds X and Y can fragment essentially simultaneously such that no substantial amount of analyte, or daughter fragment ion thereof, comprises a partial label in the second mass analysis. By "substantial amount of analyte" we mean that less than 25%, and preferably less than 10%, partially labeled analyte can be determined in the MS/MS spectrum.

Because there can be a clear demarcation between labeled and unlabeled fragments of the analyte in the spectra of the second mass analysis (MS/MS), this feature can simplify the identification of the analytes from computer assisted analysis of the daughter fragment ion spectra. Moreover, because the fragment ions of analytes can, in some embodiments, be either fully labeled or unlabeled (but not partially labeled) with the reporter/linker moiety, there can be little or no scatter in the masses of the daughter fragment ions caused by isotopic distribution across fractured bonds such as would be the case where isotopes were present on each side of a single labile bond of a partially labeled analyte routinely determined in the second mass analysis.

Labeling of Analytes:

Analytes can be labeled by reacting a functional group of the analyte with the reactive group (RG) of the labeling reagent. As discussed previously, the functional group on the analyte can be one of an electrophilic group or a nucleophilic group and the functional group (i.e. the RG or reactive group) of the labeling reagent can be the other of the electrophilic group or a nucleophilic group. The electrophilic group and nucleophilic group can react to form a covalent link between the analyte and the labeling reagent.

The labeling reaction can take place in solution. In some embodiments, one of the analyte or the labeling reagent can be support bound. The labeling reaction can sometimes be performed in aqueous conditions. Aqueous conditions can be selected for the labeling of biomolecules such as proteins, peptides, nucleotides and oligonucleotides. The labeling reaction can sometimes be performed in organic solvent or a mixture of organic solvents. Organic solvents can be selected for analytes that are small molecules. Mixtures of water and organic solvent or organic solvents can be used across a broad range. For example, a solution of water and from about 60 percent to about 95 percent organic solvent or solvents (v/v) can be prepared and used for labeling the analyte. In some embodiments, a solution of water and from about 65 percent to about 80 percent organic solvent or solvents (v/v) can be prepared and used for labeling the analyte. Non-limiting examples of organic solvents include N,N'-dimethylformamide (DMF), acetonitrile (ACN), and alcohol such as methanol, ethanol, propanol and/or butanol.

When performing a labeling reaction, the pH can be modulated. The pH can be in the range of 4-10. The pH can be outside this range. Generally, the basicity of non-aqueous reactions can be modulated by the addition of non-nucleophilic organic bases. Non-limiting examples of suitable bases include N-methylmorpholine, triethylamine and N,N-diisopropylethylamine. Alternatively, the pH of water containing solvents can be modulated using biological buffers such as (N-[2-hydroxyethyl]piperazine-N'-[2-ethanesulfonic acid) (HEPES) or 4-morpholineethane-sulfonic acid (MES) or inorganic buffers such as sodium carbonate and/or sodium bicarbonate. Because at least one of the reactive groups can be electrophilic, it can be desirable to select the buffer to not contain any nucleophilic groups. Those of skill in the are will appreciate other buffers that can be used to modulate the pH of a labeling reaction, with the application of ordinary experimentation, so as to facilitate the labeling of an analyte with a labeling reagent.

Sample Processing:

In certain embodiments of this invention, a sample can be processed prior to, as well as after, labeling of the analytes. Processing can be applied to the whole of a sample, or a fraction thereof. Processing can be applied to sample mixtures or a fraction thereof. Processing can be used to de-complexify the sample or be used to put the sample in a better form for analysis. The processing can facilitate the labeling of the analytes. The processing can facilitate the analysis of the sample components (e.g. labeled analytes). The processing can simplify the handling of the samples. The processing can facilitate two or more of the foregoing.

For example, a sample can be treated with an enzyme. The enzyme can be a protease (to degrade proteins and peptides), a nuclease (to degrade oligonucleotides) or some other enzyme. The enzyme can be chosen to have a very predictable degradation pattern. Two or more proteases and/or two or more nuclease enzymes may also be used together, or with other enzymes, to thereby degrade sample components.

For example, the proteolytic enzyme trypsin is a serine protease that cleaves peptide bonds between lysine or arginine and an unspecific amino acid to thereby produce peptides that comprise an amine terminus (N-terminus) and lysine or arginine carboxyl terminal amino acid (C-terminus). In this way the peptides from the cleavage of the protein are predictable and their presence and/or quantity, in a sample from a trypsin digest, can be indicative of the presence and/or quantity of the protein of their origin. Moreover, the free amine termini of a peptide can be a good nucleophile that facilitates its labeling. Other exemplary proteolytic enzymes include papain, pepsin, ArgC, LysC, V8 protease, AspN, pronase, chymotrypsin and carboxypeptidase C.

For example, a protein (e.g. protein Z) might produce three peptides (e.g. peptides B, C and D) when digested with a protease such as trypsin. Accordingly, a sample that has been digested with a proteolytic enzyme, such as trypsin, and that, when analyzed is confirmed to contain peptides B, C and D, can be said to have originally comprised the protein Z. The quantity of peptides B, C and D will also correlate with the quantity of protein Z in the sample that was digested. In this way, any determination of the identity and/or quantify of one or more of peptides B, C and D in a sample (or a fraction thereof), can be used to identify and/or quantify protein Z in the original sample (or a fraction thereof).

Because activity of the enzymes is predictable, the sequence of peptides that are produced from degradation of a protein of known sequence can be predicted. With this information, "theoretical" peptide information can be generated. A determination of the 'theoretical" peptide fragments in computer assisted analysis of daughter fragment ions (as described above) from mass spectrometry analysis of an actual sample can therefore be used to determine one or more peptides or proteins in one or more unknown samples.

In some cases, sample processing can include treatment of precursors to the analyte or analytes to be labeled. For example, if the analyte or analytes to be labeled are peptides derived from a digested protein and the labeling reagent is, for this example, selected to react with amine groups (e.g. N-α-amine groups and N-ε-amine group of lysine) of the peptide or peptide analytes, the protein (the analyte precursor molecule) of the sample may be processed in a manner that facilitates the labeling reaction. In this example, the protein can be reduced with a reducing agent (e.g. tris[2-carboxyethyl]phosphine (TCEP)) and the thiol groups then blocked by reaction with a blocking reagent (e.g. methyl methanethiosulfonate (MMTS)). In this way the thiol groups of the protein are blocked and therefore do not interfere with the labeling reaction between the amines of the analytes and labeling reagent.

Those of skill in the art will appreciate that treatment of certain other precursor molecules can be performed using readily available reagents and protocols that can be adapted with the aid of routing experimentation. The precise choices or reagents and conditions can be selected depending on the nature of the analyte to be labeled and the labeling reagent.

In some embodiments, sample processing can include the immobilization of the analytes or analyte precursors to a solid support, whether labeled with a labeling reagent or not. In some embodiments, immobilization can facilitate reducing sample complexity. In some embodiments, immobilization can facilitate analyte labeling. In some embodiments, immobilization can facilitate analyte precursor labeling. In some embodiments, immobilization can facilitate selective labeling of a fraction of sample components comprising a certain property (e.g. they comprise or lack cysteine moieties). The immobilization can facilitate two or more of the foregoing.

Separations:

In some embodiments, the processing of a sample or sample mixture of labeled analytes can involve separation. One or more separations can be performed on the labeled or unlabeled analytes, labeled or unlabeled analyte precursors, or fractions thereof. One or more separations can be performed on one or more fractions obtained from a solid phase capture. Separations can be preformed on two or more of the foregoing.

For example, a sample mixture comprising differentially labeled analytes from different samples can be prepared. By differentially labeled we mean that each of the labels comprises a unique property that can be identified (e.g. comprises a unique reporter moiety that produces a unique "signature ion" in MS/MS analysis). In order to analyze the sample mixture, components of the sample mixture can be separated and mass analysis performed on only a fraction of the sample mixture. In this way, the complexity of the analysis can be substantially reduced since separated analytes can be individually analyzed for mass thereby increasing the sensitivity of the analysis process. Of course the analysis can be repeated one or more time on one or more additional fractions of the sample mixture to thereby allow for the analysis of all fractions of the sample mixture.

Separation conditions under which identical analytes that are differentially labeled co-elute at a concentration, or in a quantity, that is in proportion to their abundance in the sample mixture can be used to determine the amount of each labeled analyte in each of the samples that comprise the sample mixture provided that the amount of each sample added to the sample mixture is known. Accordingly, in some embodiments, separation of the sample mixture can simplify the analysis whilst maintaining the correlation between signals determined in the mass analysis (e.g. MS/MS analysis) with the amount of the differently labeled analytes in the sample mixture:

The separation can be performed by chromatography. For example, liquid chromatography/mass spectrometry (LC/MS) can be used to effect such a sample separation and mass analysis. Moreover, any chromatographic separation process suitable to separate the analytes of interest can be used. For example, the chromatographic separation can be normal phase chromatography, reversed-phase chromatography, ion-exchange chromatography, size exclusion chromatography or affinity chromatorgraphy.

The separation can be performed electrophoretically. Non-limiting examples of electrophoretic separations techniques that can be used include, but are not limited to, 1D electrophoretic separation, 2D electrophoretic separation and/or capillary electrophoretic separation.

An isobaric labeling reagent or a set of reagents can be used to label the analytes of a sample. Isobaric labeling reagents are particularly useful when a separation step is performed because the isobaric, labels of a set of labeling reagents are structurally and chemically indistinguishable (and can be indistinguishable by gross mass until fragmentation removes the reporter from the analyte). Thus, all analytes of identical composition that are labeled with different isobaric labels can chromatograph in exactly the same manner (i.e. co-elute). Because they are structurally and chemically indistinguishable, the eluent from the separation process can comprise an amount of each isobarically labeled analyte that is in proportion to the amount of that labeled analyte in the sample mixture. Furthermore, from the knowledge of how the sample mixture was prepared (portions of samples, an other optional components (e.g. calibration standards) added to prepare the sample mixture), it is possible to relate the amount of labeled analyte in the sample mixture back to the amount of that labeled analyte in the sample from which it originated.

The labeling reagents can also be isomeric. Although isomers can sometimes be chromatographically separated, there are circumstances, that are condition dependent, where the separation process can be operated to co-elute all of the identical analytes that are differentially labeled wherein the amount of all of the labeled analytes exist in the eluent in proportion to their concentration and/or quantity in the sample mixture.

Figures 1, 7C:
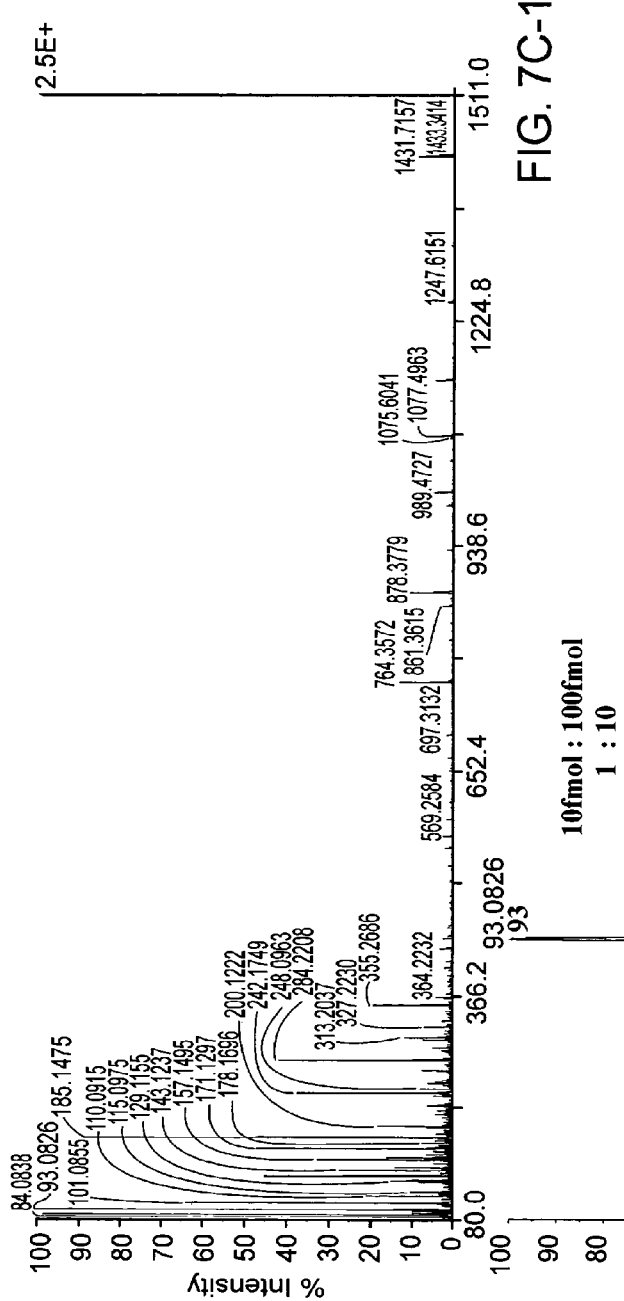
Figures 2, 7C:
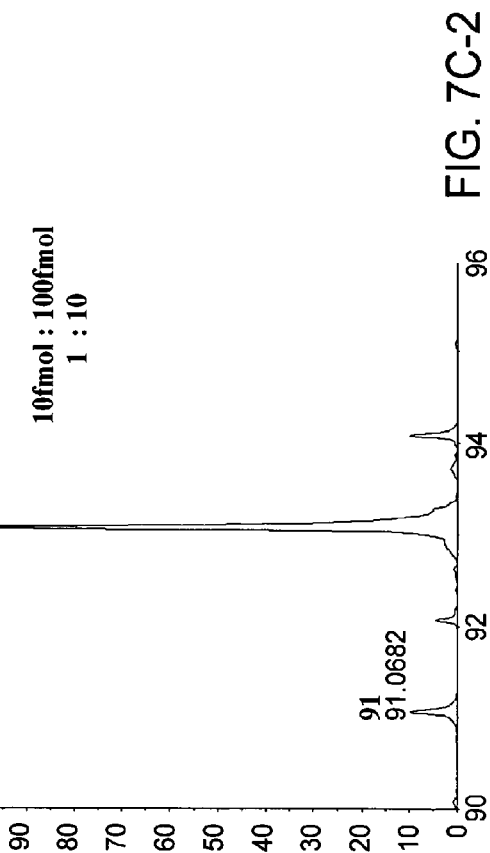

As used herein, isobars differ from isomers in that isobars are structurally and chemically indistinguishable compounds (except for isotopic content and/or distribution) of the same gross mass (See for example, FIG. 1) whereas isomers are structurally and/or chemically distinguishable compounds of the same gross mass.

Workflows:

In some embodiments, the labeling of the analytes of a sample can be performed prior to performing sample processing steps. In some embodiments, the labeling of analytes can be performed amongst other sample processing steps. In some embodiments, the labeling of analytes is the last step of sample processing and/or immediately precedes the preparation of a sample mixture.

Using proteomic analysis as a non-limiting example, there are at least several possible workflows that might be used. To aid in understanding of the following discussion a distinction is sometimes made between the precursor protein and the analyte peptide. However, it should be understood that either, or both, of the protein and the peptide can be considered analytes as described herein.

In one type of workflow, the precursor proteins can be digested to peptide analytes that can thereafter be labeled with labeling reagent. In another type of workflow, the precursor proteins can be labeled with the labeling reagent and then digested to labeled peptide analytes. In another type of workflow, the precursor proteins can be captured on a solid support, digested and then the support bound peptides can be labeled. Optionally the flow through peptides can also labeled. In another type of workflow, the precursor proteins can be captured on a solid support, labeled and then the support bound protein can be digested to produce labeled peptides. Optionally the flow through peptides can also analyzed. Regardless of the workflow, additional sample processing (e.g. separation steps) can be performed on the labeled peptides as desired before MS analysis.

In summary, the analyte, can be labeled before or after one or more separation and/or sample processing steps have been performed. It is not a limitation of this invention when the labeling of the analyte takes place so long as the analytes of one or more samples can be labeled and one or more sample mixtures can be prepared from differentially labeled samples.

Relative and Absolute Quantitation of Analytes:

In some embodiments, the relative quantitation of differentially labeled identical analytes of a sample mixture is possible. Relative quantitation of differentially labeled identical analytes is possible by comparison of the relative amounts of reporter (e.g. intensity, area and/or height of the peak reported) that are determined in the second mass analysis for a selected, labeled analyte observed in a first mass analysis. Put differently, where each reporter can be correlated with information for a particular sample used to produce a sample mixture, the relative amount of that reporter, with respect to other reporters observed in the second mass analysis, is the relative amount of that analyte in the sample mixture. Where components combined, to form the sample mixture is known, the relative amount of the analyte in each sample used to prepare the sample mixture can be back calculated based upon the relative amounts of reporter observed for the ions of the labeled analyte selected from the first mass analysis. This process can be repeated for all of the different labeled analytes observed in the first mass analysis. In this way, the relative amount (often expressed in terms of concentration and/or quantity) of each reactive analyte, in each of the different samples used to produce the sample mixture, can be determined.

In some embodiments, absolute quantitation of analytes can be determined. For these embodiments, a known amount of one or more differentially labeled analytes (the calibration standard or calibration standards) can be added to the sample mixture. The calibration standard can be an expected analyte that is labeled with an isomeric or isobaric label of the set of labels used to label the analytes of the sample mixture provided that the reporter for the calibration standard is unique as compared with any of the samples used to form the sample mixture. Once the relative amount of reporter for the calibration standard, or standards, is determined with relation to the relative amounts of the reporter for the differentially labeled analytes of the sample mixture, it is possible to calculate the absolute amount (often expressed in concentration and/or quantity) of all of the differentially labeled analytes in the sample mixture. In this way, the absolute amount of each differentially labeled analyte (for which there is a calibration standard in the sample from which the analyte originated) can also be determined based upon the knowledge of how the sample mixture was prepared.

Notwithstanding the foregoing, corrections to the intensity (or area or height) of the reporter ions (i.e. signature ions) can be made, as appropriate, for any naturally occurring, or artificially created, isotopic abundance within the reporters. A more sophisticated example of these types of corrections can also be found in copending and co-owned U.S. Provisional Patent Application Ser. No. 60/524,844, entitled: "Method and Apparatus For De-Convoluting A Convoluted Spectrum", filed on Nov. 26, 2003. The more care taken to accurately quantify the intensity of each reporter, the more accurate will be the relative and absolute quantification of the analytes in the original samples.

In brief, using these methods, the intensity of up mass and down mass isotope peaks associated with a particular signature ion can be added to the major intensity peak associated with the signature ion (i.e. the reporter) so that the contribution of all intensities can be properly attributed to the correct reporter. Peak intensities not associated with a particular signature ion can be deducted as appropriate. By allocating all peak intensities to the proper signature ions, the relative and absolute quantification information associated with a signature ion can be quite accurate. The more accurately intensities are allocated to the correct reporter, the more accurate the quantitative determinations can be.

Proteomic Analysis:

The methods, mixtures, kits and/or compositions of this invention can be used for complex analysis because samples can be multiplexed, analyzed and reanalyzed in a rapid and repetitive manner using mass analysis techniques. For example, sample mixtures can be analyzed for the amount of individual analytes in one or more samples. The amount (often expressed in concentration and/or quantity) of those analytes can be determined for the samples from which the sample mixture was comprised. Because the sample processing and mass analyses can be performed rapidly, these methods can be repeated numerous times so that the amount of many differentially labeled analytes of the sample mixture can be determined with regard to their relative and/or absolute amounts in the sample from which the analyte originated.

One application where such a rapid multiplex analysis is useful is in the area of proteomic analysis. Proteomics can be viewed as an experimental approach to describe the information encoded in genomic sequences in terms of structure, function and regulation of biological processes. This may be achieved by systematic analysis of the total protein component expressed by a cell or tissue. Mass spectrometry, used in combination with the method, mixture, kit and/or composition embodiments of this invention is one possible tool for such global protein analysis.

For example, with a set of four isobaric labeling reagents, it is possible to obtain four time points in an experiment to determine up or down regulation of protein expression, for example, based upon response of growing cells to a particular stimulant. It is also possible to perform fewer time points but to incorporate one or two controls. In all cases, up or down regulation of the protein expression, optionally with respect to the controls, can be determined in a single multiplex experiment. Moreover, because processing is performed in parallel the results are directly comparable, since there is no risk that slight variations in protocol may have affected the results.

4. DESCRIPTION OF VARIOUS EMBODIMENTS OF THE INVENTION

Various embodiments include one or more of kits, arrays, libraries, mixtures, compounds, labeled analytes, and methods as described in the following sections.

A. Compounds

Each of the various embodiments can employ one or more compounds represented by structural formula $I^w$:

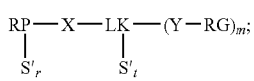

or a salt form and/or hydrate form thereof. The variable m can be an integer from one to 3, typically 1, wherein the compound can be represented by structural formula $I^\#$:

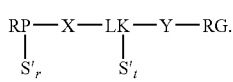

The variables in the above structural formulas can be independently selected for each compound as follows:
  RG can be a nucleophilic group or an electrophilic group, or a reaction product of an analyte with a nucleophilic group or an electrophilic group;
  r and t can be both 0 or one of r and t can be 1 and the other can be 0;
  When one of r and t is 1, S' can be a linker, e.g., a cleavable linker coupled to a solid support or an affinity ligand;
  X and Y can be each a bond, wherein X can couple an atom or an optional substituent of each of RP and LK to thereby link RP to LK and Y can couple an atom or an optional substituent of LK to RG;
  RP and LK can be each optionally and independently substituted, wherein
    RP and LK can be each independently a heteroaryl or heterocycloalkyl, or a linear or branched aliphatic or heteroaliphatic group substituted or interrupted with a heteroaryl or heterocycloalkyl; or
    LK can be a linking moiety and RP can be a tertiary amine, a 4-9 membered nitrogenous heteroaryl or heterocycloalkyl bonded at a ring nitrogen to X, a 5-6 membered arylmethylene, a 5-6 membered heteroarylmethylene, or a 5-6 membered heterocycloalkyl.

In some embodiments, the above values can be subject to one or more provisios selected from: 1) RP—X-LK—Y— is not a polymer; 2) RP and LK do not both comprise piperazinyl; RP and LK are not both selected from the group consisting of amino acids (such as naturally occurring amino acids), nucleotides, oligonucleotides, peptides, and proteins; and 3) when t is 0, the group RP is not an optionally substituted 5, 6 or 7 membered heterocycloalkyl comprising a ring nitrogen atom that is N-alkylated with a substituted or unsubstituted moiety of the formula —C(J)$_2$-LK'— such that LK' is —C(O)—, —C(S)—, —C(NH)—, or —C(NRz)-, wherein Rz is an alkyl group comprising one to eight carbon atoms which may optionally contain a heteroatom or optionally substituted aryl group wherein the carbon atoms of the alkyl and aryl groups independently comprise linked hydrogen, deuterium and/or fluorine atoms and each J is the same or different and is H, deuterium (ID), Rz, ORz, SRz, NHRz, N(Rz)$_2$, fluorine, chlorine, bromine or iodine.

In various embodiments, RG can be a nucleophilic group or an electrophilic group represented by RG, and each compound can be a labeling reagent; and a plurality of the compounds can be a labeling reagent kit, a library of labeling reagents, or the like.

In some embodiments, RG can refer to the reaction product of an analyte with the nucleophilic groups or electrophilic groups defined for RG, wherein each compound can be a labeled analyte. A plurality of such compounds can be a mixture of labeled analytes, a library of labeled analytes, and the like. For precision of reference in certain depictions of such embodiments, the reaction product of an analyte with the nucleophilic groups or electrophilic groups defined for RG is represented by—Analyte.

Some embodiments can be a single isotopically enriched compound represented by Structural Formulas $I^w$ or $I^\#$. In various embodiments, a plurality of compounds can be isotopically enriched. A compound that is isotopically enriched can be enriched in one, two, three, four, five, six, seven, eight, nine, ten, eleven, twelve, up to fifteen, up to twenty, up to twenty five, or more of the same or different heavy atom isotopes.

Some embodiments can include a plurality of different compounds, e.g. two or more, wherein the plurality of compounds can be, for example, a kit, a library, an array, a mixture, and the like. In such embodiments, RP and LK can each have a unique gross mass for each different compound that can compensate for the difference in unique gross mass between the RP for each compound such that the aggregate gross mass of the RP and LK for each compound can be the same. In some embodiments, two or more different compounds can be isobaric isomers, wherein the compounds have isomeric chemical structures but the same gross mass. In some embodiments, two or different compounds can be isobaric isotopologues, wherein the compounds have the same chemical structure and same gross mass but different isotopic compositions, e.g., at least one isobaric isotopologues is isotopically enriched.

In various embodiments, one of r and t can be 1, and S' can be a cleavable linker coupled to a solid support or an affinity ligand. Thus, when S' is a solid support, various embodiments can include solid supported libraries of labeling reagents, solid supported libraries of labeled analytes, and the like.

In some embodiments, for each different compound, the cleavable linker represented by S' can be coupled to the solid support at a separate array location on the solid support, the solid support comprising polystyrene, polyethylene, polypropylene, polyfluoroethylene, polyethyleneoxy, polyacrylamide, glass, silica, controlled-pore-glass (CPG), or reverse phase silica, the substrate in the form of a gel, a membrane or a surface, whereby the kit is an array library of the different compounds. In some embodiments, RG can be a nucleophilic group or an electrophilic group, whereby the kit is an array library of labeling reagents; or RG can be a reaction product of an analyte with a nucleophilic group or an electrophilic group; whereby the kit is an array library of labeled analytes.

In some embodiments, for each different compound, the cleavable linker represented by S' can be coupled to the solid support at a separate solid support bead, sphere, particle, or granule, the solid support comprising polystyrene, polyethylene, polypropylene, polyfluoroethylene, polyethyleneoxy, polyacrylamide, glass, silica, controlled-pore-glass (CPG), or reverse phase silica, whereby the kit is a solid support library of the different compounds. In some embodiments, RG can be a nucleophilic group or an electrophilic group, whereby the kit is a solid support library of labeling reagents; or RG can be a reaction product of an analyte with a nucleophilic group or an electrophilic group; whereby the kit is a solid support library of labeled analytes.

In some embodiments, for each different compound, the cleavable linker represented by S' can be coupled to a different affinity ligand selected from the group consisting of an antigen, an antibody, an antibody fragment, an avidin, biotin, streptavidin, a protein A, a lectin, and a carbohydrate, whereby the kit is an affinity ligand library. In some embodiments, RG can be a nucleophilic group or an electrophilic group, whereby the kit is an affinity ligand library of labeling reagents; or RG can be a reaction product of an analyte with a nucleophilic group or an electrophilic group; whereby the kit is an affinity ligand library of labeled analytes.

In various embodiments, compounds in the kits, arrays, libraries, labeled analyte mixtures, and methods, and the isotopically enriched compound can be further represented by one of Structural Formulas I-S' to VI-S' or I to VI:

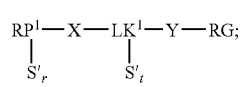  I-S'

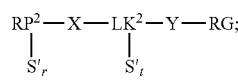  II-S'

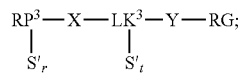  III-S'

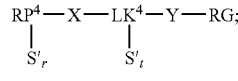  IV-S'

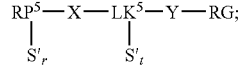  V-S'

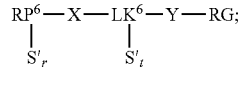  VI-S'

  I

  II

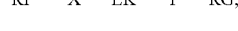  III

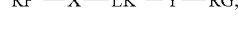  IV

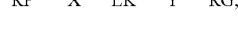  V

  VI or isotopologues thereof. The variables r, s, S', X, and X are as described above or as further detailed below and can be subject to the corresponding provisos above. The variables $RP^1$, $RP^2$, $RP^3$, $RP^4$, $RP^5$, $RP^6$, $LK^1$, $LK^2$, $LK^3$, $LK^4$, $LK^5$, and $LK^6$ are as described in greater detail below and can be subject to the corresponding provisos above for RP—X-LK—Y— and its variables RP/RP' and LK/LK'.

For example, for compounds that can be represented by structural formula V or V-S', $LK^5$ can be a linking moiety represented by structural formula E (it will be understood that the points of attachment to the remainder of the labeling reagent are identified in the structure by the wavy line):

$$RP^5\text{—X-}LK^5\text{—Y—RG} \qquad V$$

wherein:
$RP^5$ can be the reporter group RP (as defined above) and $LK^5$ can be a linking moiety represented by structural formula E:

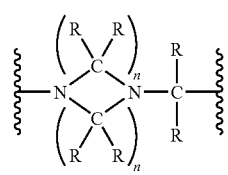  E wherein each n, independently, can be an integer from 1 to 3; and
each R, independently, can be H, D, an alkyl, a heteroalkyl, an aryl, a heteroaryl, or a halo group.

In various embodiments, at least one compound can be represented by structural formula D:

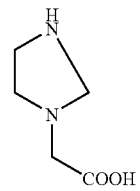  D

In another example, for compounds that can be represented by structural formula I or I-S', $RP^1$ can be a reporter group represented by structural formula A (it will be understood that the point of attachment to the remainder of the labeling reagent is identified in the structure by the wavy line):

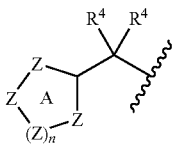  A

Ring A can be aromatic;
each Z can be independently CH, $CR^2$, or N, provided that no more than two Z groups are N;
n can be 1 or 2, typically 2 so that Ring A is a six membered ring;
each $R^2$ can be independently selected from the suitable substituents described in the Definitions, or more typically, can be selected from hydrogen, deuterium, —OH, halogen, —CN, —NO$_2$, alkyl, alkenyl, alkynyl, aryl, heteroaryl, arylalkyl, heteroarylalkyl, heteroalkyl, heterocycloalkyl, —R³, or -T-R³;

each R³ can be independently hydrogen, deuterium, alkyl, alkenyl, alkynyl, aryl, arylalkyl, heteroalkyl, heterocycloalkyl, heteroaryl, or heteroaralkyl;

T can be —O—, —NR⁴—, —S—, —C(O)—, —S(O)—, —SO₂—, —NR⁴C(O)—, —C(O)NR⁴—, —NR⁴SO₂—, —SO₂NR⁴—, —C(O)O—, —OC(O)—, —NR⁴C(O)O—, or —OC(O)NR⁴—;

each R⁴ is independently hydrogen, deuterium, alkyl, heteroalkyl, aryl, or aralkyl;

LK¹ is a linking moiety;

X is a bond between an atom of the reporter and LK¹; and

Y is a bond between an atom of the linker and an atom of RG.

In various embodiments, at least one of RP¹ and LK¹ can be isotopically enriched with one or more heavy atom isotopes, for example, RP¹. In some embodiments, both RP¹ and LK¹ can each be isotopically enriched with one or more heavy atom isotopes. In some embodiments, each of RP¹ and LK¹ comprise at least two heavy atom isotopes. In some embodiments, each of RP¹ and LK¹ each comprise at least three heavy atom isotopes.

In some embodiments, n is 2 whereby Ring A can be a six membered ring. In some embodiments, either of the Z groups in the ortho or para positions of Ring A can be C-T-R³. In various embodiments, either of the Z groups in the ortho or para positions of Ring A can be C—NHC(O)—R³ or C—NHSO₂—R³ and each R³ can be independently an optionally substituted alkyl group. In some embodiments, n is 2 and each Z is independently CH or CR², and thus RP¹ can be represented by Structural Formula A-1:

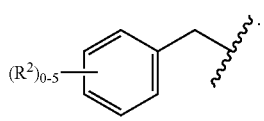

A-1

In some embodiments, at least one atom in formula A is isotopically enriched with a heavy atom isotope.

In some embodiments, LK¹ can comprise an amino acid, peptide, a C₁₋₁₂ alkylene chain wherein 1-4 methylene units of said chain are independently replaced by an amino acid, —O—, —NR—, —S—, —C(O)—, —S(O)—, —SO₂—, —NRC(O)—, —C(O)NR—, —NRSO₂—, —SO₂NR—, —C(O)O—, —OC(O)—, —NRC(O)O—, —OC(O)NR—, or an arylene, arylalkylene, heteroalkylene, heterocycloalkylene, heteroarylene, or heteroaralkylene, wherein each R is independently hydrogen, deuterium, or an optionally substituted C₁₋₆ alkyl group. The amino acid moiety can be a glycine, aspartic acid, serine, cysteine, lysine, proline, or ornithine.

In some embodiments, LK¹ can be an optionally substituted C₁₋₁₂ alkylene chain wherein 1-4 methylene units of said chain can be independently replaced by —C(O)O—, —C(O)—, —O—, —NH—, —C(O)NH—, —S—, —NH—, —S(O)—, —SO₂—, or an amino acid, wherein the methylene unit α to group A can be replaced by —O—, —S—, or —NH—.

In some embodiments, one of the methylene units of LK¹ can be replaced by an optionally substituted azaalkylene, azacycloalkylene, or azaarylene.

In various embodiments, at least one compound can be represented by structural formula I-1:

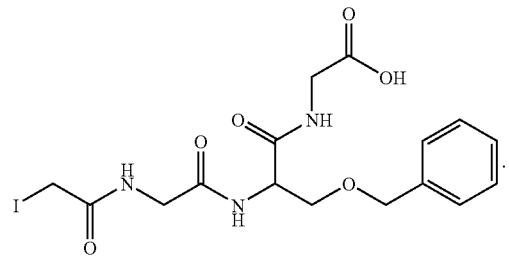

I-1

In various embodiments, at least one compound can be represented by a structural formula selected from:

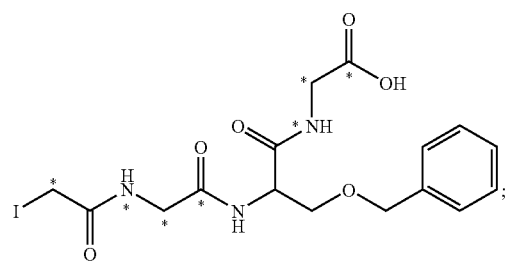

I-2

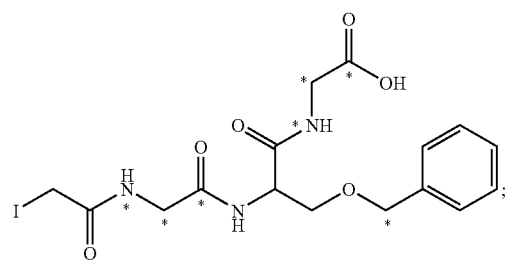

I-3

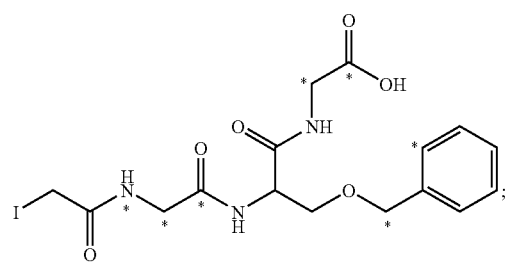

I-4

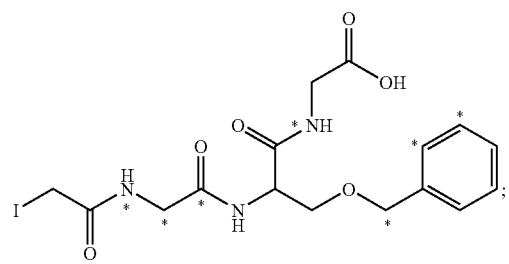

I-5

-continued

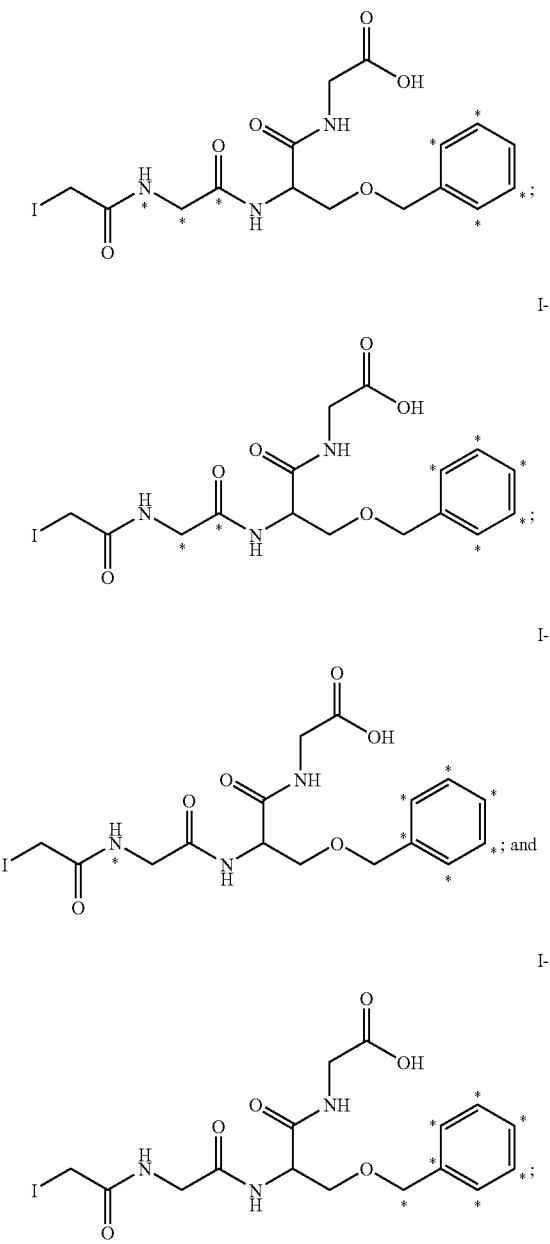

wherein the symbol "*" next to a carbon atom can indicate that the carbon can be a $^{13}C$ isotope and the symbol "*" next to a nitrogen atom can indicates that the nitrogen can be a $^{15}N$ isotope.

In some embodiments, at least one compound can be represented by structural formula I-1:

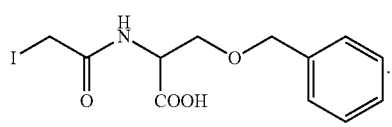

In some embodiments, at least one compound can be represented by a structural formula selected from:

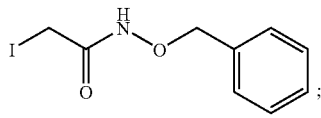

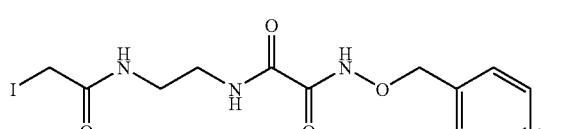

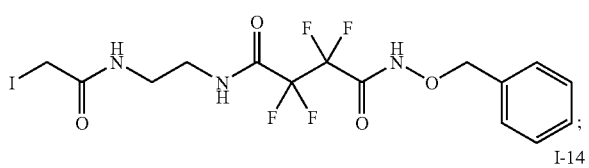

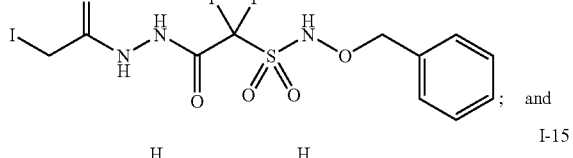

In various embodiments, at least one compound can be represented by a structural formula selected from:

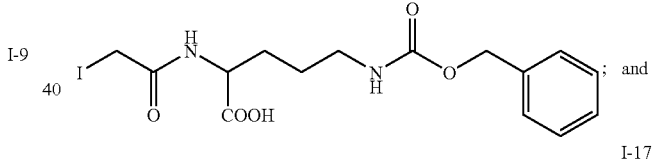

wherein $R^8$ can be a valence bond, an alkylene, or $-(CH_2)_s-(O-CH_2CH_2)_p-(CH_2)_s-$; p can be 1, 2, 3, or 4; and each s can be independently 0, 1, 2, or 3.

In some embodiments, the compound can be represented by structural formula II or II-S', wherein $RP^2$ can be a reporter group represented by structural formula B

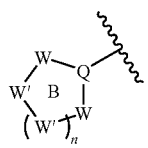

Ring B can be non-aromatic;
n can be 1 or 2;
each W can be independently O, S, or $NR^4$; in some embodiments, each W in structural formula II can be O or an isotope thereof;

each W' can be independently CH$_2$, CHR$^2$, C(R$^2$)$_2$, C(O), S(O), S(O)$_2$, or C=N—R$^4$;

Q can be CH or CR$^2$;

each R$^2$ can be independently selected from the suitable substituents described in the Definitions, or more typically, can be selected from hydrogen, deuterium, —OH, halogen, —CN, —NO$_2$, alkyl, alkenyl, alkynyl, aryl, heteroaryl, arylalkyl, heteroarylalkyl, heteroalkyl, heterocycloalkyl, —R$^3$, or -T-R$^3$;

each R$^3$ can be independently hydrogen, deuterium, or optionally substituted alkyl, alkenyl, alkynyl, aryl, arylalkyl, heteroalkyl, heterocycloalkyl, heteroaryl, or heteroaralkyl;

T can be —O—, —NR$^4$—, —S—, —C(O)—, —S(O)—, —SO$_2$—, —NR$^4$C(O)—, —C(O)NR$^4$—, —NR$^4$SO$_2$—, —SO$_2$NR$^4$—, —C(O)O—, —OC(O)—, —NR$^4$C(O)O—, or —OC(O)NR$^4$—;

each R$^4$ can be independently hydrogen, deuterium, an alkyl, a heteroalkyl, an aryl, or an aralkyl;

LK$^2$ can be a linking moiety;

X can be a bond between an atom of the reporter and LK$^2$; and

Y can be a bond between an atom of the linker and an atom of RG.

In some embodiments, at least one W moiety is O and at least one W' moiety is CHR$^2$.

In various embodiments, at least one of RP$^2$ and LK$^2$ can be isotopically enriched with one or more heavy atom isotopes, for example, RP$^2$. In some embodiments, both RP$^2$ and LK$^2$ can each be isotopically enriched with one or more heavy atom isotopes. In some embodiments, each of RP$^2$ and LK$^2$ comprise at least two heavy atom isotopes. In some embodiments, each of RP$^2$ and LK$^2$ comprise at least three heavy atom isotopes. In various embodiments, LK$^2$ can be as defined for the various embodiments of LK$^1$.

In some embodiments, the reporter group is of formula B wherein n is 2 and each W is O. Thus, a reporter group of formula B-1 is provided:

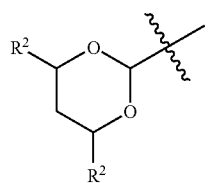

B-1 wherein each R$^2$ is as defined above and herein.

In some embodiments, the reporter group is of formula B wherein n is 1 and each W is O. Thus, a reporter group of formula B-2 is provided:

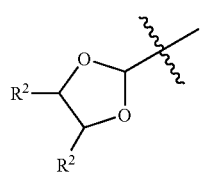

B-2 wherein each R$^2$ is as defined above and herein. In some embodiments, the compound can be represented by structural formula II-d:

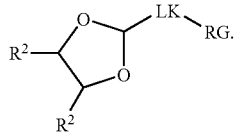

II-d

In some embodiments, the compound can be represented by structural formula II-e:

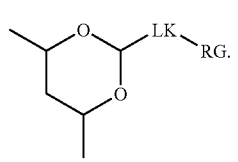

II-e

In some embodiments, at least one atom in RP$^1$ isotopically enriched with a heavy atom isotope.

In various embodiments, the compound can be represented by structural formula III or III-S', wherein RP$^3$ can be a reporter group represented by structural formula C:

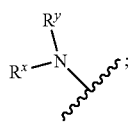

C each of R$^x$ and R$^y$ can be independently alkyl, alkenyl, alkynyl, aryl, heteroaryl, arylalkyl, heteroarylalkyl, or heteroalkyl, wherein suitable optional substituents for R$^x$ and R$^y$ can be independently selected from the suitable substituents described in the Definitions, or more typically, can be selected from hydrogen, deuterium, —OH, halogen, —CN, —NO$_2$, alkyl, alkenyl, alkynyl, aryl, heteroaryl, arylalkyl, heteroarylalkyl, heteroalkyl, heterocycloalkyl, —R$^3$, -T-R$^3$, ribose, deoxyribose or phosphate, or R$^x$ and R$^y$ can be taken together to form Ring C':

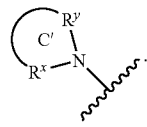

Ring C' can be optionally substituted heteroaryl or heterocycloalkyl, wherein suitable optional substituents for Ring C can be independently selected from the suitable substituents described in the Definitions, or more typically, can be selected from hydrogen, deuterium, —OH, halogen, —CN, —NO$_2$, alkyl, alkenyl, alkynyl, aryl, heteroaryl, arylalkyl, heteroarylalkyl, heteroalkyl, heterocycloalkyl, —R$^3$, -T-R$^3$, ribose, deoxyribose or phosphate;

each R$^3$ can be independently hydrogen, deuterium, alkyl, alkenyl, alkynyl, aryl, arylalkyl, heteroalkyl, heterocycloalkyl, heteroaryl, or heteroaralkyl;

T can be —O—, —NR$^4$—, —S—, —C(O)—, —S(O)—, —SO$_2$—, —NR$^4$C(O)—, —C(O)NR$^4$—, —NR⁴SO₂—, —SO₂NR⁴—, —C(O)O—, —OC(O)—, —NR⁴C(O)O—, or —OC(O)NR⁴—;

each R⁴ can be independently hydrogen, deuterium, alkyl, heteroalkyl, aryl, or aralkyl;

LK³ can be a linking moiety, provided that when R^x and R^y are taken together to form Ring C', then the ring nitrogen that links R^x and R^y is linked to a group other than a substituted or unsubstituted moiety of the formula —C(J)₂-LK'— such that LK' is —C(O)—, —C(S)—, —C(NH)—, or —C(NRz)-, wherein Rz is an alkyl group comprising one to eight carbon atoms which may optionally contain a heteroatom or optionally substituted aryl group wherein the carbon atoms of the alkyl and aryl groups independently comprise linked hydrogen, deuterium and/or fluorine atoms and J is the same or different and is H, deuterium (D), Rz, ORz, SRz, NHRz, N(Rz)₂, fluorine, chlorine, bromine or iodine;

X can be a bond between an atom of the reporter and LK³; and

Y can be a bond between an atom of the linker and an atom of RG.

In various embodiments, at least one of RP³ and LK³ can be isotopically enriched with one or more heavy atom isotopes, for example, RP³. In some embodiments, both RP³ and LK³ can each be isotopically enriched with one or more heavy atom isotopes. In some embodiments, each of RP³ and LK³ comprise at least two heavy atom isotopes. In some embodiments, each of RP³ and LK³ each comprise at least three heavy atom isotopes.

In some embodiments, LK³ is a linking moiety subject to the proviso that when R^x and R^y are taken together to form Ring C, then LK can be other than —C(J)₂C(O)—, —C(J)₂C(S)—, —C(J)₂=NH—, or —C(J)₂=NR⁴—, wherein each J can be independently hydrogen, deuterium, R⁴, OR⁴, SR⁴, NHR⁴ or N(R⁴)₂. In various embodiments, LK³ can be as defined for the various embodiments of LK¹.

In some embodiments, the reporter group is of formula C wherein R^x and R^y are taken together to form Ring C'. Thus, a reporter group of formula C'' is provided:

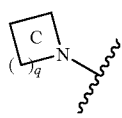

C'' wherein q is 0-6 and Ring C is as defined as above and herein.

In some embodiments, the reporter group can be represented by C wherein Ring C'' is heterocycloalkyl and q is 2, 3 or 4. Thus, a reporter group of formula C-1 is provided:

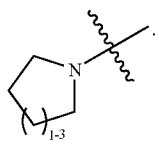

In some embodiments, at least one atom in formula C-1 is isotopically enriched with a heavy atom isotope. Is some embodiments, at least one atom in formula C-1 is isotopically enriched with two heavy atom isotopes.

In some embodiments, the above-described structures for the reporter group C require that the linker not be a substituted or unsubstituted acetic acid moiety that is N-alkylated to the nitrogen atom through bond X.

In some embodiments, the compound can be represented by structural formula III-c:

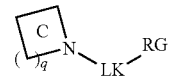

III-c wherein q can be an integer from 0 to 6 and LK can contain a carbonyl.

In some embodiments, the compound can be represented by a structural formula selected from:

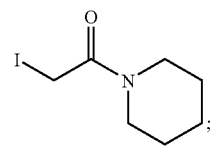

III-1

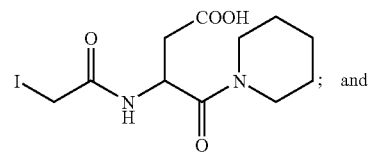

III-2

; and

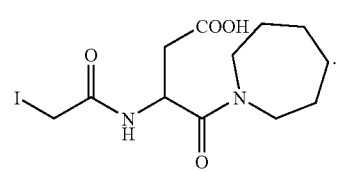

III-3

In various embodiments, RP can comprise an optionally substituted piperazinyl and LK can be an aryl or cycloalkyl, or a linear or branched aliphatic or heteroaliphatic group substituted or interrupted with an aryl or cycloalkyl.

Also, for compounds that can be represented by structural formula VI or VI-S', at least one of RP⁶ or LK⁶ can comprises an optionally substituted nucleobase, or a linear or branched aliphatic or heteroaliphatic group substituted or interrupted with an optionally substituted nucleobase;

optional substituents for RP⁶ and LK⁶ can be independently selected from hydrogen, deuterium, —OH, halogen, —CN, —NO₂, alkyl, alkenyl, alkynyl, aryl, heteroaryl, arylalkyl, heteroarylalkyl, heteroalkyl, heterocycloalkyl, —R³, -T-R³, ribose, deoxyribose, or phosphate;

each R³ can be independently hydrogen, deuterium, alkyl, alkenyl, alkynyl, aryl, arylalkyl, heteroalkyl, heterocycloalkyl, heteroaryl, or heteroaralkyl;

T can be —O—, —NR⁴—, —S—, —C(O)—, —S(O)—, —SO₂—, —NR⁴C(O)—, —C(O)NR⁴—, —NR⁴SO₂—, —SO₂NR⁴—, —C(O)O—, —OC(O)—, —NR⁴C(O)O—, or —OC(O)NR⁴—;

each R⁴ can be independently hydrogen, deuterium, alkyl, heteroalkyl, aryl, or aralkyl;

X is a bond between an atom of the reporter and LK⁶; and

Y is a bond between an atom of the linker and an atom of RG, wherein at least one of RP⁶ and LK⁶ can be isotopically enriched with one or more heavy atom isotopes;

provided that if RP⁶ is a heterocycloalkyl, the heterocycloalkyl is not a 5, 6 or 7 membered heterocycloalkyl comprising a ring nitrogen atom that is N-alkylated with a substituted or unsubstituted moiety of the formula —C(J)₂-LK' such that LK' is —C(O)—, —C(S)—, —C(NH)—, or —C(NRz)-, wherein Rz is an alkyl group comprising one to eight carbon atoms which may optionally contain a heteroatom or optionally substituted aryl group wherein the carbon atoms of the alkyl and aryl groups independently comprise linked hydrogen, deuterium and/or fluorine atoms and J is the same or different and is H, deuterium (D), Rz, ORz, SRz, NHRz, N(Rz)₂, fluorine, chlorine, bromine or iodine.

Also, for compounds that can be represented by structural formula IV or IV-S', RP⁴ and LK⁴ can be each independently a heteroaryl or heterocycloalkyl, or a linear or branched aliphatic or heteroaliphatic group substituted or interrupted with a heteroaryl or heterocycloalkyl, wherein suitable optional substituents for RP⁴ and LK⁴ can be independently selected from the suitable substituents described in the Definitions, or more typically, can be selected from hydrogen, deuterium, —OH, halogen, —CN, —NO₂, alkyl, alkenyl, alkynyl, aryl, heteroaryl, arylalkyl, heteroarylalkyl, heteroalkyl, heterocycloalkyl, —R³, -T-R³, ribose, deoxyribose or phosphate;

each R³ can be independently hydrogen, deuterium, alkyl, alkenyl, alkynyl, aryl, arylalkyl, heteroalkyl, heterocycloalkyl, heteroaryl, or heteroaralkyl;

T can be —O—, —NR⁴—, —S—, —C(O)—, —S(O)—, —SO₂—, —NR⁴C(O)—, —C(O)NR⁴—, —NR⁴SO₂—, —SO₂NR⁴—, —C(O)O—, —OC(O)—, —NR⁴C(O)O—, or —OC(O)NR⁴—;

each R⁴ can be independently hydrogen, deuterium, alkyl, aryl, or aralkyl;

X can be a bond between an atom of the reporter and LK⁴; and

Y can be a bond between an atom of the linker and an atom of RG.

In various embodiments, at least one of RP⁴ and LK⁴ can be isotopically enriched with one or more heavy atom isotopes, for example, RP⁴. In some embodiments, both RP⁴ and LK⁴ can each be isotopically enriched with one or more heavy atom isotopes. In some embodiments, each of RP⁴ and LK⁴ comprise at least two heavy atom isotopes. In some embodiments, each of RP⁴ and LK⁴ each comprise at least three heavy atom isotopes.

In various embodiments, the heteroaryl or heterocycloalkyl groups in RP⁴ and LK⁴ can be each independently selected from optionally substituted imidazolyl, furyl, pyrrolyl, thienyl, oxazolyl, thiazolyl, isoxazolyl, isothiazolyl, thiadiazolyl, oxadiazolyl, pyridinyl, pyrimidyl, pyrazinyl, pyridazinyl, quinolyl, isoquinolinyl, indazolyl, benzoxazolyl, benzisooxazolyl, benzofuryl, benzothiazolyl, indolizinyl, imidazopyridinyl, pyrazolyl, triazolyl, isothiazolyl, oxazolyl, tetrazolyl, benzimidazolyl, benzothiazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl, benzo(b)thienyl, morpholinyl, piperidinyl, piperazinyl, pyrrolidinyl, and thiomorpholinyl.

In various embodiments, at least one of RP⁴ or LK⁴ can comprise an optionally substituted piperazinyl, or a linear or branched aliphatic or heteroaliphatic group substituted or interrupted with piperazinyl, or in some embodiments, RP⁴ can be an optionally substituted piperazinyl, for example, N-methyl piperazinyl.

In various embodiments, at least one of RP⁴ or LK⁴ can comprise an optionally substituted nucleobase (e.g., optionally substituted purinyl or pyrimidinyl), or a linear or branched aliphatic or heteroaliphatic group substituted or interrupted with an optionally substituted nucleobase. In some embodiments, LK⁴ can be an optionally substituted nucleobase, or a linear or branched aliphatic or heteroaliphatic group substituted or interrupted with an optionally substituted nucleobase.

The nucleobases, e.g. the nucleobase in LK⁴ can be an optionally substituted 9H-purin-6-amine, 2-amino-1H-purin-6(9H)-one, 4-aminopyrimidin-2(1H)-one, 5-methylpyrimidine-2,4(1H,3H)-dione, or the like. The nucleobase can be substituted or unsubstituted.

In various embodiments, the compound can be represented by a structural formula selected from:

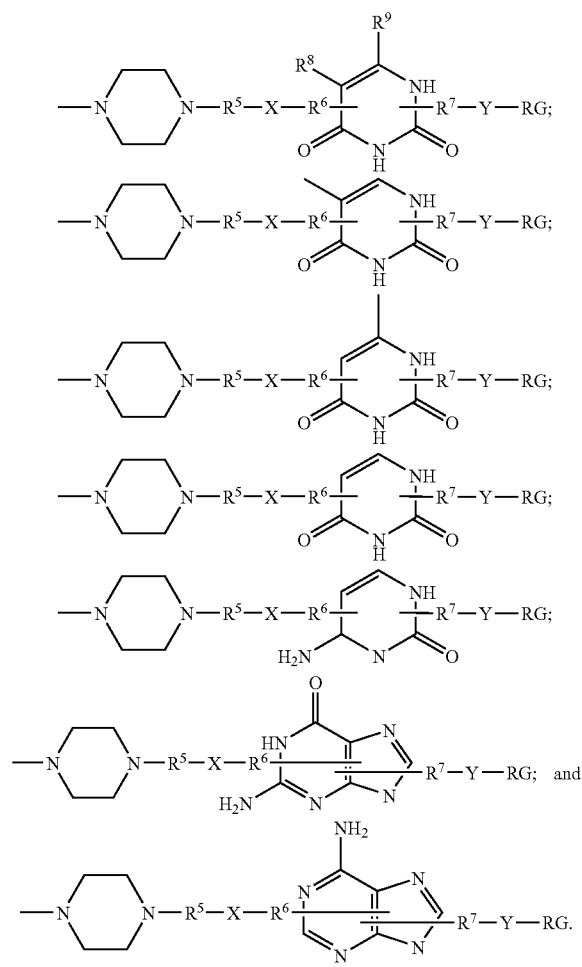

A bond drawn across a ring, as above, indicates that the bond can be attached to any substitutable atom in that ring; a bond drawn across two rings can be attached to any substitutable atom in either of those two rings.

The group R⁵ can be —C(J)₂-C(O)—, —C(J)₂-C(S)—, —C(J)(NH)—, or —C(J)₂-C(NRᶻ)—, wherein Rᶻ is an alkyl group comprising one to eight carbon atoms that may optionally contain a heteroatom or optionally substituted aryl group wherein the carbon atoms of the alkyl and aryl groups independently comprise linked hydrogen, deuterium and/or fluorine atoms; and each J is the same or different and is H, deuterium (D), Rz, ORz, SRz, NHRz, N(Rz)$_2$, fluorine, chlorine, bromine or iodine.

R$^6$ and R$^7$ can each independently be alkyl, alkenyl, alkynyl, aryl, heteroaryl, arylalkyl, heteroarylalkyl, heteroalkyl, heterocycloalkyl, —R$^3$, -T-R$^3$, ribose, deoxyribose, or phosphate, wherein each R$^3$ is independently hydrogen, deuterium, alkyl, alkenyl, alkynyl, aryl, arylalkyl, heteroalkyl, heterocycloalkyl, heteroaryl, or heteroaralkyl.

R$^8$ and R$^9$ can each independently be H, deuterium (D), fluorine, chlorine, bromine, iodine, or a halogenated alkyl (e.g., a CF$_3$ group).

In some embodiments, the compound can be:

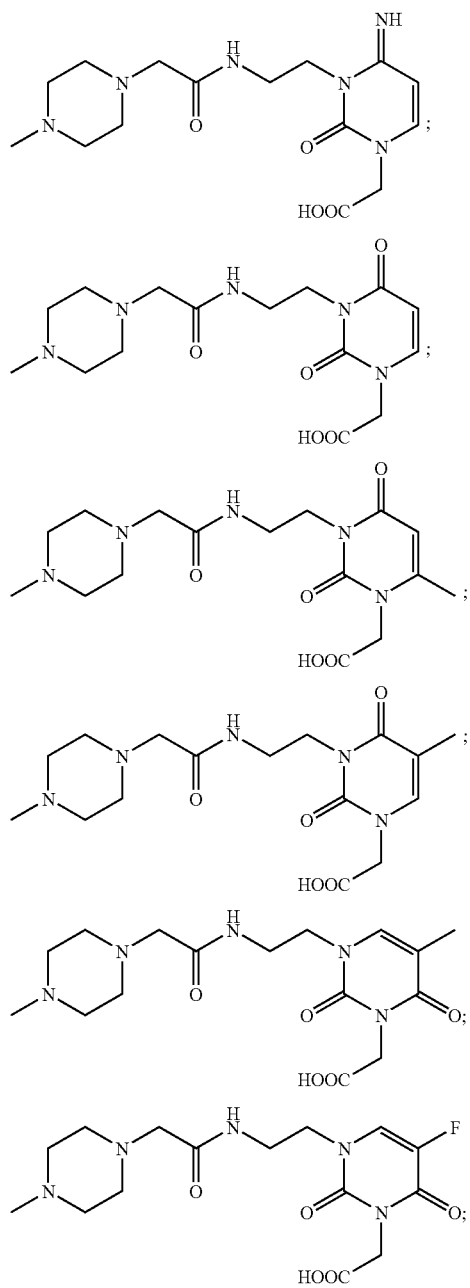

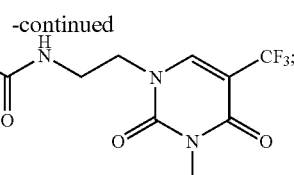

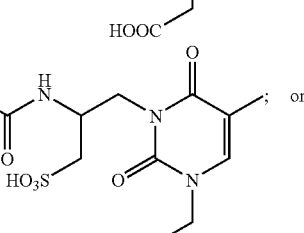

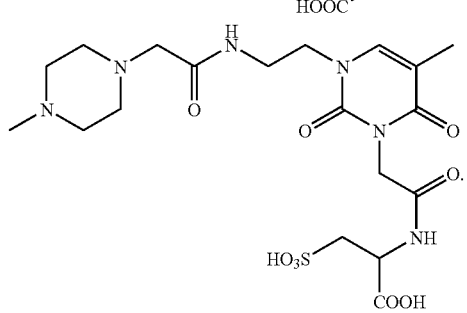

B. Methods

According to the methods of this invention, the analyte to be determined can be labeled by reacting the analyte with a disclosed compound, e.g., the compounds as represented by one of Structural Formulas I-S' to IV-S' or I to IV, wherein RG is a reactive group that is a nucleophilic group or electrophilic group. The labeled analyte, the analyte itself, one or more fragments of the analyte and/or fragments of the label, can be determined by mass analysis. In some embodiments, methods of this invention can be used for the analysis of different analytes in the same sample as well as for the multiplex analysis of the same and/or different analytes in two or more different samples. The two or more samples can be mixed to form a sample mixture. In the multiplex analysis, labeling reagents can be used to determine from which sample of a sample mixture an analyte originated. The absolute and/or relative (with respect to the same analyte in different samples) amount (often expressed in concentration or quantity) of the analyte, in each of two or more of the samples combined to form the sample mixture, can be determined. Moreover, the mass analysis of fragments of the analyte (e.g. daughter fragment ions) can be used to identify the analyte and/or the precursor to the analyte; such as where the precursor molecule to the analyte was degraded.

One distinction of the described approach lies in the fact that analytes from different samples can be differentially isotopically labeled (i.e. isotopically coded) with unique labels that are chemically isomeric or isobaric (have equal mass) and that identify the sample from which the analyte originated. The differentially labeled analytes are not distinguished in MS mode of a mass spectrometer because they all have identical (gross) mass to charge ratios. However, when subjected to dissociative energy levels, such as through collision induced dissociation (CID), the labels can fragment to yield unique reporters that can be resolved by mass (mass to charge ratio) in a mass spectrometer. The relative amount of reporter observed in the mass spectrum can correlate with the relative amount of a labeled analyte in the sample mixture and, by implication, the amount of that analyte in a sample from which it originated. Thus, the relative intensities of the reporters (i.e. signature ions) can be used to measure the relative amount of an analyte or analytes in two or more different samples that were combined to form a sample mixture. From the reporter information, absolute amounts (often expressed as concentration and/or quantity) of an analyte or analytes in two or more samples can be derived if calibration standards for the each analyte, for which absolute quantification is desired, are incorporated into the sample mixture.

For example, the analyte might be a peptide that resulted from the degradation of a protein using an enzymatic digestion reaction to process the sample. Protein degradation can be accomplished by treatment of the sample with a proteolytic enzyme (e.g. trypsin, papain, pepsin, ArgC, LysC, V8 protease, AspN, pronase, chymotrypsin or carboxypeptidase C). By determination of the identity and amount of a peptide in a sample mixture and identifying the sample from which it originated, optionally coupled with the determination of other peptides from that sample, the precursor protein to the degraded peptide can be identified and/or quantified with respect to the sample from which it originated. Because this method allows for the multiplex determination of a protein, or proteins, in more than one sample (i.e. from a sample mixture), it is a multiplex method.

In some embodiments, this invention pertains to a method comprising reacting each of two or more samples, each sample containing one or more reactive analytes, with a different labeling reagent of a set of labeling reagents wherein the different labeling reagents of the set each comprise the formula: RP—X-LK—Y—RG. Consequently, one or more analytes of each sample are labeled with the moiety "RP—X-LK—Y—" by reaction of a nucleophilic group or electrophilic group of the analyte with the electrophilic or nucleophilic reactive group (RG), respectively, of the different labeling reagents. The labeling process can produce two or more differentially labeled samples each comprising one or more labeled analytes. The labeling reagents of the set can be isomeric or isobaric. The reporter of each labeling reagent can be identified with, and therefore used to identify, the sample from which each labeled analyte originated.

RG is a reactive group the characteristics of which have been previously described. RP is a reporter moiety the characteristics of which have been previously described. The gross mass of each reporter can be different for each reagent of the set. LK is a linker moiety the characteristics of which have been previously described. The gross mass of the linker can compensate for the difference in gross mass between the reporters for the different labeling reagents such that the aggregate gross mass of the reporter-linker combination is the same for each reagent of the set. X is a bond between an atom of the reporter and an atom of the linker. Y is a bond between an atom of the linker and an atom of the reactive group (or after reaction with an analyte, Y is a bond between the an atom of the linker and an atom of the analyte). Bonds X and Y fragment in at least a portion of the labeled analytes when subjected to dissociative energy levels in a mass spectrometer. The characteristics of bonds X and Y have been previously described.

Once the analytes of each sample are labeled with the labeling reagent that is unique to that sample, the two or more differentially labeled samples, or a portion thereof, can be mixed to produce a sample mixture. Where quantitation is desired, the volume and/or quantity of each sample combined to produce the sample mixture can be recorded. The volume and/or quantity of each sample, relative to the total sample volume and/or quantity of the sample mixture, can be used to determine the ratio necessary for determining the amount (often expressed in concentration and/or quantity) of an identified analyte in each sample from the analysis of the sample mixture. The sample mixture can therefore comprise a complex mixture wherein relative amounts of the same and/or different analytes can be identified and/or quantitated, either by relative quantitation of the amounts of analyte in each of the two or more samples or absolutely where a calibration standard is also added to the sample mixture.

The mixture can then be subjected to spectrometry techniques wherein a first mass analysis can be performed on the sample mixture, or fraction thereof, using a first mass analyzer. Ions of a particular mass to charge ratio from the first mass analysis can then be selected. The selected ions can then be subjected to dissociative energy levels (e.g. collision-induced dissociation (CID)) to thereby induce fragmentation of the selected ions. By subjecting the selected ions, of a particular mass to charge ratio, of the labeled analytes to dissociative energy levels, bonds X and/or Y can be fragmented in at least a portion of the selected ions. Fragmentation of both bonds X and Y can cause fragmentation of the reporter-linker moiety as well as cause release the charged or ionized reporter from the analyte. Ions subjected to dissociative energy levels can also cause fragmentation of the analyte to thereby produce daughter fragment ions of the analyte. The ions (remaining selected ions, daughter fragment ions and charged or ionized reporters), or a fraction thereof, can then be directed to a second mass analyzer.

A second mass analysis can be performed on the selected ions, and the fragments thereof. The second mass analysis can determine the gross mass (or m/z) and relative amount of each unique reporter that is present at the selected mass to charge ratio as well as the gross mass of the daughter fragment ions of at least one reactive analyte of the sample mixture. For each analyte present at the selected mass to charge ratio, the daughter fragment ions can be used to identify the analyte or analytes present at the selected mass to charge ratio. For example, this analysis can be done as previously described in the section entitled: "Analyte Determination By Computer Assisted Database Analysis".

In some embodiments, certain steps of the process can be repeated one or more times. For example, in some embodiments, ions of a selected mass to charge ratio from the first mass spectrometric analysis, different from any previously selected mass to charge ratio, can be treated to dissociative energy levels to thereby form ionized reporter moieties and ionized daughter fragment ions of at least some of the selected ions, as previously described. A second mass analysis of the selected ions, the ionized reporter moieties and the daughter fragment ions, or a fraction thereof, can be performed. The gross mass and relative amount of each reporter moiety in the second mass analysis and the gross mass of the daughter fragment ions can also be determined. In this way, the information can be made available for identifying and quantifying one or more additional analytes from the first mass analysis.

In some embodiments, the whole process can be repeated one or more times. For example, it may be useful to repeat the process one or more times where the sample mixture has been fractionated (e.g. separated by chromatography or electrophoresis). By repeating the process on each sample, it is possible to analyze all the entire sample mixture. It is contemplated that in some embodiments, the whole process will be repeated one or more times and within each of these repeats, certain steps will also be repeated one or more times such as described above. In this way, the contents of sample mixture can be interrogated and determined to the fullest possible extent.

Those of ordinary skill in the art of mass spectrometry will appreciate that the first and second mass analysis can be performed in a tandem mass spectrometer. Instruments suitable for performing tandem mass analysis have been previously described herein. Although tandem mass spectrometers are preferred, single-stage mass spectrometers may be used. For example, analyte fragmentation may be induced by cone-voltage fragmentation, followed by mass analysis of the resulting fragments using a single-stage quadrupole or time-of-flight mass spectrometer. In other examples, analytes may be subjected to dissociative energy levels using a laser source and the resulting fragments recorded following post-source decay in time-of-flight or tandem time-of-flight (TOF-TOF) mass spectrometers. It is to be understood that in some embodiments, an instrument with a single analyzer can perform both the first and the second mass analysis.

According to the preceding disclosed multiplex methods, in some embodiments, bond X can be more or less prone to, or substantially equal to, fragmentation as compared with fragmentation of bonds of the analyte (e.g. an amide (peptide) bond in a peptide backbone). In some embodiments, bond Y can be more or less prone to fragmentation as compared with fragmentation of bonds of the analyte (e.g. an amide (peptide) bond in a peptide backbone). In some embodiments, the linker for each reagent of the set is neutral in charge after the fragmentation of bonds X and Y (i.e. the linker fragments to produce a neutral loss of mass and is therefore not observed in the MS/MS spectrum). In some embodiments, the position of bonds X and Y does not vary within the labeling reagents of a set, within the labeled analytes of a mixture or within the labeling reagents of a kit. In some embodiments, the reporter for each reagent of the set does not substantially sub-fragment under conditions that are used to fragment the analyte (e.g. an amide (peptide) bond of a peptide backbone). In some embodiments, bond X is less prone to fragmentation as compared with bond Y. In some embodiments, bond Y is less prone to fragmentation as compared with bond X. In some embodiments, bonds X and Y are of approximately the same lability or otherwise are selected such that fragmentation of one of bonds X or Y results in the fragmentation of the other of bonds X or Y.

In some embodiments, the method of the invention comprises: reacting two or more samples, each sample comprising one or more analytes, with a different labeling reagent to thereby produce two or more differently labeled samples each comprising one or more labeled analytes, and mixing two or more of the labeled samples, or a portion thereof, and optionally one or more calibration standards to thereby produce the mixture comprising analytes labeled with the labeling reagents described herein. In some embodiments, each sample used to produce the mixture was labeled with a labeling reagent comprising a unique reporter that can be used to identify the analyte and quantify it relative or absolute amount in the mixture and/or in the sample from which it originated.

In various embodiments, the labeling reagents or "isobaric mass tags" can be represented by any of Structural Formulas $I^w$, $I^\#$, I-S' to IV-S' or I to IV, typically one of I to IV, wherein RG represents a nucleophilic group or an electrophilic group, and the remaining variables are as described above for the compounds.

For example, in some embodiments, the method of the invention comprises reacting two or more samples, each sample comprising one or more reactive analytes, with a set of isobaric mass tags to thereby produce two or more differentially labeled samples each comprising one or more labeled analytes, and mixing two or more of the differentially labeled samples, or a portion thereof, and optionally one or more calibration standards to thereby produce a sample mixture.

Once the labeling reagent is reacted with the reactive analyte, bond Y links the linker to the analyte; at least one of RP (respectively represented by $RP^1$, $RP^2$, $RP^3$, $RP^4$, $RP^5$, and $RP^6$ in the various formula) and LK (respectively represented by $LK^1$, $LK^2$, $LK^3$, $LK^4$, $LK^5$ and $LK^6$ in the various formula) can be isotopically enriched with one or more heavy atom isotopes; upon reaction of the isobaric mass tag with an analyte, each mass tag can add the same mass to the analyte; and upon fragmentation, RP (respectively represented by $RP^1$, $RP^2$, $RP^3$, $RP^4$, $RP^5$ and $RP^6$ in the various formula) of each isobaric mass tag can yield a signature ion having a different mass from the signature ions of the other isobaric mass tags in the set.

According to some embodiments, the analytes from a sample can be reacted with the solid support (each sample being reacted with a different solid support and therefore a different reporter) and the resin bound components of the sample that do not react with the reactive group can be optionally washed away. The labeled analyte or analytes can then be removed from each solid support by treating the support under conditions that cleave the cleavable linker S' and thereby release the reporter-linker-analyte complex from the support. Each support can be similarly treated under conditions that cleave the cleavable linker to thereby obtain two or more different samples, each sample comprising one or more labeled analytes wherein the labeled analytes associated with a particular sample can be identified and/or quantified by the unique reporter linked, thereto. The collected samples can then be mixed to form a sample mixture, as previously described.

For example, each different labeling reagent of the set used in the previously described method can be attached to a solid support.

The support comprising a labeling reagent can be prepared by any of several methods (see the Example section below). In some embodiments, the amino, hydroxyl or thiol group of an isobaric mass tag can be reacted with the cleavable linker of a suitable support. The cleavable linker can be a "sterically hindered cleavable linker". Cleavage of the cleavable linker will release the labeled analyte from the support.

Non-limiting examples of sterically hindered solid supports include: Trityl chloride resin (trityl-Cl, Novabiochem, P/N 01-64-0074), 2-Chlorotrityl chloride resin (Novabiochem, P/N 01-64-0021), DHPP (Bachem, P/N Q-1755), MBHA (Applied Biosystems P/N 400377), 4-methyltrityl chloride resin (Novabiochem, P/N 01-64-0075), 4-methoxytrityl chloride resin (Novabiochem, P/N 01-64-0076), Hydroxy-(2-chorophnyl)methyl-PS (Novabiochem, P/N 01-64-0345), Rink Acid Resin (Novabiochem P/Ns 01-64-0380, 01-64-0202), NovaSyn TGT alcohol resin (Novabiochem, P/N 01-64-0074).

In some embodiments, methods of the invention can further comprise digesting each sample with at least one enzyme to partially, or fully, degrade components of the sample prior to performing the labeling of the analytes of the sample as more fully described above in the section entitled: "Sample Processing". For example, the enzyme can be a protease (to degrade proteins and peptides) or a nuclease (to degrade oligonucleotides). The enzymes may also be used together to thereby degrade sample components. The enzyme can be a proteolytic enzyme such as trypsin, papain, pepsin, ArgC, LysC, V8 protease, AspN, pronase, chymotrypsin or carboxypeptidase C.

In some embodiments, methods can further comprise separating the sample mixture prior to performing the first mass analysis as more fully described above in the section entitled: "Separations". In this manner the first mass analysis can be performed on only a fraction of the sample mixture. The separation can be performed by any separations method, including by chromatography or by electrophoresis. For example, liquid chromatography/mass spectrometry (LC/MS) can be used to effect such a sample separation followed by mass analysis. Moreover, any chromatographic separation process suitable to separate the analytes of interest can be used. Non-limiting examples of suitable chromatographic and electrophoretic separations processes have been described herein.

In still other embodiments, the methods of the invention can comprise both an enzyme treatment to degrade sample components and a separations step.

As described previously, it is possible to determine the analyte associated with the selected ions by analysis of the gross mass of the daughter fragment ions. One such method of determination is described in the section entitled: "Analyte Determination By Computer Assisted Database Analysis".

Once the analyte has been determined, information regarding the gross mass and relative amount of each reporter moiety in the second mass analysis and the gross mass of daughter fragment ions provides the basis to determine other information about the sample mixture. The amount of reporter can be determined by peak intensity in the mass spectrum. In some embodiments, the amount of reporter can be determined by analysis of the peak height or peak width of the reporter (signature ion) signal obtained using the mass spectrometer. Because each sample can be labeled with a different labeling reagent and each labeling reagent can comprise a unique reporter that can be correlated with a particular sample, determination of the different reporters in the second mass analysis identifies the sample from which the ions of the selected analyte originated. Where multiple reporters are found (e.g. according to the multiplex methods of the invention), the relative amount of each reporter can be determined with respect to the other reporters. Because the relative amount of each reporter determined correlates with the relative amount of an analyte in the sample mixture, the relative amount (often expressed as concentration and/or quantity) of the analyte in each sample combined to form the sample mixture can be determined. As appropriate, a correction of peak intensity associated with the reporters can be performed for naturally occurring, or artificially created, isotopic abundance, as previously discussed in the section entitled: "Relative and Absolute Quantitation of Analytes". More specifically, where the volume and/or quantity of each sample that is combined to the sample mixture is known, the relative amount (often expressed as concentration and/or quantity) of the analyte in each sample can be calculated based upon the relative amount of each reporter determined.

This analysis can be repeated one or more times on selected ions of a different mass to charge ratio to thereby obtain the relative amount of one or more additional analytes in each sample combined to form the sample mixture. As appropriate, a correction of peak intensity associated with the reporters can be performed for naturally occurring, or artificially created, isotopic abundance.

Where a calibration standard comprising a unique reporter linked to an analyte, having the selected mass to charge ratio, has been added to the sample mixture in a known amount (often expressed as a concentration and/or quantity), the amount of the unique reporter associated with the calibration standard can be used to determine the absolute amount (often expressed as a concentration and/or quantity) of the analyte in each of the samples combined to form the sample mixture. This is possible because the amount of analyte associated with the reporter for the calibration standard is known and the relative amounts of all other reporters can be determined for the labeled analyte associated with the selected ions. Since the relative amount of reporter, determined for each of the unique reporters (including the reporter for the calibration standard), is proportional to the amount of the analyte associated with each sample combined to form the sample mixture, the absolute amount (often expressed as a concentration and/or quantity) of the analyte in each of the samples can be determined based upon a ratio calculated with respect to the formulation used to produce the sample mixture. As appropriate, a correction of peak intensity associated with the reporters can be performed for naturally occurring, or artificially created, isotopic abundance.

This analysis can be repeated one or more times on selected ions of a different mass to charge ratio to thereby obtain the absolute amount of one or more additional analytes in each sample combined to form the sample mixture. As appropriate, a correction of peak intensity associated with the reporters can be performed for naturally occurring, or artificially created, isotopic abundance.

In some embodiments, the methods can be practiced with digestion and/or separation steps. In some embodiments, the steps of the methods, with or without the digestion and/or separation steps, can be repeated one or more times to thereby identify and/or quantify one or more other analytes in a sample or one or more analytes in each of the two or more samples (including samples labeled with support bound labeling reagents). Depending of whether or not a calibration standard is present in the sample mixture for a particular analyte, the quantitation can be relative to the other labeled analytes, or it can be absolute. Such an analysis method can be particularly useful for proteomic analysis of multiplex samples of a complex nature, especially where a preliminary separation of the labeled analytes (e.g. liquid chromatography or electrophoretic separation) precedes the first mass analysis.

In some embodiments, the analytes can be peptides in a sample or sample mixture. Analysis of the peptides in a sample, or sample mixture, can be used to determine the amount (often expressed as a concentration and/or quantity) of identifiable proteins in the sample or sample mixture wherein proteins in one or more samples can be degraded prior to the first mass analysis. Moreover, the information from different samples can be compared for the purpose of making determinations, such as for the comparison of the effect on the amount of the protein in cells that are incubated with differing concentrations of a substance that may affect, cell growth. Other, non-limiting examples may include comparison of the expressed protein components of diseased and healthy tissue or cell cultures. This may encompass comparison of expressed protein levels in cells, tissues or biological fluids following infection with an infective agent such as a bacteria or virus or other disease states such as cancer. In other examples, changes in protein concentration over time (time-course) studies may be undertaken to examine the effect of drug treatment on the expressed protein component of cells or tissues. In still other examples, the information from different samples taken over time may be used to detect and monitor the concentration of specific proteins in tissues, organs or biological fluids as a result of disease (e.g. cancer) or infection.

In some embodiments, the analyte can be a nucleic acid fragment in a sample or sample mixture. The information on the nucleic acid fragments can be used to determine the amount (often expressed as a concentration and/or quantity)

of identifiable nucleic acid molecules in the sample or sample mixture wherein the sample was degraded prior to the first mass analysis. Moreover, the information from the different samples can be compared for the purpose of making determinations as described above.

C. Mixtures

In some embodiments, this invention pertains to mixtures (e.g. sample mixtures). The mixtures can comprise at least two differentially labeled analytes, wherein each of the two-labeled analytes can originate from a different sample and comprise the formula: RP—X-LK—Y-Analyte. For each different label, some of the labeled analytes of the mixture can be the same and some of the labeled analytes can be different. The atoms, moieties or bonds, X, Y, RP and LK have been previously described and their characteristics disclosed. The mixture can be formed by mixing all, or a part, of the product of two or more labeling reactions wherein each labeling reaction uses a different labeling reagent of the general formula: RP—X-LK—Y-RG, wherein atoms, moieties or bonds X, Y, RP, LK RG have been previously described and their characteristics disclosed. The labeling reagents can be isotopically coded isomeric or isobaric labeling reagents. The unique reporter of each different labeling reagent can indicate from which labeling reaction each of the two or more labeled analytes is derived. The labeling reagents can be isomeric or isobaric. Hence, two or more of the labeled analytes of a mixture can be isomeric or isobaric. The mixture can be the sample mixture as disclosed in any of the above-described methods. Characteristics of the labeling reagents and labeled analytes associated with those methods have been previously discussed.

The analytes of the mixture can be peptides. The analytes of the mixture can be proteins. The analytes of the mixture can be peptides and proteins. The analytes of the mixture can be nucleic acid molecules. The analytes of the mixture can be carbohydrates. The analytes of the mixture can be lipids. The analytes of the mixture can be steroids. The analytes of the mixture can be small molecules of less than 1500 daltons. The analytes of the mixture comprise two or more analyte types. The analyte types can, for example, be selected from peptides, proteins, oligonucleotides, carbohydrates, lipids, steroids and/or small molecules of less than 1500 daltons.

In various embodiments, a mixture of the invention comprises at least two labeled analytes, wherein at least one of the labeled analytes originates from a different sample from the other labeled analytes, combined to form the mixture. For example, the analyte can be a protein, a peptide, a nucleotide, a carbohydrate, a lipid, asteroid or a small molecule of less than 1500 daltons.

In various embodiments, the labeled analytes can be represented by any of Structural Formulas I$^w$, I$^{\#}$I, I-S' to VI-S' or I to VI, typically one of I to VI, wherein RG represents the reaction product of a nucleophilic group or electrophilic group and the analyte, e.g., the labeled analytes can be represented by one of the following formulas:

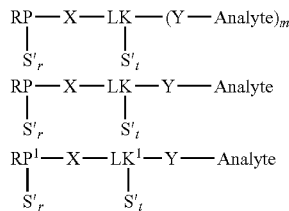
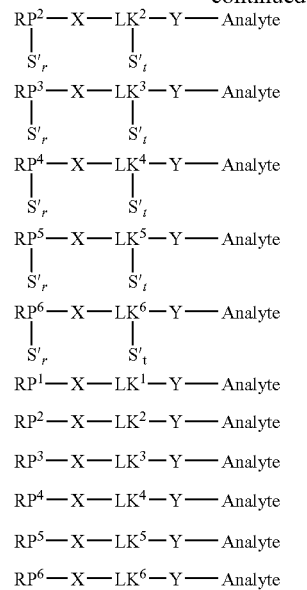

or a salt form and/or hydrate form thereof, wherein the variables are as defined above. Typically at least one of RP/LK (or RP$^1$/LK$^1$, RP$^2$/LK$^2$, RP$^3$/LK$^3$, RP$^4$/LK$^4$, RP$^5$/LK$^5$ or RP$^6$/LK$^6$) can be isotopically enriched with one or more heavy atom isotopes; and the group RP—X-LK— (or RP$^1$—X-LK$^1$—, RP$^2$—X-LK$^2$—, RP$^3$—X-LK$^3$—, RP$^4$—X-LK$^4$—, RP$^5$—X-LK$^5$—, or RP$^6$—X-LK$^6$—) of each labeled analyte can have the same mass.

Upon fragmentation of the moiety added to the analyte by reaction of the labeling reagent with the analyte, RP of each labeled analyte can then yield a signature ion that identifies the sample from which the analyte originated. Accordingly, the intensity of the signature ion relates to the amount of the analyte in the mixture as well as the amount of analyte in the original sample added to form the sample mixture. In some embodiments, each of RP and LK comprise at least two heavy atom isotopes. In some embodiments, each of RP and LK comprise at least three heavy atom isotopes.

For example, in some embodiments, the method of the invention comprises reacting two or more samples, each sample comprising one or more reactive analytes, with a set of labeling reagents or "isobaric mass tags" to thereby produce two or more differentially labeled samples each comprising one or more labeled analytes, and mixing two or more of the differentially labeled samples, or a portion thereof, and optionally one or more calibration standards to thereby produce a sample mixture.

Once the labeling reagent is reacted with the reactive analyte, bond Y can link the linker to the analyte; at least one of RP (respectively represented by RP$^1$, RP$^2$, RP$^3$, RP$^4$, RP$^5$, and RP$^6$ in the various formula) and LK (respectively represented by LK$^1$, LK$^2$, LK$^3$, LK$^4$, LK$^5$ and LK$^6$ in the various formula), e.g. RP can be isotopically enriched with one or more heavy atom isotopes; upon reaction of the isobaric mass tag with an analyte, each mass tag can add the same mass to the analyte; and upon fragmentation, RP (respectively represented by RP$^1$, RP$^2$, RP$^3$, RP$^4$, RP$^5$ and RP$^6$ in the various formula) of each isobaric mass tag can yield a signature ion having a different mass from the signature ions of the other isobaric mass tags in the set.

Exemplary compounds (e.g. mass tags/labeling reagents) that can be used to label analytes according to the method describe above have been previously discussed under the heading: "Compounds".

D. Kits

In various embodiments, a kit of the invention can comprise one or more labeling reagents or "isobaric mass tags", at least one of which can be represented by any of Structural Formulas I''', I#, I-S' to VI-S' or I to VI, typically one of I to VI, or a salt form and/or hydrate form thereof, wherein RG represents a nucleophilic group or electrophilic group and wherein the remaining variables are as defined above.

Compounds selected for use in the kits typically will be "isotopically encoded". By "isotopically encoded" we mean that the distribution of isotopes in each of the compounds of the kit is selected to produce, for each different compound (i.e. labeling reagent) a reporter that comprises a unique mass.

Typically at least one of the reporter group and the linker group (e.g., RP/LK, $RP^1/LK^1$, $RP^2/LK^2$, $RP^3/LK^3$, $RP^4/LK^4$, $RP^5/LK^5$ or $RP^6/LK^6$ in the various formulas) can be isotopically enriched with one or more heavy atom isotopes; and the group RP—X-LK— (or $RP^1$—X-$LK^1$—, $RP^2$—X-$LK^2$—, $RP^3$—X-$LK^3$—, $RP^4$—X-$LK^4$—, $RP^5$—X-$LK^5$—, or $RP^6$—X-$LK^6$—) of each labeled analyte has the same mass. Typically, upon fragmentation, RP of each labeled analyte can then yield a signature ion having a different mass from the signature ions of the other isobaric mass tags in the kit.

Other properties of the labeling reagents have likewise been disclosed. For example, the labeling reagents can be useful for the multiplex analysis of one or more analytes in the same sample, or in two or more different samples.

Each isobaric labeling reagent (i.e. mass tag) of the kit is isotopically enriched (coded) with at least one heavy atom isotope. The labeling reagents can be isotopically enriched to comprise two or more heavy atom isotopes. The labeling reagents can be isotopically enriched to comprise three or more heavy atom isotopes. The labeling reagents can be isotopically enriched to comprise four or more heavy atom isotopes. In some embodiments, at least one heavy atom isotope can be incorporated into a carbonyl or thiocarbonyl group of the labeling reagent and at least one other heavy atom isotope cam be incorporated into the reporter group of the labeling reagent.

The labeling reagents comprise a reporter group that contains a fixed charge or that is ionizable. The reporter group therefore can include basic or acidic moieties that are easily ionized. In some embodiments, the reporter can be a carboxylic acid, sulfonic acid or phosphoric acid group containing compound. Accordingly, is some embodiments, the labeling reagents can be isolated in their salt form.

In some embodiments, the labeling reagents can comprise a carbonyl or thiocarbonyl linker. Labeling reagents comprising a carbonyl or thiocarbonyl linker can be used in active ester form for the labeling of analytes. In an active ester, an alcohol group forms a leaving group (LG), e.g., in some embodiments, the leaving groups depicted in FIG. 9. In some embodiments, the active ester can be an N-hydroxysuccinimidyl ester.

EXAMPLES

Aspects of the present teachings may be further understood in light of the following examples, which should not be construed as limiting the scope of the present invention in any way.

Definitions for some of the abbreviations that are used in the examples are as follows: HMI stands for Hexamethyleneimine, Pbf stands for 2,2,4,6,7-Pentamethyl-dihydrobenzofuran-5-sulfonyl, Fmoc stands for 9-Fluorenylmethoxycarbonyl, Trt stands for Trityl, Mpe stands for 3-Methyl-pent-3-yl, HATU stands for O-(7-Azabenzotriazol-1-yl)-N,N,N',N'-tetramethyluronium hexafluorophosphate, NMP stands for 1-Methyl-2-pyrrolidinone, FmocOSu stands for (9-Fluorenylmethoxycarbonyloxy) succinimide, DMAP stands for 4-Dimethylaminopyridine, THF stands for Tetrahydrofuran, HBTU stands for O-(Benzotriazol-1-yl)-N,N,N',N'-tetramethyluronium hexafluorophosphate, and HOBT stands for 1-Hydroxybenzotriazole hydrate.

Figure 10:
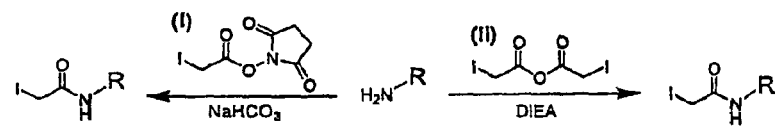
FIG. 10 illustrates Protocol I and II for amine acylation to generate a reactive group on a mass tag.

General Protocols of Amine Acylations to Generate a Reactive Group on a Mass Tag:

FIG. 10 illustrates Protocol I and Protocol II for amine acylation to generate a reactive group on a mass tag suitable for reacting with the thiol group of cystine amino acids.

Protocol I: A respective amine (1-400 µmol) was dissolved in aqueous sodium bicarbonate (0.2 M) and acetonitrile (v/v 2:1 or 1:1). Typically, the concentration of the amine was in the range of between about 0.01 to about 0.1 M. N-Hydroxysuccinimidyl iodoacetate in acetonitrile (about 0.4 M, around 10 fold excess relative to the free amine) was added while vortexing the reaction mixture. The mixture was shaken at room temperature for about 10 min. to about 30 min. The product was purified with HPLC, and confirmed with mass spectrometry (MS).

Protocol II: Iodoacetic anhydride (0.74 g, 2.1 mmol) in $CH_2Cl_2$ (3 mL) was added to a stirred solution of a respective amine (1.9 mmol) with N, N-diisopropylethylamine (DIEA, 1.9 mmol) at room temperature. The reaction solution was further stirred at room temperature for 1.5-3 hour, then partitioned between methylene chloride and water. The organic layer was dried with anhydrous $Na_2SO_4$, concentrated in vacuo, and purified with silica gel flash chromatography. The product was characterized with NMR and/or MS.

Syntheses of Mass Tags (Labeling Reagents)

I. Synthesis of Mass Tag (1)

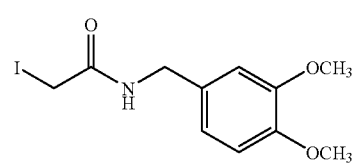

(1)

Commercially available 3,4-dimethoxybenzyl amine (Aldrich) was acylated according to Protocol II to form Mass Tag (1). $^1$H NMR (CDCl$_3$): δ 3.72 (s, 2H), 3.90 (s, 6H), 4.60 (d, 2H), 6.61 (d, 2H), 7.28 (t, 1H). [M+H]$^+$ in MS: 336.0, calculated; 336.0, found.

II. Synthesis of Mass Tag (2)

Figure 11:
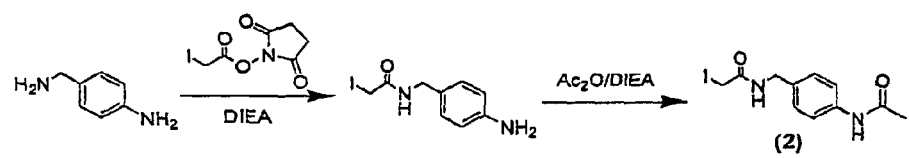
FIG. 11 illustrates the synthesis of Mass Tag (2).

FIG. 11 illustrates the synthesis of Mass Tag (2). 4-Aminobenzylamine (Aldrich, 1 mmol), N-succinimidyl iodoacetate (Pierce, 1 mmol), and N,N-diisopropyl ethylamine (DIEA, 100 µL) were mixed in dichloromethane (10 mL) and stirred at room temperature for 1 hr. Solvent was removed under reduced pressure. The product was purified by silica gel column chromatography, eluting with hexane, ethyl acetate (20%-60%), to give 4-amino-N-iodoacetylbenzylamine (62.2% yield). $^1$H NMR (MeOD): 7.1 (d, 2H), 6.75 (d, 2H), 4.21 (s, 2H), 3.65 (s, 2H). [M+H]$^+$ in MS: 291.0, calculated; 291.0, found.

4-amino-N-iodoacetylbenzylamine (0.172 mmol), acetic anhydride (0.2 ml), and DIEA (0.2 ml) were stirred in acetonitrile (3 ml) for 1.5 hours. The solvent was evaporated under reduced pressure. The residual was partitioned between dichloromethane and water. The organic layer was dried with anhydrous sodium sulfate, filtered and concentrated in vacuo. The brownish residual was purified with silica gel column chromatography, eluting with dichloromethane and methanol to give the product, Mass Tag (2) (35 mg, 61% yield). [M+H]$^+$ in MS: 333.0 calculated; 333.0, found.

III. Synthesis of Mass Tag (3)

Figure 12:
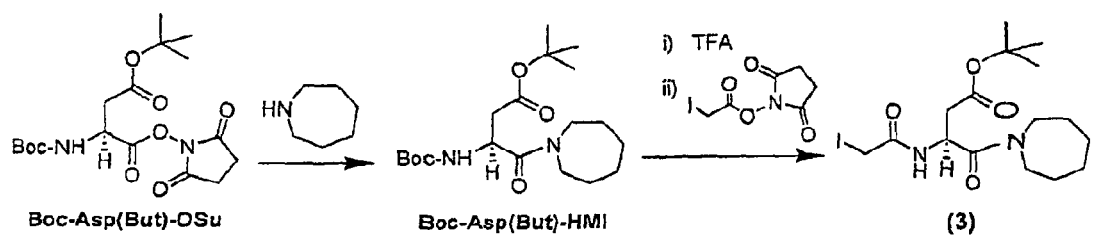
FIG. 12 illustrates the synthesis of Mass Tag (3).

FIG. 12 illustrates the synthesis of Mass Tag (3). To a mixture of N-Boc-β-tert-butyl-α-succinimido-aspartic acid (Boc-Asp(But)-OSu) (Bacchem, 0.1 mmol) in DMF (1 ml) was added hexamethyleneimine (Aldrich, 0.4 mmol). More DMF (2 ml) was added. The mixture was shaken at room temperature for 2 hours to form Boc-Asp(But)-HMI. Boc-Asp(But)-HMI was purified with preparative HPLC, and characterized with MS ([M+H]$^+$: 371.3, calculated; 371.1, found).

The Boc-protected amine group of Boc-Asp(But)-HMI was deprotected by exposure to a solution of methylene chloride (0.1 ml) and trifluoroacetic acid (TFA, 0.1 ml) at room temperature for 20 minutes. The solvents were evaporated in vacuo at 40° C. to dryness. The free amine was then acylated with Protocol I to furnish Mass Tag (3) ([M+H]$^+$: 383.0, calculated; 383.0, found).

IV. Syntheses of Mass Tag (4) and Mass Tag (5)

Figure 13:
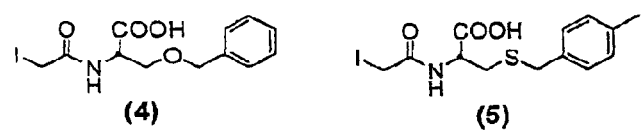
FIG. 13 illustrates Mass Tags (4) and (5).

FIG. 13 Illustrates Mass Tags (4) and (5).

Mass Tag (4) was prepared by acylating the amine group of commercially available O-benzyl serine using Protocol I. ([M+H]$^+$ in MS: 364.0, calculated; 364.0, found).

Mass Tag (5) was prepared by acylating the amine group of commercially available S-(p-methyl benzyl) cysteine using Protocol I. ([M+H]$^+$ in MS: 394.0, calculated; 394.0, found).

V. Syntheses of Mass Tags (6), (7) and (8).

Figure 14:
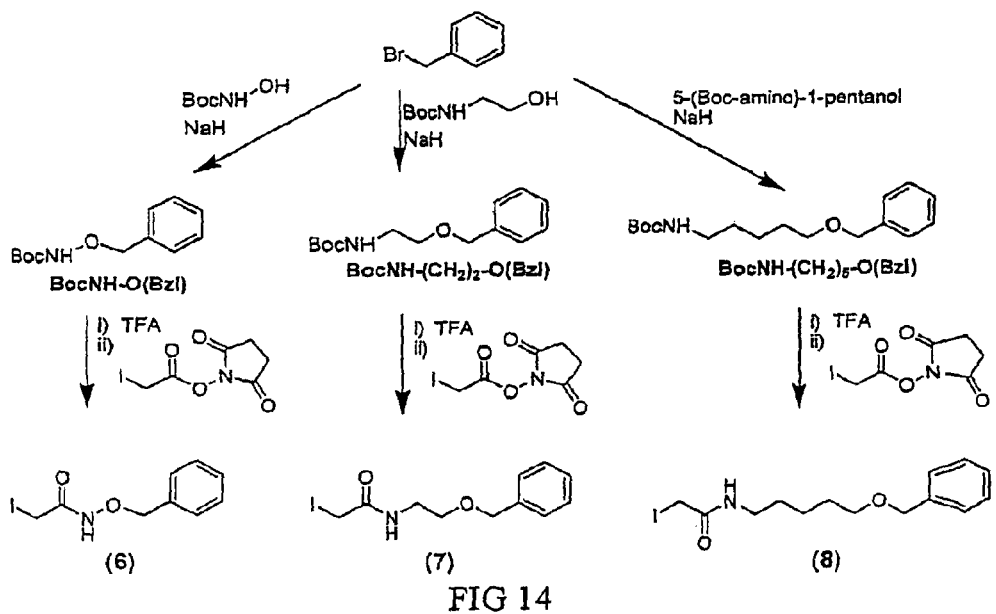
FIG. 14 illustrates the syntheses of Mass Tags (6), (7) and (8).

FIG. 14 Illustrates the Syntheses of Mass Tags (6), (7) and (8).

A. Synthesis of Mass Tag (6)

A solution of a BocNH—OH (1-2 mmol) in DMF (2-4 ml) was cooled with an ice-water bath. Sodium hydride (1.5-2 equivalent to the BocNH—OH) was added. After evolution of hydrogen gas ceased, benzyl bromide (Aldrich, 1 equivalent to the BocNH—R—OH) was added while vortexing the mixture. The mixture was shaken at room temperature for 5 hours. After centrifugation, the product, BocNH—O(Bzl), was purified with preparative HPLC, and characterized with MS.

The Boc-protected amine group of BocNH—O(Bzl) was deprotected by exposure to 4-8 ml of 25% TFA in methylene chloride at room temperature for 30 minutes. The deprotected compound, NH$_2$—O(Bzl), was extracted with water twice, and then either purified with preparative HPLC or used directly in the acylation reaction after evaporation of solvents.

NH$_2$—O(Bzl) was acylated with Protocol I to furnish Mass Tag (6) ([M+H]$^+$: 292.0, calculated; 292.0, found).

B. Synthesis of Mass Tag (7)

A solution of a BocNH—CH$_2$CH$_2$—OH (1-2 mmol) in DMF (2-4 ml) was cooled with an ice-water bath. Sodium hydride (1.5-2 equivalent to the BocNH—CH$_2$CH$_2$—OH) was added. After evolution of hydrogen gas ceased, benzyl bromide (Aldrich, 1 equivalent to the BocNH—CH$_2$CH$_2$—OH) was added while vortexing the mixture. The mixture was shaken at room temperature for 5 hours. After centrifugation, the product, BocNH—CH$_2$CH$_2$—O(Bzl), was purified with preparative HPLC, and characterized with MS.

The Boc-protected amine group of BocNH—CH$_2$CH$_2$—O(Bzl) was deprotected by exposure to 4-8 ml of 25% TFA in methylene chloride at room temperature for 30 minutes. The deprotected compound, NH$_2$—CH$_2$CH$_2$—O(Bzl), was extracted with water twice, and then either purified with preparative HPLC or used directly in the acylation reaction after evaporation of solvents.

NH$_2$—CH$_2$CH$_2$—O(Bzl) was acylated with Protocol I to furnish Mass Tag (7) ([M+H]$^+$: 320.0, calculated; 320.0, found).

C. Synthesis of Mass Tag (8)

A solution of a BocNH—(CH$_2$)$_5$—OH (1-2 mmol) in DMF (2-4 ml) was cooled with an ice-water bath. Sodium hydride (1.5-2 equivalent to the BocNH—(CH$_2$)$_5$—OH) was added. After evolution of hydrogen gas ceased, benzyl bromide (Aldrich, 1 equivalent to the BocNH—(CH$_2$)$_5$—OH) was added while vortexing the mixture. The mixture was shaken at room temperature for 5 hours. After centrifugation, the product, BocNH—(CH$_2$)$_5$—O(Bzl), was purified with preparative HPLC, and characterized with MS.

The Boc-protected amine group of BocNH—(CH$_2$)$_5$—O(Bzl) was deprotected by exposure to 4-8 ml of 25% TFA in methylene chloride at room temperature for 30 minutes. The deprotected compound, NH$_2$—(CH$_2$)$_5$—O(Bzl), was extracted with water twice, and then either purified with preparative HPLC or used directly in the acylation reaction after evaporation of solvents.

NH$_2$—(CH$_2$)$_5$—O(Bzl) was acylated with Protocol I to furnish Mass Tag (8) ([M+H]$^+$: 362.1, calculated; 362.2, found).

VI. Syntheses of Mass Tags (9), (10) and (11)

Figure 15:
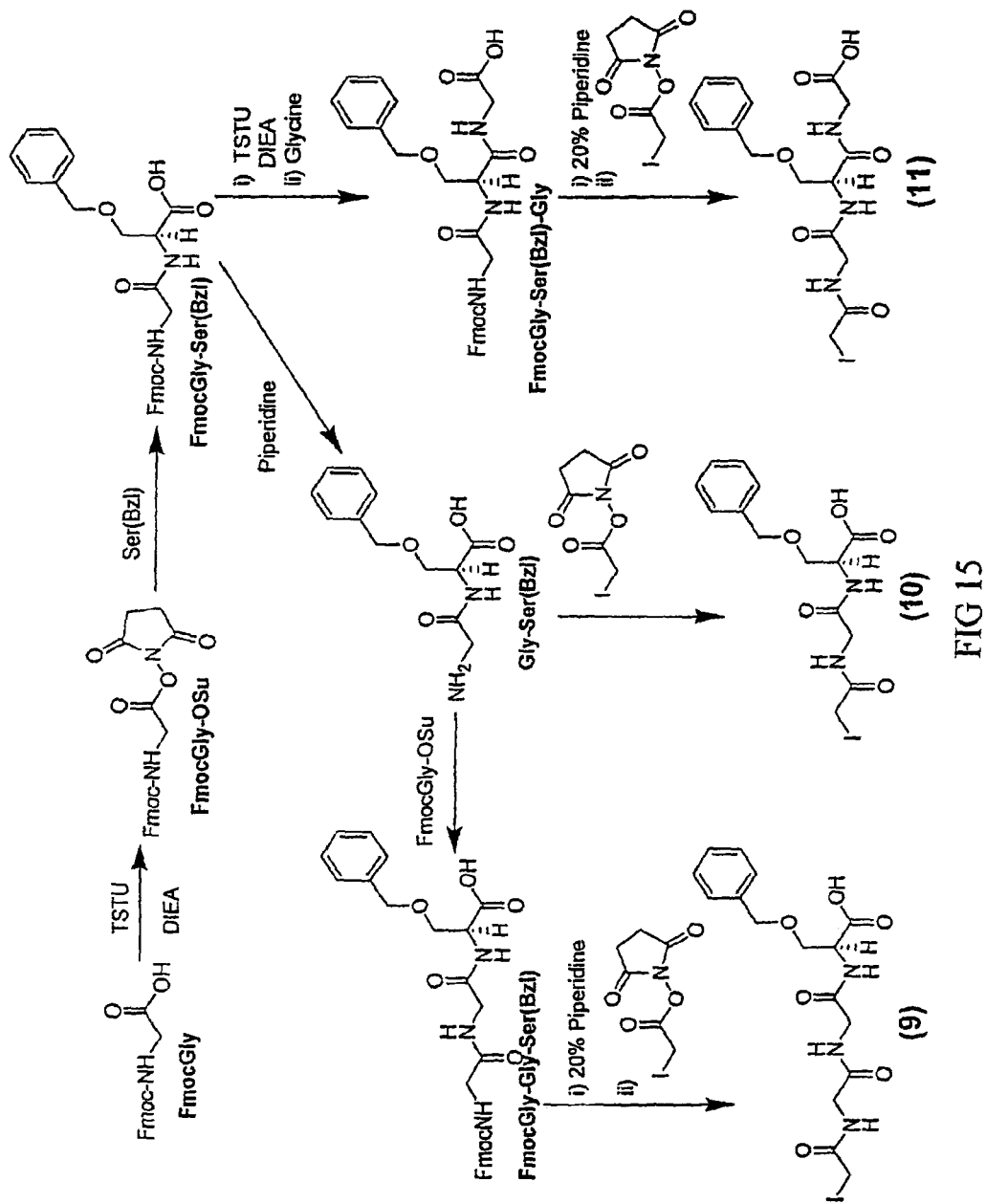
FIG. 15 illustrates the syntheses of Mass Tags (9), (10) and (11).

FIG. 15 Illustrates the Syntheses of Mass Tags (9), (10) and (11).

A. Synthesis of Mass Tag (9)

FmocGly (Applied Biosystems, 1 mmol), N,N,N',N'-tetramethyl(succinimido)-uranium tetrafluoroborate (TSTU, Advanced ChemTech, 1 mmol) and N,N-diisopropylethylamine (DIEA, Aldrich, 2 mmol) were dissolved in N,N-dimethylformamide (DMF, Burdick & Jackson, 6 ml). The mixture was shaken at room temperature for half an hour. The solvent was evaporated to form FmocGly-OSu, which was used directly in the following steps.

To L-Serine(Bzl) (NovaBiochem, 0.4 mmol) in DMF (0.8 ml) and 0.2 M aqueous sodium bicarbonate (2.8 ml) was added FmocGly-OSu (0.4 mmol) in DMF (2.4 ml) while vortexing. The mixture was shaken at room temperature for 20 minutes. The compound, FmocGly-Ser(Bzl), was purified with preparative HPLC, and characterized with MS ([M+H]$^+$: 475.2, calculated; 475.2, found).

FmocGly-Ser(Bzl) (0.17 mmol) was exposed to 4 ml of 20% piperidine in DMF at room temperature for 15 minutes to remove the Fmoc-protecting group. The solvents were evaporated in vacuo at 40° C., and the residual was purified with preparative HPLC. The compound, Gly-Ser(Bzl), was characterized with MS ([M+H]$^+$: 253.1, calculated; 253.2, found).

FmocGly-OSu (0.08 mmol) in DMF (0.48 ml) was added to Gly-Ser(Bzl) in DMF (2.6 ml) and 0.2 M aqueous sodium bicarbonate (0.26 ml) while vortexing. The mixture was shaken at room temperature for 20 minutes. The compound formed, FmocGly-Gly-Ser(Bzl), was purified with preparative HPLC, and characterized with MS ([M+H]$^+$: 532.2, calculated; 532.2, found).

FmocGly-Gly-Ser(Bzl) (0.5 mg) was exposed to 0.2 ml of 20% piperidine in DMF at room temperature for 10 minutes to remove the Fmoc-protecting group. The solvent was evaporated in vacuo at 40° C. to dryness. The deprotected amine was acylated using Protocol I to furnish Mass Tag (9) ([M+H]$^+$ in MS: 478.0, calculated; 478.0, found).

B. Synthesis of Mass Tag (10)

Gly-Ser(Bzl) was prepared as in Section A and was acylated using Protocol I to furnish. Mass Tag (10) ([M+H]$^+$: 421.0, calculated; 421.0, found).

C. Synthesis of Mass Tag (11)

FmocGly-Ser(Bzl) (0.01 mmol), TSTU (0.02 mmol), and DIEA (0.02 mmol) were dissolved in DMF (0.1 ml). The mixture was shaken at room temperature for 40 minutes, and then transferred to glycine (0.1 mmol) and sodium bicarbonate (0.2 mmol) in water (0.05 ml) while vortexing. The mixture was shaken at room temperature for 30 minutes. The product, FmocGly-Ser(Bzl)-Gly, was purified with semi-preparative HPLC, and characterized with MS ([M+H]$^+$: 532.2, calculated; 532.2, found).

FmocGly-Ser(Bzl)-Gly (1 mg) was exposed to a solution of 0.2 ml of 20% piperidine in DMF for 10 minutes to remove the Fmoc-protecting group. After evaporation of solvents in vacuo at 40° C., the deprotected amine was acylated using Protocol I to furnish Mass Tag (11) ([M+H]$^+$: 478.0, calculated; 478.0, found).

VII. Synthesis of Mass Tag (12)

Figure 16:
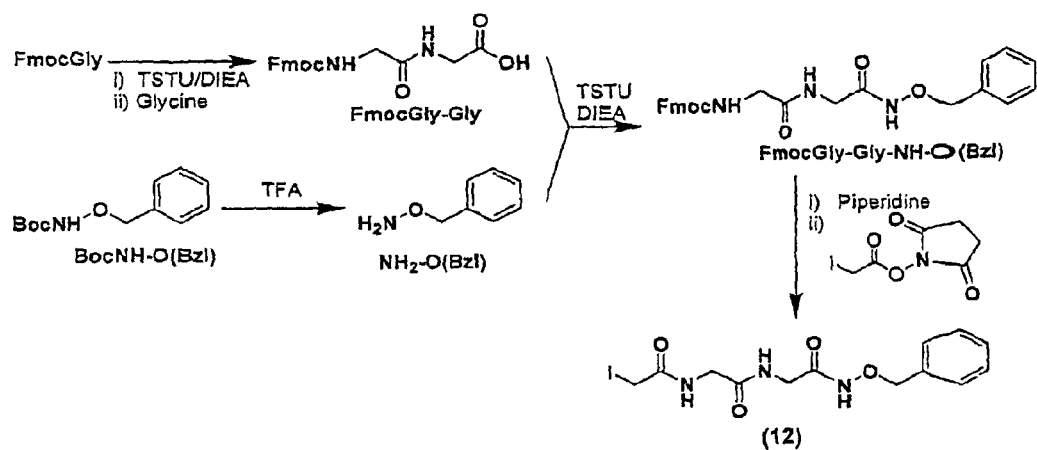
FIG. 16 illustrates the synthesis of Mass Tag (12).

FIG. 16 Illustrates the Synthesis of Mass Tag (12).

FmocGly (1 mmol), TSTU (1 mmol), and DIEA (1.5 mmol) were dissolved in DMF (5 ml). The mixture was shaken at room temperature for 40 minutes, and then transferred to a solution of glycine (4 mmol) in 5 ml of 0.2 M aqueous sodium bicarbonate while vortexing. The mixture was shaken at room temperature for 20 minutes. The product, FmocGly-Gly, was purified with preparative HPLC, and characterized with MS ([M+H]$^+$: 355.2, calculated; 355.2, found).

BocNH—O(Bzl) (see Section V.A. and FIG. 14 for preparation) (0.2 mmol) was exposed to a solution of 5 ml of 25% TFA in methylene chloride for 30 minutes to remove the Boc-protecting group to form NH$_2$—)(Bzl). NH$_2$—O(Bzl) was extracted with water, purified with preparative HPLC, and characterized with MS ([M+H]$^+$: 124.1, calculated; 124.2, found).

FmocGly-Gly (0.02 mmol), TSTU (0.02 mmol), and DIEA (0.03 mmol) were dissolved in DMF (0.2 ml). The mixture was shaken at room temperature for 40 minutes, and then transferred to a solution of NH$_2$—O(Bzl) (2 mg) in DMF (0.1 ml) and 0.2 M aqueous sodium bicarbonate (0.1 ml) while vortexing. The mixture was shaken at room temperature for 20 minutes. The product, FmocGly-Gly-NH—O(Bzl), was purified with HPLC, and characterized with MS ([M+H]$^+$: 406.0, calculated; 405.8, found).

FmocGly-Gly-NH—O(Bzl) was exposed to a solution of 0.2 ml of 20% piperidine in DMF at room temperature for 10 minutes to remove the Fmoc-protecting group. After evaporation of all the solvents, the deprotected amine was acylated using Protocol I to furnish Mass Tag (12) ([M+H]$^+$: 406.0, calculated; 405.8, found).

VIII. Synthesis of Mass Tag (13)

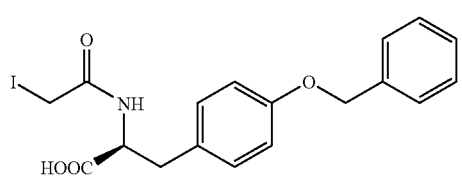

(13)

O-Benzyl tyrosine was acylated using Protocol I to form Mass Tag (13). ([M+H]$^+$ in MS: 440.0, calculated; 440.2, found).

IX. Syntheses of Mass Tags (14) and (15)

Figure 17:
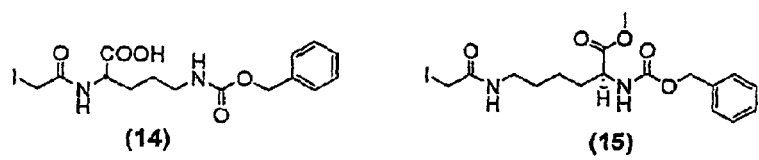
FIG. 17 illustrates Mass Tags (14) and (15).

FIG. 17 Illustrates Mass Tags (14) and (15).

The α-amine group of ε-N-(benzyloxycarbonyl)-lysine was acylated using Protocol I to form Mass Tag (14). ([M+H]$^+$ in MS: 435.0, calculated; 435.0, found).

The ε-amine group of α-N-(benzyloxycarbonyl)-lysine was acylated using Protocol I to form Mass Tag (15). ([M+H]$^+$ in MS: 463.1, calculated; 463.0, found).

X. General Protocol for Syntheses of Mass Tags (16), (17), (18), (19) and (20)

Figure 18:
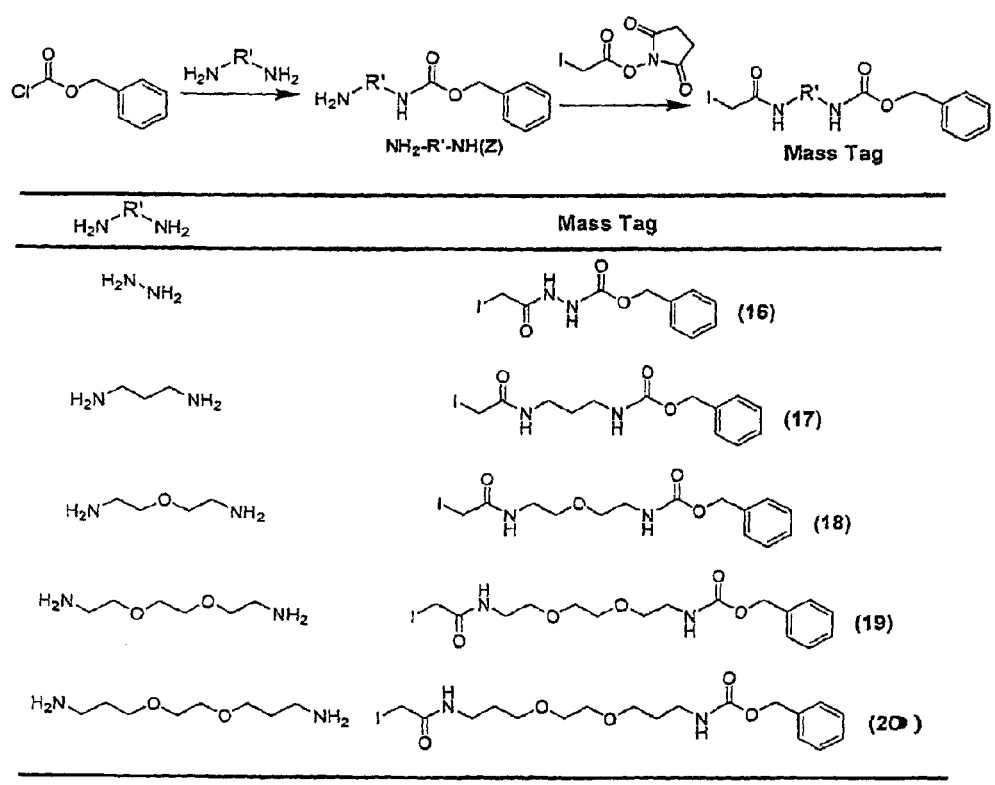
FIG. 18 illustrates a general protocol for syntheses of Mass Tags (16), (17), (18), (19) and (20).

FIG. 18 Illustrates a General Protocol for Syntheses of Mass Tags (16), (17), (18), (19) and (20).

To a diamine (NH$_2$—R'—NH$_2$) (0.4-4 mmol) in 0.2 M aqueous sodium bicarbonate (1-4 ml) was added benzyl chloroformate (Alfa Aesar, 0.1-2 mmol) in DMF (1-4 ml) while vortexing. R' is defined in FIG. 18. The molar ratio for benzyl chloroformate versus diamine was 1:2-6. The mixture was shaken at room temperature for 5-20 minutes. The product, NH$_2$—R'—NH(Z), was purified with preparative HPLC, and characterized with MS. The monoamine was then acylated using Protocol I to furnish an appropriate mass tag.

Mass Tag (16) ([M+H]$^+$ in MS: 335.0, calculated; 335.0, found). Mass Tag (17) ([M+H]$^+$ in MS: 377.0, calculated; 377.0, found). Mass Tag (18) ([M+H]$^+$ in MS: 407.1, calculated; 407.2, found). Mass Tag (19) ([M+H]$^+$ in MS: 451.1, calculated; 451.0, found). Mass Tag (20) ([M+H]$^+$ in MS: 479.1, calculated; 479.2, found).

XI. Syntheses of Mass Tags (21), (22), (23), and (24)

Figure 19:
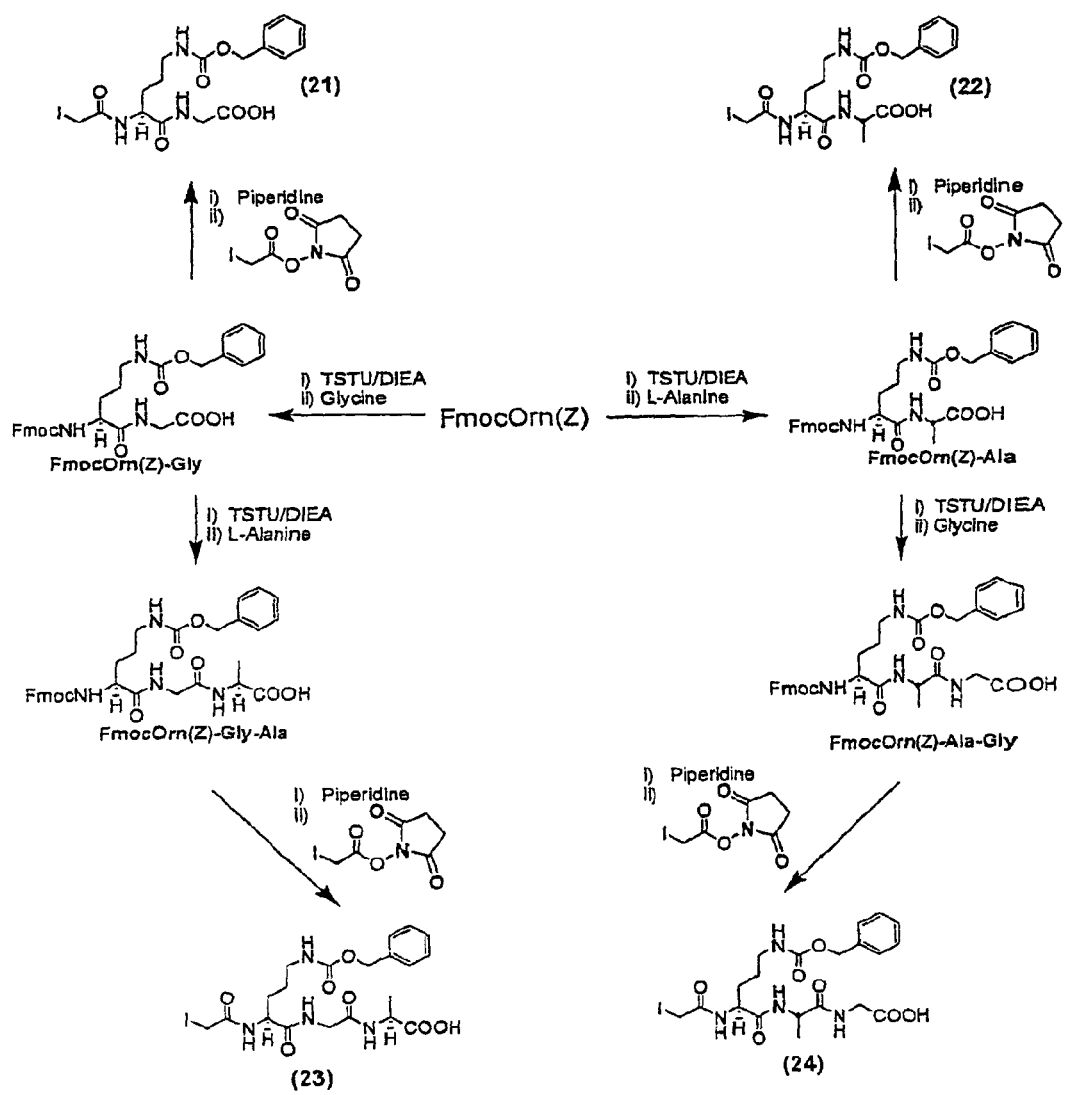
FIG. 19 illustrates the syntheses of Mass Tags (21), (22), (23) and (24).

FIG. 19 Illustrates the Syntheses of Mass Tags (21), (22), (23) and (24).

A. Synthesis of Mass Tag (21)

α-N-Fmoc-γ-N-(benzyloxycarbonyl)ornithine (FmocOrn(Z)) (Advanced ChemTech, 0.25 mmol), TSTU (0.25 mmol), and DIEA (0.375 mmol) were dissolved in DMF (3 mL). The mixture was shaken at room temperature for 1 hour, and then transferred to a solution of 1 mmol of glycine with sodium bicarbonate in water (3 mL). The mixture was shaken at room temperature for 30-60 minutes. The product, FmocOrn(Z)-Gly, was purified with preparative HPLC, and characterized with MS (FmocOrn(Z)-Gly: [M+H]$^+$: 546.2, calculated; 546.4, found).

FmocOrn(Z)-Gly (2 mg) was exposed to a solution of 0.1 mL of 20% piperidine in DMF for 10 minutes to remove the Fmoc-protecting group. After evaporation of all the solvents, the deprotected amine was acylated using Protocol I to furnish Mass Tag (21) [M+H]$^+$: 492.1, calculated; 492.0, found).

B. Synthesis of Mass Tag (22)

α-N-Fmoc-γ-N-(benzyloxycarbonyl)ornithine (FmocOrn(Z)) (Advanced ChemTech, 0.25 mmol), TSTU (0.25 mmol), and DIEA (0.375 mmol) were dissolved in DMF (3 mL). The mixture was shaken at room temperature for 1 hour, and then transferred to a solution of 1 mmol of L-alanine with sodium bicarbonate in water (3 mL). The mixture was shaken at room temperature for 30-60 minutes. The product, FmocOrn(Z)-Ala, was purified with preparative HPLC, and characterized with MS (FmocOrn(Z)-Ala: [M+H]$^+$: 560.2, calculated; 560.2, found).

FmocOrn(Z)-Ala (2 mg) was exposed to a solution of 0.1 mL of 20% piperidine in DMF for 10 minutes to remove the Fmoc-protecting group. After evaporation of all the solvents, the deprotected amine was acylated using Protocol I to furnish Mass Tag (22) ([M+H]$^+$: 506.1, calculated; 505.8, found).

C. Synthesis of Mass Tag (23)

FmocOrn(Z)-Gly (0.1 mmol), TSTU (0.2 mmol), and DIEA (0.3 mmol) were dissolved in DMF (1 ml). The mixture was shaken at room temperature for 1 hour, and then transferred to a solution of sodium bicarbonate (1.5 mmol) and L-alanine (1 mmol) in water (1 ml). The mixture was shaken at room temperature for 30 minutes. The product, FmocOrn(Z)-Gly-Ala, was purified with preparative HPLC, and characterized with MS ([M+H]$^+$: 617.2, calculated; 617.2, found).

FmocOrn(Z)-Gly-Ala (2 mg) was exposed to a solution of 0.1 ml of 20% piperidine in DMF for 10 minutes to remove the Fmoc-protecting group. After evaporation of all the solvents, the deprotected amine was acylated using Protocol I to furnish Mass Tag (23) ([M+H563.1, calculated; 563.2, found).

D. Synthesis of Mass Tag (24)

FmocOrn(Z)-Ala (0.1 mmol), TSTU (0.2 mmol), and DIEA (0.3 mmol) were dissolved in DMF (1 ml). The mixture was shaken at room temperature for 1 hour, and then transferred to a solution of sodium bicarbonate (1.5 mmol) and glycine (1 mmol) in water (1 ml). The mixture was shaken at room temperature for 30 minutes. The product, FmocOrn(Z)-Ala-Gly, was purified with preparative HPLC, and characterized with MS ([M+H]$^+$: 617.2, calculated; 617.2, found).

FmocOrn(Z)-Ala-Gly (2 mg) was exposed to a solution of 0.1 ml of 20% piperidine in DMF for 10 minutes. After evaporation of all the solvents, the deprotected amine was acylated using Protocol I to furnish Mass Tag (24) ([M+H]$^+$: 563.1, calculated; 563.2, found).

XII. Mass Tag Labeled Glu-Fib Peptide

[Glu$^1$]-Fibrinopeptide B human [Glu-Fib, SEQ ID No.: 25 GVNDNEEGFFSAR), CAS#: 103213-49-6]: The peptide was assembled on trityl chloride resin (P/N: Novabiochem, 01-64-0074) using standard Fmoc-peptide synthesis protocol (Novabiochem catalog, 2004-2005). The following amino acid derivatives were used: Fmoc-Arg(Pbf)-OH (P/N: Novabiochem, 04-12-1145), Fmoc-Glu(O$^t$Bu)—OH (P/N: Novabiochem, 04-12-1020), Fmoc-Gly-OH (P/N: Novabiochem, 04-12-1001), Fmoc-Val-OH (P/N: Novabiochem, 04-12-1039), Fmoc-Asn(Trt)-OH (P/N: Novabiochem, 04-12-1089), Fmoc-Asp(Mpe)-OH (P/N: Bachem, B-3560), Fmoc-Phe-OH (P/N: Novabiochem, 04-12-1030), Fmoc-Ser($^t$Bu)—OH (P/N: Novabiochem, 04-12-1033), Fmoc-Ala-OH (P/N: Novabiochem, 04-12-1006).

Figure 30:
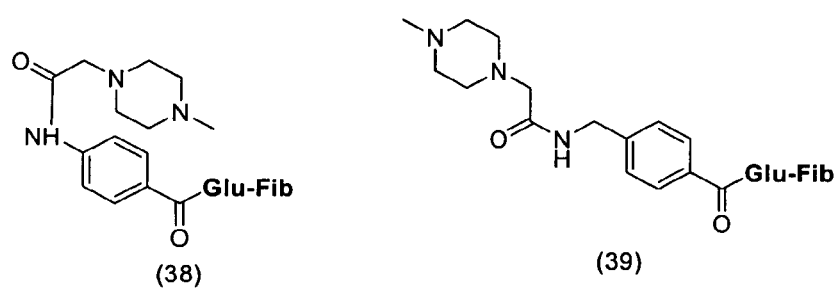
FIG. 30 illustrates the chemical structures of Mass Tag labeled Glu-Fib peptides (38) and (39).

A. Synthesis of Mass Tag Labeled Glu-Fib Peptide (38) (See FIG. 30)

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP). 4-(Fmoc-amino)benzoic acid (P/N: Bachem, B-3260; 10 eqv to Glu-Fib amount on the resin) was activated with HATU (P/N: Applied Biosystems 4317033, 9.5 eqv) and N,N-Diisopropylethylamine (30 eqv) in NMP (~1 mL), added to the resin and mixed for 30 min. Resin was then filtered, washed with NMP, and Fmoc group was cleaved. Piperazine acetic acid-TFA salt (10 eqv) was then activated using HATU (9.5 eqv) and N,N-Diisopropylethylamine (60 eqv) in NMP (~1.5 mL) and added to the resin. After 30 min resin was washed with NMP followed by CH$_3$CN. Conjugated peptide was cleaved (and deprotected) from resin using 95:5 TFA-water (200 µL, 2 h) and precipitated using Et$_2$O. Analysis of Compound (38) (see FIG. 30) was performed using MALDI-TOF (Sinapinic acid matrix, Calculated [M+H]$^+$=1843.8, Observed [M+H]$^+$=1844.9).

Further Mass Spectral Analysis:

MS/MS analyses of Mass Tag labeled Glu-Fib peptide (38) were performed on MALDI and electrospray platforms. Data indicate that the Mass Tag is a good candidate for MALDI platform but the intensity of the signature ion peak was very weak in electrospray platforms (data not shown). Differentially $^{13}$C, $^{15}$N and/or $^2$H labeled aminobenzoic acids are not commercially available and would need to be synthesized.

B. Synthesis of Mass Tag Labeled Glu-Fib Peptide (39) (See FIG. 30)

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP). 4-(Fmoc-aminomethyl)benzoic acid (P/N: Fluka, 04062; 10 eqv to Glu-Fib amount on the resin) was individually activated with HATU (P/N: Applied Biosystems 4317033, 9.5 eqv) and N,N-Diisopropylethylamine (30 eqv) in NMP (~1 mL), added to the resin and mixed for 30 min. Resin was then filtered, washed with NMP, and the Fmoc group was cleaved. Piperazine acetic acid-TFA salt (10 eqv) was then activated using HATU (9.5 eqv) and N,N-Diisopropylethylamine (60 eqv) in NMP (~1.5 mL) and added to the resin. After 30 min resin was washed with NMP followed by CH$_3$CN. Conjugated peptide was cleaved (and deprotected) from resin using 95:5 TFA-water (200 µL, 2 h) and precipitated using Et$_2$O. Analysis of compound (39) (see FIG. 30) was performed using ES-MS (direct infusion in water, Calculated [M+H]$^+$= 1829.8, Observed [M+H]$^+$=1829.9)

Further Mass Spectral Analysis:

MS/MS analyses of Mass Tag labeled Glu-Fib peptide (39) were performed on MALDI and electrospray platforms. Data indicate that the Mass Tag is a good candidate for MALDI platform but the intensity of the signature ion peak was very weak in electrospray platforms (data not shown). Differentially $^{13}$C, $^{15}$N and/or $^2$H labeled aminobenzoic acids are not commercially available and would need to be synthesized.

Figure 31:
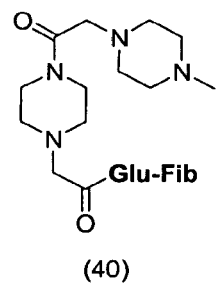
FIG. 31 illustrates the chemical structure of the Mass Tag labeled Glu-Fib peptide (40).

C. Synthesis of Mass Tag: Labeled Glu-Fib Peptide (40) (See FIG. 31)

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP). Fmoc-4-carboxymethyl-piperazine (P/N: Chem-Impex, 04960); 10 eqv to Glu-Fib amount on the resin) was activated with HATU (P/N: Applied Biosystems 4317033, 9.5 eqv) and N,N-Diisopropylethylamine (30 eqv) in NMP (~1 mL), added to the resin and mixed for 30 min. Resin was then filtered, washed with. NMP, and the Fmoc group was cleaved. Piperazine acetic acid-TFA salt (10 eqv) then activated using HATU (9.5 eqv) and N,N-Diisopropylethylamine (60 eqv) in NMP (~1.5 mL) and added to the resin. After 30 min the resin was washed with NMP followed by CH$_3$CN. Conjugated peptide was cleaved (and deprotected) from resin using 95:5 TFA-water (200 µL, 2 h) and precipitated using Et$_2$O. Analysis of compound (40) (see FIG. 31) was performed using ES-MS (direct infusion in water, Calculated [M+H]$^+$= 1836.9, Observed [M+H]$^+$=1837.0)

Further Mass Spectral Analysis:

MS/MS analyses of Mass Tag labeled Glu-Fib peptide (40) were performed on MALDI and electrospray platforms. Data indicate that the Mass Tag is a good candidate for MALDI and electrospray platforms. Signature ion intensity and fragmentation pattern of the peptide were similar to current iTRAQ™ reagent N-Methyl piperazine acetic acid (data not shown).

Figure 32:
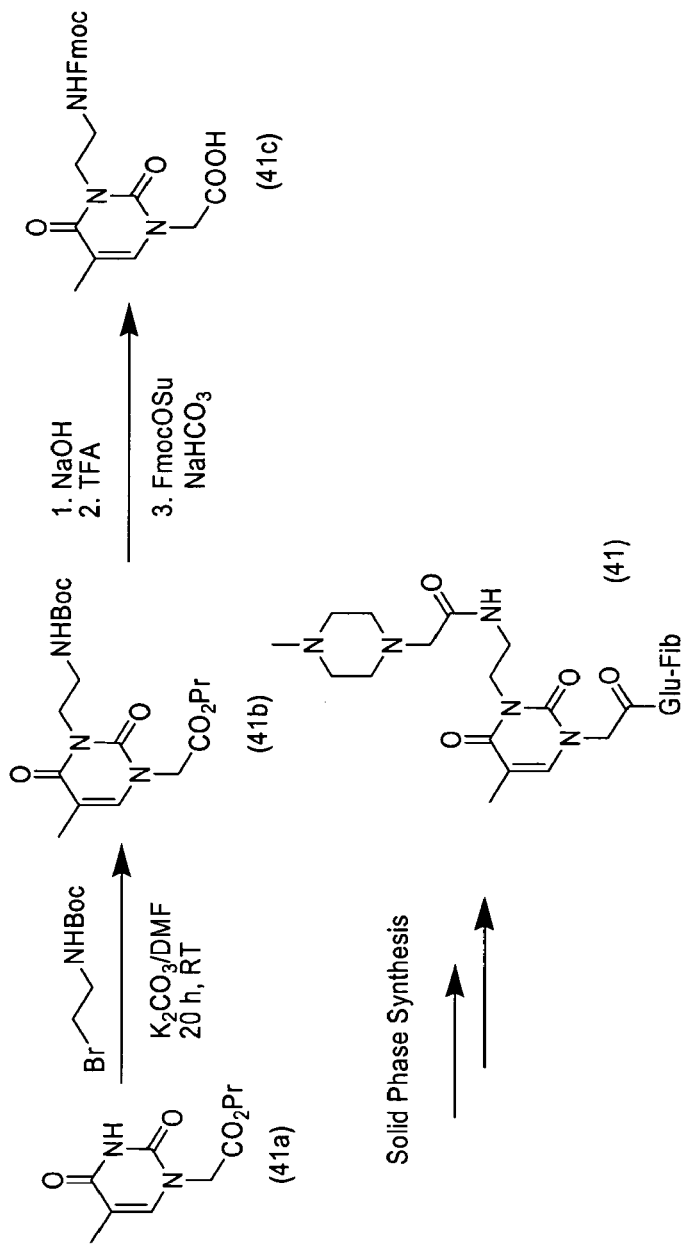
FIG. 32 illustrates the synthesis of Mass Tag labeled Glu-Fib peptide (41).

D. Synthesis of Mass Tag Labeled Glu-Fib Peptide (41) (See FIG. 32)

Compound (41b): To a solution of thymine acetic acid propyl ester (41a) (can be synthesized according to: Alahiane, A.; Taourirte, M.; Rochdi, A.; Redwane, N.; Sebti, S.; Engels, J. W.; Lazrek, H. B., "Building blocks for polyamide nucleic acids: Facile synthesis using potassium fluoride doped natural phosphate as basic catalyst", *Nucleosides, Nucleotides & Nucleic Acids* 2003, 22, 109-114; 1.33 g, 5.88 mmol) and 2-Boc-(amino)-ethyl bromide (P/N: Fluka, 17354, 2.978 g, 13.29 mmol) in DMF (30 mL), $K_2CO_3$ (3.4 g, 24.60 mmol) was added as solid and stirred for 20 h at ambient temperature. TLC analysis at this point showed the formation of a single product (41b) ($R_f$=0.33, silica plate, 1:1 EtOAc-hexanes; UV 254 nm, TLC was developed by heating with 3% (w/v) solution of ninhydrin in EtOH). After DMF removal under reduced pressure, the resulting oil was partitioned between EtOAc (350 mL) and dilute HCl (150 mL, 0.5 M). EtOAc layer was then washed with brine (100 mL×2), dried over $Na_2SO_4$ and concentrated to give a colorless oil. The oil was purified by flash-chromatography (CombiFlash purification system, 120 g column, 85 mL/min, 270 nm, 0-5 min 20% EtOAc in hexanes, then 80% EtOAc in hexanes, 18 mL fraction collected, fractions 24-30 had pure product) to give 2.02 g (93% yield) of product (41b). ES-MS (Direct infusion in MeOH, Calculated $[M+Na]^+=[C_{17}H_{27}N_3O_6+Na]^+$=392.18, observed $[M+Na]^+$=392.15.)

Compound (41c): To a solution of compound (41b) (1.10 g, 2.98 mmol) in THF (30 mL) NaOH solution (3.6 mL, 1 M) was added and stirred for 30 min. Solvent removed under reduced pressure and the residue, was treated with 95% TFA in water (20 mL) for 1 h at ambient temperature. TFA-water was removed under reduced pressure and the oil so obtained was dissolved in saturated $NaHCO_3$ (15 mL, pH=8-9) solution and FmocOSu (1.20 g, 3.58 mmol) was added as a solution in acetone (80 mL). The reaction mixture stirred for 19 h, when TLC analysis showed formation of single product (41c) ($R_f$=0.22; silica plate, 9:1:0.01 $CH_2Cl_2$—MeOH—AcOH, UV 254 nm, TLC was developed by heating with 3% (w/v) solution of ninhydrin in EtOH). The reaction mixture was then concentrated to remove acetone and the residue so obtained was diluted with water (100 mL). Non-polar impurities were removed by extraction with $Et_2O$ (100 mL×3). The aqueous layer was acidified (pH~1, HCl, 1 M) and extracted with $CH_2Cl_2$ (150 mL×3). The $CH_2Cl_2$ layer was dried over $Na_2SO_4$ and concentrated to give 1.41 g of product (41c) (98% yield) as white solid. ES-MS (MeOH-direct infusion) Calculated $[M+Na]^+=[C_{24}H_{23}N_3O_6+Na]^+$=472.15, Observed $[M+Na]^+$=472.09.

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP). Compound (41c) (10 eqv to Glu-Fib amount on the resin) was activated with HATU (P/N: Applied Biosystems 4317033, 9.5 eqv) and N,N-Diisopropylethylamine (30 eqv) in NMP (~1 mL), added to the resin and mixed for 30 min. Resin was then filtered, washed with NMP, and Fmoc group was cleaved. Piperazine acetic acid-TEA salt (10 eqv) then activated using HATU (9.5 eqv) and N,N-Diisopropylethylamine (60 eqv) in NMP (~1.5 mL) and added to the resin. After 30 min resin was washed with NMP followed by $CH_3CN$. Conjugated peptide was cleaved (and deprotected) from resin using 95:5 TFA-water (200 µL, 2 h) and precipitated using $Et_2O$. Analysis of compound (41) was performed using ES-MS (direct infusion in water, Calculated $[M+H]^+$=1919.9, Observed $[M+H]^+$=1920.3)

Further Mass Spectral Analysis:

MS/MS analyses of the Mass Tag labeled Glu-Fib peptide (41) were performed on MALDI and electrospray platforms. Data indicates that the Mass Tag is good candidate for MALDI and electrospray platform. Signature ion intensity was strong and desired peptide fragmentation pattern was observed (data not shown).

Figure 33:
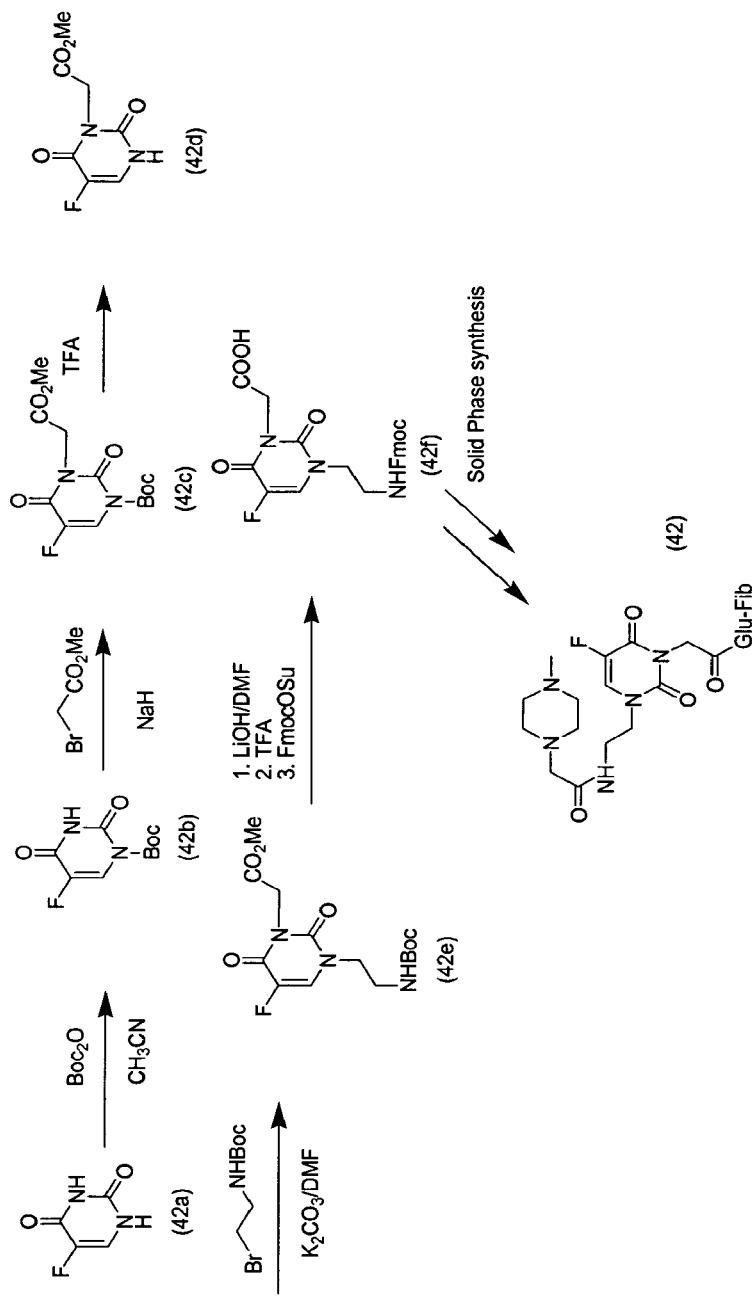
FIG. 33 illustrates the synthesis of Mass Tag labeled Glu-Fib peptide (42).

E. Synthesis of Mass Tag Libeled Glu-Fib Peptide (42) (See FIG. 33)

Compound (42b): To a solution of 5-Fluorouracil (42a) (P/N: Oakwood, 003241, 0.5 g, 3.84 mmol) and DMAP (46 mg, 0.384 mmol) in acetonitrile (25 mL), Di-tert-butyl dicarbonate (P/N: Chem-Impex, 00128, 0.835 g, 3.84 mmol) was added and stirred for 17 h at RT (RT stands for room temperature). TLC analysis showed formation of single product N-1-Boc-5-Fluorouracil (42b) ($R_f$=0.86, silica plate, 7:3 EtOAc-hexanes, UV 254 nm, Reference: Jaime-Figueroa, S.; Zamilpa, A.; Guzmán, A.; Morgans, D. J., "N-3-Alkylation of Uracil and Derivatives via N-1-Boc Protection", *Synthetic Communications*, 2001, 31, 3739-3746). The white solid obtained after removal of solvent was used in the next reaction without further purification.

Compound (42c): Compound (42b) (3.84 mmol) was dissolved in DMF (20 mL) and cooled to 0° C. To this solution NaH (184 mg, 4.60 mmol, 60% dispersion in oil) was added as solid and stirred for 30 mm at RT. At this point $BrCH_2COOMe$ (P/N: Acros, 16955, 0.437 mL, 4.60 mmol) was added and the reaction mixture stirred for 2 h at RT. TLC analysis showed formation of a new product ($R_f$=0.64, silica plate, 1:1 EtOAc-hexanes, UV 254 nm). Volatiles were removed using a rotary evaporator and the resulting oil was partitioned between EtOAc (250 mL) and HCl (0.5 M, 100 mL). EtOAc layer was then washed with brine (100 mL×2), dried over $Na_2SO_4$ and concentrated to a colorless oil. The oil was purified by flash-chromatography (CombiFlash purification system, 40 g column, 40 mL/min, 270 nm, gradient: 10-65% increment of EtOAc in hexanes over 25 min, 18 mL fraction collected, fractions 15-25 had pure product) to give 0.830 g (71% yield) of product 42c). ES-MS (Direct infusion in MeOH, Calculated $[M+Na]^+=[C_{12}H_{15}FN_2O_6+Na]^+$=325.08, observed $[M+Na]^+$=325.12.

Compound (42d): Compound (42c) (0.403 mg, 1.33 mmol) was treated with TFA-$CH_2Cl_2$ (1:1, 10 mL) solution for 15 min and the volatiles were removed to give compound (42d) (0.250 g, 93% yield, $R_f$=0.40, silica plate, 1:1 EtOAc-hexanes, UV 254 nm) as a white solid. ES-MS (Direct infusion in MeOH, Calculated $[M+H]^+=[C_7H_7FN_2O_4+H]^+$=203.05, observed $[M+H]^+$=203.09).

Compound (42e): To a solution of (42d) (0.250 g, 1.23 mmol) and $BrCH_2CH_2NHBoc$ (P/N: Fluka, 17354, 0.482 g, 2.15 mmol) in DMF (15 mL), $K_2CO_3$ (0.509 g, 3.69 mmol) was added as solid and the suspension stirred for 23 h at RT. TLC analysis showed the formation of a single product (42e) ($R_f$=0.28, silica plate, 1:1 EtOAc-hexanes, UV 254 nm, TLC was developed by heating with 3% (w/v) ninhydrin solution in EtOH). Solvents and volatiles were removed using a rotary evaporator and the resulting oil was partitioned between EtOAc (200 mL) and dilute HCl (100 mL, pH=3-4). EtOAc layer was then washed with brine (50 mL×2), dried over $Na_2SO_4$ and concentrated to a colorless oil. The oil was purified by flash-chromatography (CombiFlash purification system, 40 g column, 40 mL/min, 270 nm, gradient: 40-60% increment of EtOAc in hexanes over 25 min, 18 mL fraction collected, fractions 12-20 had pure product) to give 0.382 g (90% yield) of product (42e). ES-MS (Direct infusion in MeOH, Calculated $[M+Na]^+=[C_{14}H_{20}FN_3O_6+Na]^+$=368.12, observed $[M+Na]^+$=368.23.

Compound (42f: $LiOH.H_2O$ (55 mg, 1.32 mmol dissolved in 2 mL water) was added to a solution of (42e) (0.226 g, 0.66 mmol) in DMF (10 mL) and stirred for 20 min, when TLC analysis showed complete hydrolysis of methyl ester ($R_f$=0, silica plate, 1:1 EtOAc-hexanes, UV 254 nm, TLC was developed by heating with 3% (w/v) ninhydrin solution in EtOH). Volatiles were removed under reduced pressure and the residue was treated with TFA-water (9:1, 10 mL) for 1 h at RT. After removal of TFA-water, the residue was dissolved in saturated $NaHCO_3$ (30 mL, pH=8-9). A solution of Fmoc-OSu (P/N: Advance ChemTech RC8015, 0.268 g, 0.79 mmol in acetone (30 mL)) was then added to the aqueous solution and stirred for 1 hour at ambient temperature. TLC analysis showed formation of a product (42f) ($R_f$=0.20, silica plate, 9:1:0.01 $CH_2Cl_2$—MeOH—AcOH, UV 254 nm, TLC was developed by heating with 3% (w/v) solution of ninhydrin in EtOH). The reaction mixture was then concentrated to remove acetone and the residue so obtained was diluted with water (150 mL). Non-polar impurities were removed by extraction with $Et_2O$ (100 mL×2). The aqueous layer was acidified (pH~1, HCl, 1 M) and extracted with EtOAc (250 mL). EtOAc layer was washed with brine (50 mL×2), dried over $Na_2SO_4$ and concentrated to give 0.107 g (35% yield over three steps) of product (42f) as colorless viscous oil. ES-MS (MeOH-direct infusion) Calculated $[M+Na]^+$= $[C_{23}H_{20}FN_3O_6+Na]^+$=476.12, Observed $[M+Na]^+$476.20.

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP). Compound (42f) (10 eqv to Glu-Fib amount on the resin) was activated with HATU (P/N: Applied Biosystems 4317033, 9.5 eqv) and N,N-Diisopropylethylamine (30 eqv) in NMP (~1 mL), added to the resin and mixed for 30 min. Resin was then filtered, washed with NMP, and Fmoc group was cleaved. Piperazine acetic acid-TFA salt (10 eqv) was then activated using HATU (9.5 eqv) and N,N-Diisopropylethylamine (60 eqv) in NMP (~1.5 mL) and added to the resin. After 30 min the resin was washed with NMP followed by $CH_3CN$. Conjugated peptide was cleaved (and deprotected) from the resin using 95:5 TFA-water (200 μL, 2 h) and precipitated using $Et_2O$. Analysis of compound (42) was performed using ES-MS (direct infusion in water, Calculated $[M+H]^+$=1923.8, Observed $[M+H]^+$=1924.0)

Further Mass Spectral Analysis:

MS/MS analyses of the Mass Tag labeled Glu-Fib peptide (42) were performed on MALDI and electrospray platforms. Data indicates that the Mass Tag is good candidate for MALDI and electrospray platform. Signature ion intensity was strong and desired peptide fragmentation pattern was observed (data not shown).

Figure 34:
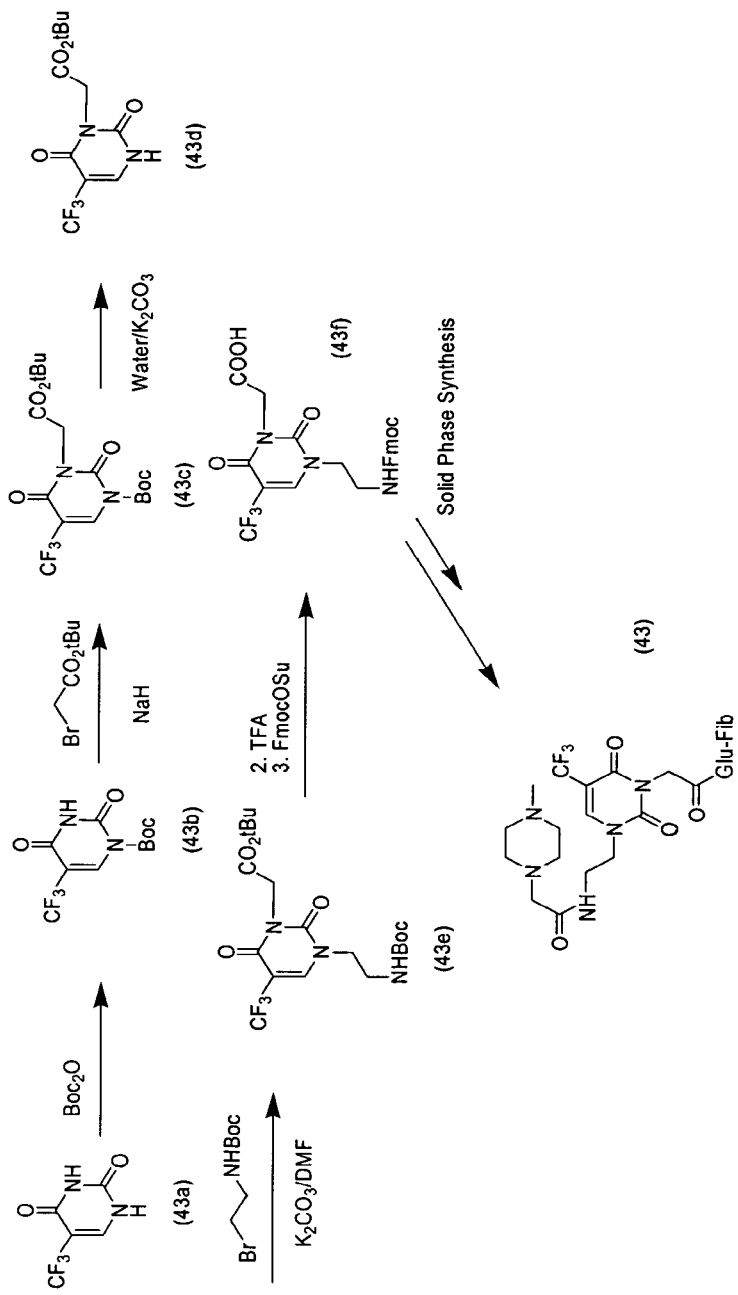
FIG. 34 illustrates the synthesis of Mass Tag labeled Glu-Fib peptide (43).
Figure 35:
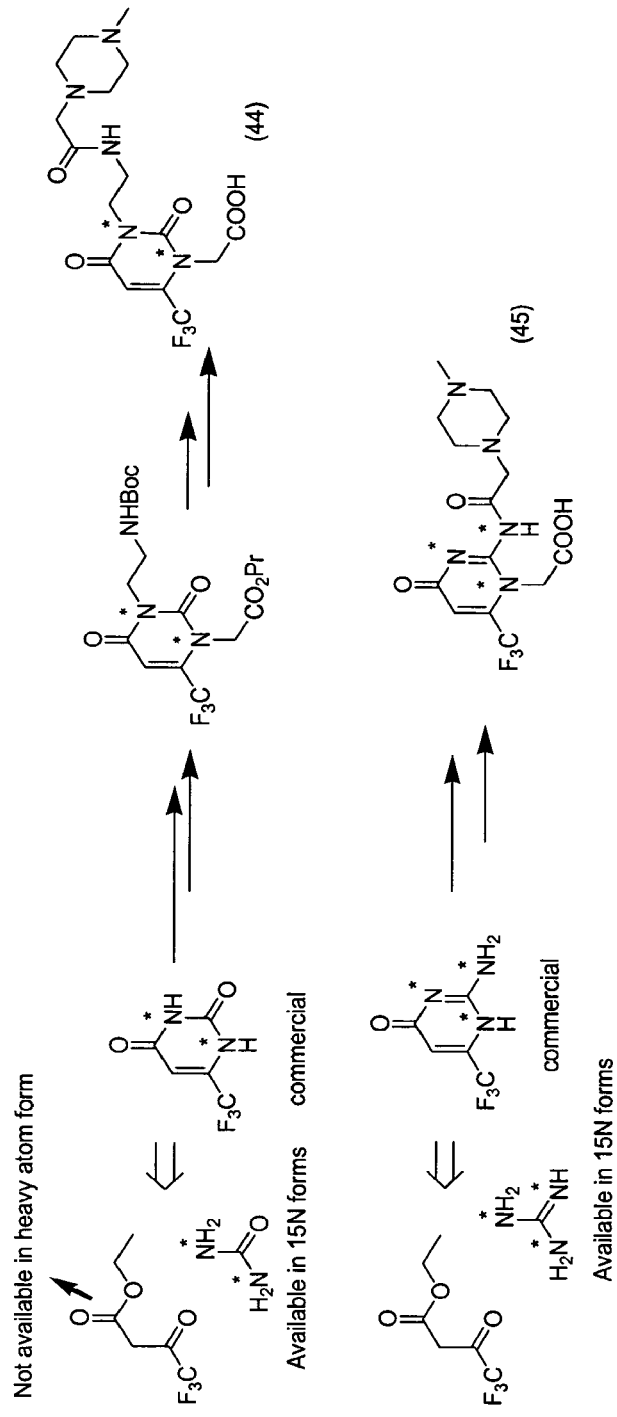
FIG. 35 illustrates the syntheses of Mass Tags (44) and (45).

F. Synthesis of Mass Tag Labeled Glu-Fib Peptide (43) (See FIG. 34)

Compound (43b): To a solution of (43a) (P/N: Oakwood, 003333, 1.0 g, 5.55 mmol) and DMAP (67 mg. 0.55 mmol) in acetonitrile (40 mL), Di-tert-butyl dicarbonate (P/N: Chem-Impex, 00128, 1.21 g, 5.55 mmol) was added and stirred for 2 h at RT. TLC analysis showed formation of single product (43b) ($R_f$=0.81, silica plate, 1:1 EtOAc-hexanes, UV 254 nm, Reference: Jaime-Figueroa, S.; Zamilpa, A.; Guzmán, A.; Morgans, D. J., "N-3-Alkylation of Uracil and Derivatives via N-1-Boc Protection", *Synthetic Communications*, 2001, 31, 3739-3746). White solid obtained after removal of solvent was used in next reaction without further purification.

Compound (43c): Compound (43b) (5.55 mmol) was dissolved in DMF (35 mL) and cooled to 0° C. To this solution NaH (267 mg, 6.66 mmol, 60% dispersion in oil) was added as solid and stirred for 30 min at RT. At this point $BrCH_2COO^tBu$ (P/N: Aldrich, 124230, 0.984 mL, 6.66 mmol) was added and the reaction mixture stirred for 1 h at RT. TLC analysis showed formation of one major product (43c) ($R_f$=0.60, silica plate, 1:4 EtOAc-hexanes, UV 254 nm). Volatiles were removed using a rotary evaporator and the resulting oil was partitioned between EtOAc (250 mL) and HCl (0.5 M, 100 mL). EtOAc was layer then washed with brine (50 mL×2), dried over $Na_2SO_4$ and concentrated to give colorless oil. The oil was purified by flash-chromatography (CombiFlash purification system, 120 g column, 85 mL/min, 270 nm, 25% EtOAc in hexanes, 18 mL fraction collected) to give 0.528 g (20% yield) of product (43c). ES-MS (Direct infusion in MeOH, Calculated $[M_2+Na]^+$=$[C_{32}H_{42}F_6N_4O_{12}+Na]^+$=811.26, observed $[M_2+Na]^+$=811.42

Compound (43d): Compound (43c) (0.528 g, 1.34 mmol) was treated with $TFA-CH_2Cl_2$ (1:9, 15 mL) solution for 5 min and the volatiles were removed to give compound (43d) (0.390 g, 99% yield, $R_f$=0.22, silica plate, 1:4 EtOAc-hexanes, UV 254 nm) as a white solid. ES-MS (Direct infusion in MeOH, Calculated $[M+Na]^+$=$[C_{11}H_{13}F_3N_2O_4+Na]^+$=317.07, observed $[M+Na]^+$=317.15.

Compound (43e): To a solution of (43d) (0.390 g, 1.32 mmol) and $BrCH_2CH_2NHBoc$ (P/N: Fluka, 17354, 1.112 g, 4.62 mmol) in DMF (15 mL) $K_2CO_3$ (1.094 g, 7.92 mmol) was added as solid and the suspension was stirred for 23 h at RT. TLC analysis showed the formation of a single product ($R_f$=0.70, silica plate, 1:1 EtOAc-hexanes, UV 254 nm, TLC was developed by heating with 3% (w/v) ninhydrin solution in EtOH). Volatiles were removed using a rotary evaporator and the resulting oil was partitioned between EtOAc (200 mL) and dilute-HCl (100 mL, pH=3-4). EtOAc layer was then washed with brine (50 mL×2), dried over $Na_2SO_4$ and concentrated to give a colorless oil. The oil was purified by flash-chromatography (CombiFlash purification system, 40 g column, 40 mL/min, 270 nm, 35% EtOAc in hexanes, 18 mL fraction collected, fractions 10-15 had pure product) to give 0.256 g (45% yield) of product (43e). ES-MS (Direct infusion in MeOH, Calculated $[M+Na]^+$=$[C_{18}H_{26}F_3N_3O_6+Na]^+$=460.17, observed $[M+Na]^+$=460.30.

Compound (43f): Compound (43e) (0.256 g, 0.59 mmol) was treated with TFA-water (95:5, 10 mL) and stirred for 1 h. Volatiles were removed under reduced pressure and the residue was washed with $Et_2O$. The white precipitate so obtained was dissolved in saturated $NaHCO_3$ (30 mL, pH=8-9). A solution of Fmoc-OSu (P/N: Advance ChemTech RC8015, 0.239 g, 0.71 mmol in acetone (2 mL)) was then added to the aqueous solution and stirred for 1 hour at ambient temperature. TLC analysis showed formation of a product (43f) ($R_f$=0.24; silica plate, 9:1:0.01 $CH_2Cl_2$—MeOH—AcOH, UV 254 nm, TLC was developed by heating with 3% (w/v) solution of ninhydrin in EtOH). The reaction mixture was then concentrated to remove acetone and the residue so obtained was diluted with water (150 mL). Non-polar impurities were removed by extraction with $Et_2O$ (100 mL×2). The aqueous layer was acidified (pH~1, HCl, 1 M) and extracted with EtOAc (250 mL×2). EtOAc layer was dried over $Na_2SO_4$ and concentrated to give 0.266 g of (43f) as white solid. ES-MS (MeOH-direct infusion) Calculated $[M+Na]^+$= $[C_{24}H_{20}F_3N_3O_6+Na]^+$=526.12, Observed $[M+Na]^+$526.20.

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP). Compound (43f) (10 eqv to Glu-Fib amount on the resin) was activated with HATU (P/N: Applied Biosystems 4317033, 9.5 eqv) and N,N-Diisopropylethylamine (30 eqv) in NMP (~1 mL), added to the resin and mixed for 30 min. Resin was then filtered, washed with NMP, and the Fmoc group was cleaved. Piperazine acetic acid-TFA salt (10 eqv) was then activated using HATU (9.5 eqv) and N,N-Diisopropylethylamine (60 eqv) in NMP (~1.5 mL) and added to the resin. After 30 min resin was washed with NMP followed by $CH_3CN$. Conjugated peptide was cleaved (and deprotected) from resin using 95:5 TFA-water (200 μL, 2 h) and precipitated using $Et_2O$. Analysis of compound (43) was performed using ES-MS (direct infusion in water, Calculated $[M+H]^+$=1973.8, Observed $[M+H]^+$=1974.0)

Further Mass Spectral Analysis:

MS/MS analyses of the Mass Tag labeled Glu-Fib peptide (43) were performed on MALDI and electrospray platforms. Data indicates that the Mass Tag is good candidate for MALDI and electrospray platform. Signature ion intensity was strong and desired peptide fragmentation pattern was observed (data not shown).

Figure 36:
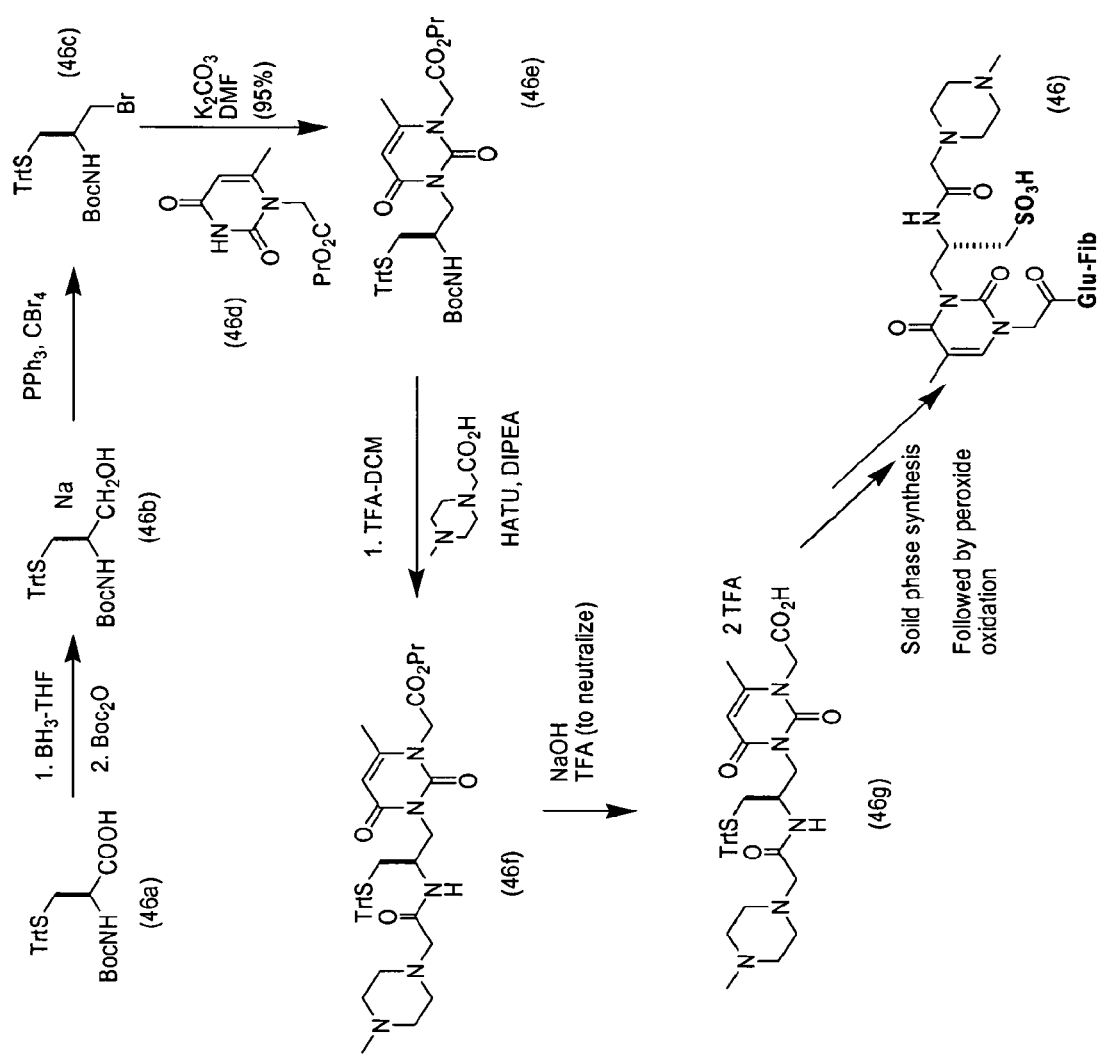
FIG. 36 illustrates the synthesis of Mass Tag labeled Glu-Fib peptide (46).

G. Synthesis of Mass Tag Labeled Glu-Fib Peptide (46) (See FIG. 36)

Compound (46b): To a solution of (46a) (P/N: Chem-Impex 01343, 2.73 g, 5.88 mmol) in THF (50 mL) at 0° C., $BH_3$.THF (14.7 mL, 1 M) solution was added and allowed to react for 18 h at RT. TLC analysis of a small aliquot (quenched with MeOH) showed formation of a new product and some Boc-deprotected product ($R_f$(46b)=0.50, silica plate, 1:1 EtOAc-hexanes, UV 254 nm, TLC was developed by heating with 3% (w/v) ninhydrin solution in EtOH, Boc deprotected product was identified from the base-line spot on TLC which was intensely ninhydrin positive (unlike compound (46a)). Reaction was quenched with MeOH, Di-tert-butyl dicarbonate (P/N: Chem-Impex, 00128, 1.28 g, 5.88 mmol) was added and stirred for 1 h at RT. TLC analysis at this stage showed the presence of compound (46b) only. Reaction mixture was concentrated and the resulting oil was purified by flash chromatography (CombiFlash purification system, 120 g column, 85 mL/min, 270 nm, 0-15 min 10% EtOAc in hexanes, then 60% EtOAc in hexanes, 18 mL fraction collected) to give 2.12 g (80% yield) of product (46b). ES-MS (MeOH-direct infusion) Calculated $[M+Na]^+=[C_{27}H_{31}NO_3S+Na]^+=472.19$, Observed $[M+Na]^+=472.17$.

Compound (46c): To a solution of (46b) (1.07 g, 2.38 mmol) and $CBr_4$ (P/N: Aldrich C11081, 1.18 g, 3.57 mmol) in $CH_2Cl_2$ (10 mL) $PPh_3$ solution (P/N: Aldrich T84409, 0.685 g, 2.39 mmol in 3 mL $CH_2Cl_2$) was added over 4 h at RT (using syringe pump). After completion of $PPh_3$ addition, the reaction was stirred for another 1 h. TLC showed formation of a major product (46c) ($R_f$=0.50, silica plate, 1:4 EtOAc-hexanes, UV 254 nm, TLC was developed by heating with 3% (w/v) ninhydrin solution in EtOH). Solvent was removed under reduced pressure and the oil was purified by flash chromatography (CombiFlash purification system, 120 g column, 85 mL/min, 270 nm, 0-5 min 5% EtOAc in hexanes, then 20% EtOAc in hexanes, 18 mL fraction collected) to give 0.690 g (56% yield) of product (46c). ES-MS (MeOH-direct infusion) Calculated $[M+Na]^+=[C_{27}H_{30}BrNO_2S+Na]^+=534.11$, Observed $[M+Na]^+=534.06$.

Compound (46e): To a solution of (46c) (0.461 g, 0.90 mmol) and (46d) (0.244 g, 1.08 mmol) in DMF (25 mL) solid $K_2CO_3$ (0.372 g, 2.70 mmol) was added and stirred for 68 h at RT. TLC showed presence of a product (46e) ($R_f$=0.50, silica plate, 1:1 EtOAc-hexanes, UV 254 nm, TLC was developed by heating with 3% (w/v) ninhydrin solution in EtOH), unreacted (46c) and (46d). After DMF removal under reduced pressure, the resulting oil was partitioned between EtOAc (200 mL) and dilute HCl (150 mL, 0.5 M). EtOAc layer was then washed with brine (50 mL×2), dried over $Na_2SO_4$ and concentrated to give colorless oil. The oil was purified by flash-chromatography (CombiFlash purification system, 40 g column, 40 mL/min, 265 nm, 0-1 min 20% EtOAc in hexanes, 1-10 min then 35% EtOAc in hexanes then 50% EtOAc in hexanes, 18 mL fraction collected, fractions 19-27 had pure product) to give 0.200 g (34% yield) of product (46e). ES-MS (Direct infusion in MeOH, Calculated $[M+Na]^+=[C_{37}H_{43}N_3O_6S+Na]^+=680.28$, observed $[M+Na]^+=680.23$.

Compound (46f): Compound (46e) (0.200 g, 0.304 mmol) was treated with TFA-$CH_2Cl_2$ (9:1, 10 mL) for 30 min at RT and then TFA-$CH_2Cl_2$ removed under reduced pressure. The yellow oil so obtained was co-evaporated with THF until the oil was colorless (re-tritylation of thiol group). The oil was then dissolved in DMF (5 mL) and basified with N,N-Diisopropylethylamine (P/N: Applied Biosystems 400136, pH 9-10, moist pH paper). N,N-Diisopropylethylamine (0.206 mL, 1.19 mmol) was added to a solution of N—Me-piperazine acetic acid•2TFA (0.152 g, 0.395 mmol) and HATU (Applied Biosystems, 4317033, 0.138 g, 0.364 mmol) in DMF (2 mL); mixed for 1 min and added to the above solution of Boc deprotected (46c). After 1 h the reaction mixture was acidified with HCl (1 M), diluted with brine (150 mL) and extracted with $CH_2Cl_2$ (150 mL). Dichloromethane layer was dried over $Na_2SO_4$ and concentrated to give 0.207 g of product (46f) as white foam (98%). ES-MS (Direct infusion in MeOH, Calculated $[M+H]^+$ $[C_{39}H_{47}N_5O_5S+H]^+=698.33$, observed $[M+H]^+=698.27$.

Compound (46 g): To a solution of (46f) (72 mg, 0.1 mmol) in THF-water (2:1, 3 mL) NaOH solution (0.20 mL, 1 M) was added and mixed for 30 min. Reaction was neutralized to pH=3 by TFA solution (1 M) and dried under vacuum to give product (46 g).

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP). Compound (46 g) (10 eqv to Glu-Fib amount on the resin) was activated with HATU (P/N: Applied Biosystems 4317033, 9.5 eqv) and N,N-Diisopropylethylamine (60 eqv) in NMP (~1 mL), added to the resin and mixed for 30 min. Resin was then filtered, and washed with NMP followed by $CH_3CN$. Conjugated peptide was cleaved (and deprotected) from resin using 95:5 TFA-water (200 μL, 2 h) and precipitated using $Et_2O$. To an ice cold solution of product peptide (1:5 $CH_3CN$-Water, 0.60 ml) per-formic acid solution (0.6 mL) was added and mixed at 0° C. for 5 min (Per-formic (HCOOOH) acid solution preparation: 4 mL HCOOH (99%)+0.45 mL $H_2O_2$ (30%)+0.25 mL water were mixed and allowed to stand for 1 h at RT). ES-MS analysis showed the presence of desired oxidized product (46). Calculated $[M+H]^+=2013.8$, observed $[M+H]^+=2013.7$.

Further Mass Spectral Analysis:

MS/MS analyses of the Mass Tag labeled Glu-Fib peptide (46) were performed on a MALDI platform. Data indicate that the Mass Tag is a good candidates for MALDI platform (data not shown). In MS analysis (electrospray) the amount of +3 charged species was much lower than in the case of only thymine nucleobase containing tags. This compound gave only 'y' ion series upon peptide fragmentation when analyzed on MALDI platform (data not shown)—thus substantially reducing the complexity of the MS/MS spectra for analysis.

Figure 37:
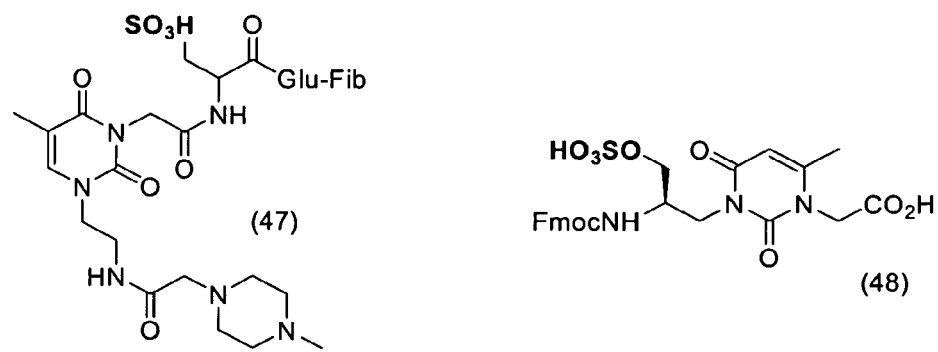
FIG. 37 illustrates the chemical structures of Mass Tag labeled Glu-Fib peptide (47) and Mass Tag (48)

G. Synthesis of Mass Tag Labeled Glu-Fib Peptide (47) (See FIG. 37)

To a solution of cysteic acid (P/N: TCI America CO514, 1 g, 5.90 mmol) in aq $NaHCO_3$ (pH=8-9, ~50 mL) Fmoc-OSu solution (2.4 g, 7.08 mmol in 150 mL acetone) was added and stirred for 18-19 h at RT. Acetone was removed under reduced pressure and the suspension was diluted with 150 mL of water. Non-polar impurities were removed by extraction with $Et_2O$ (100 mL×3). Aqueous layer was acidified with conc. HCl to pH 1 and then Amberlite IR-120-H resin (P/N: Aldrich 216534, 12 g, 1.9 mmol/g —$SO_3H$ group) was added, mixed and filtered. Filtrate was lyophilized to give 2.52 g of Fmoc-cysteic-acid as white hygroscopic solid. ES-MS (Direct infusion in water, negative mode, Calculated $[M-H]^-=[C_{18}H_{17}NO_7S-H]^-=390.06$, observed $[M-H]^-=390.03$.

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP).

Fmoc-cysteic-acid (10 eqv to Glu-Fib amount on the resin) was individually activated with HATU (P/N: Applied Biosystems 4317033, 9.5 eqv) and N, N-Diisopropylethylamine (30 eqv) in NMP (~1 mL), added to the resin and mixed for 30 min. Resin was then filtered, washed with NMP, and Fmoc group was cleaved. Piperazine acetic acid-TFA salt (10 eqv) was then activated using HATU (9.5 eqv) and N,N-Diisopropylethylamine (60 eqv) in NMP (~1.5 mL), and added to the resin. After 30 min the resin was washed with NMP followed by $CH_3CN$. Conjugated peptide was cleaved (and deprotected) from resin using 95:5 TFA-water (200 µL, 2 h) and precipitated using $Et_2O$. Analysis of compound (47) was performed using ES-MS (direct infusion in water, Calculated $[M+H]^+$=2070.9, Observed $[M+H]^+$=2071.8)

Further Mass Spectral Analysis:

MS/MS analyses of the Mass Tag labeled Glu-Fib peptide (47) were performed on a MALDI platform. Data indicate that the Mass Tag is a good candidate for MALDI platform (data not shown). In MS analysis (electrospray) the amount of +3 charged species was much lower than in the case of only thymine nucleobase containing tags. This compound gave only 'y' ion series upon peptide fragmentation when analyzed on MALDI platform (data not shown)—thus substantially reducing the complexity of the MS/MS spectra for analysis.

Figure 38:
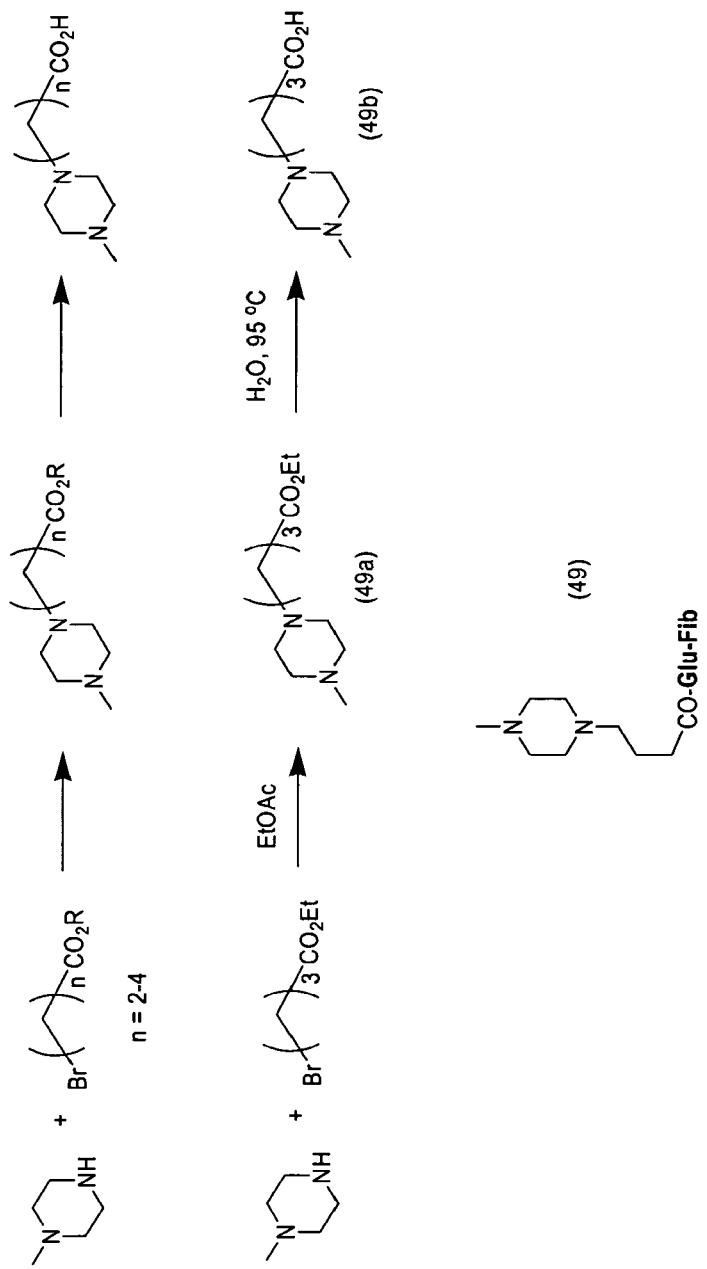
FIG. 38 illustrates the synthesis of Mass Tag labeled Glu-Fib peptide (49).

H. Synthesis of Mass Tag Labeled Glu-Fib Peptide (49) (See FIG. 38)

To a solution of $Br(CH_2)_3CO_2Et$ (P/N: Aldrich 167118, 0.645 mL, 4.5 mmol) in EtOAc (20 mL) 1-Methyl piperazine (P/N: Aldrich 130001, 1 mL, 9.0 mmol) was added and stirred overnight. After filtration of the precipitate, EtOAc layer was concentrated and the oil so formed was purified by flash chromatography (CombiFlash purification system, 12 g silica column, 30 mL/min, 20% methanol in $CH_2Cl_2$, 18 mL fraction collected) to give product (49a). Product (49a) was dissolved in water (4 mL) and heated at 95° C. for 4 h. After removal of water the solid (49b) was washed with THF and dried under vacuum. ES-MS (Direct infusion in water, Calculated $[M+H]^+$=$[C_9H_{18}N_2O_2+H]^+$=187.14, observed $[M+H]^+$=187.18.

Approximately 10 mg of Fmoc-Glu-Fib-Trityl-chloride resin was treated with 20% (v/v) piperidine in DMF (2 mL×1 min, filtered, then 2 mL×5 min), filtered and washed (NMP). Compound (49b) (10 eqv to Glu-Fib amount on the resin) was activated with HATU (P/N: Applied Biosystems 4317033, 9.5 eqv) and N,N-Diisopropylethylamine (30 eqv, 60 eqv for compound 21) in NMP (~1 mL), added to the resin and mixed for 30 min. Resin was then filtered, washed with NMP followed by $CH_3CN$. Conjugated peptide was cleaved (and deprotected) from resin using 95:5 TFA-water (200 µL, 2 h) and precipitated using $Et_2O$. Analysis of compound (50) was performed using ES-MS (direct infusion in water, Calculated $[M+H]^+$=1738.8, Observed $[M+H]^+$=1739.2)

Further Mass Spectral Analysis:

MS/MS analyses of the Mass Tag labeled Glu-Fib peptide (49) was performed on MALDI and electrospray platforms. Data indicate that propionic acid derivative (49) could be a suitable candidate (data not shown). However a close analysis of the MS/MS pattern revels presence of some peptide fragments in which part of the tag was still attached.

The foregoing synthetic methods could be applied to the preparation of isotopically coded labeling reagents by the incorporation of starting materials comprising heavy atom isotopes. The following examples demonstrate various methods for generating isotopically encoded isobaric labeling reagents.

Syntheses of Isobaric Mass Tags (Labeling Reagents)

I. Isobaric Mass Tags Isotopically Coded with Deuterium Isotopes.

A. Synthesis of Mass Tag (25)

FIG. 20 Illustrates the Synthesis of Mass Tag (25).

FmocSer(Bzl) (1 mmol), TSTU (1 mmol), and DIEA (2 mmol) were dissolved in DMF (6 mL). The mixture was shaken at room temperature for half an hour. The solvent was evaporated to form FmocSer(Bzl)-OSu, which was used directly in the following steps.

To a solution of glycine (0.4 mmol) in DMF (0.8 ml) and 0.2 M aqueous sodium bicarbonate (2.8 ml) was added Fmoc-Ser(Bzl)-OSu (0.4 mmol) in DMF (2.4 ml) while vortexing. The mixture was shaken at room temperature for 20 minutes. The compound, FmocSer(Bzl)-Gly, was purified with preparative HPLC.

FmocSer(Bzl)-Gly (50 mg) was exposed to 20% piperidine in DMF (5 ml) for 10 minutes to remove the Fmoc-protecting group. After evaporation of solvents, the product, Ser(Bzl)-Gly, was purified with preparative HPLC, and characterized with MS ($[M+H]^+$: 253.1, calculated; 253.0, found).

FmocGlycine-2,2-$d_2$(ISOTEC, 0.14 mmol), TSTU (0.21 mmol), and DIEA (0.28 mmol) were dissolved in DMF (1 ml). The mixture was shaken at room temperature for 45 minutes, and then transferred to a solution of Ser(Bzl)-Gly (0.14 mmol) in 0.2 M aqueous sodium bicarbonate (2 ml). More DMF (1 ml) was added. The mixture was shaken at room temperature for 20 minutes. The compound, FmocGly($d_2$)-Ser(Bzl)-Gly, was purified with preparative HPLC, and characterized with MS ($[M+H]^+$: 534.2, calculated; 534.2, found).

FmocGly($d_2$)-Ser(Bzl)-Gly was exposed to 20% piperidine in DMF (5 ml) for 15 minutes to remove the Fmoc-protecting group. After evaporation of solvents, the compound, Gly($d_2$)-Ser(Bzl)-Gly, was purified with preparative HPLC, and characterized with MS ($[M+H]^+$: 312.1, calculated; 312.0, found).

Gly($d_2$)-Ser(Bzl)-Gly was acylated using Protocol I to furnish Mass Tag (25) ($[M+H]^+$: 480.1, calculated; 480.0, found).

B. Synthesis of Mass Tag (26)

Figure 21:
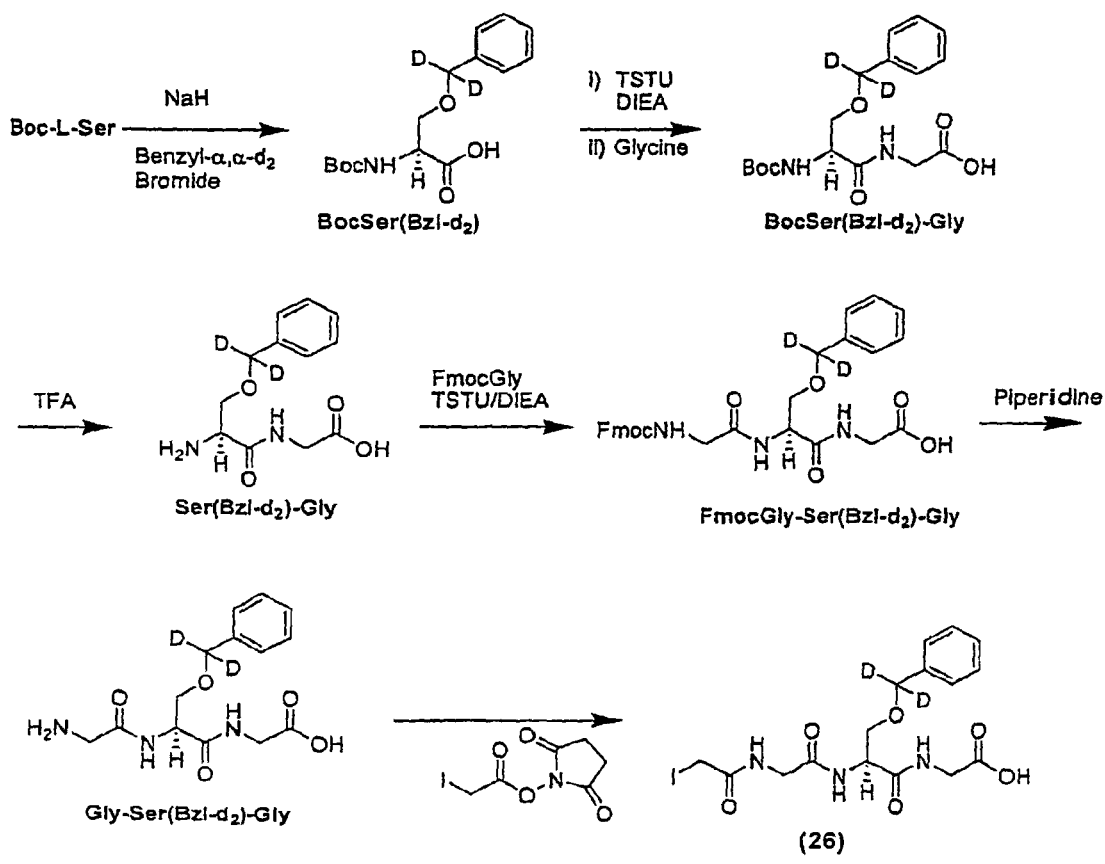
FIG. 21 illustrates the synthesis of Mass Tag (26).

FIG. 21 Illustrates the Synthesis of Mass Tag (26).

A solution of Boc-L-Ser (NovaBichem, 2 mmol) in DMF (4 ml) was cooled with an ice-water bath. Sodium hydride (Aldrich, 6 mmol) was added. After the evolution of hydrogen gas ceased, benzyl-α,α-$d_2$ bromide (ISOTEC, 2 mmol) was added while vortexing. The mixture was shaken at room temperature for 5 hours. The product, BocSer(Bzl-$d_2$), was purified with preparative HPLC, and characterized with MS ($[M+H]^+$: 298.2, calculated; 298.2, found).

BocSer(Bzl-$d_2$) (0.4 mmol), TSTU (0.6 mmol), and DIEA (0.8 mmol) were dissolved in DMF (2 ml). The mixture was shaken at room temperature for 1 hour, and then transferred dropwise to a solution of glycine (2 mmol) in 3 mL of 1M aqueous sodium bicarbonate. The mixture was shaken at room temperature for 30 minutes. The product, BocSer(Bzl-$d_2$)-Gly, was purified with preparative HPLC, and characterized with MS ($[M+H]^+$: 355.3, calculated; 355.2, found).

BocSer(Bzl-$d_2$)-Gly (64 mg) was exposed to a solution of trifluoroacetic acid (TFA, Applied Biosystems, 1 ml) and methylene chloride (2 ml) at room temperature for 30 minutes to remove the Boc-protecting group. The mixture was extracted with water twice (1.5 ml each). The extracts were combined, and purified with preparative HPLC. The product, Ser(Bzl-$d_2$)-Gly, was characterized with MS ([M+H]$^+$: 255.1, calculated; 255.2, found).

FmocGly (0.3 mmol), TSTU (0.3 mmol), and DIEA (0.45 mmol) were dissolved in DMF (2 ml). The mixture was shaken at room temperature for 1 hour, and then transferred dropwise to a solution of Ser(Bzl-$d_2$)-Gly in 0.2 M in aqueous sodium bicarbonate (2 ml). More DMF (1 ml) was added. The mixture was shaken at room temperature for 20 minutes. The product, FmocGly-Ser(Bzl-$d_2$)-Gly, was purified with preparative HPLC, and characterized with MS ([M+H]$^+$: 534.3, calculated; 534.4, found).

FmocGly-Ser(Bzl-$d_2$)-Gly was exposed to a solution of 5 ml of 20% piperidine in DMF at room temperature for 10 minutes to remove the Fmoc-protecting group. After evaporation of solvents, the product, Gly-Ser(Bzl-$d_2$)-Gly, was purified with preparative HPLC, and characterized with MS ([M+H]$^+$: 312.2, calculated; 312.4, found).

Gly-Ser(Bzl-$d_2$)-Gly was acylated using Protocol I to furnish Mass Tag (26) ([M+H]$^+$: 480.1, calculated; 480.2, found).

II. Isobaric Mass Tags Isobarically Coded with $^{12}$C/$^{13}$C and $^{14}$N/$^{15}$N A. Synthesis of Mass Tag (27)

FIG. 22 Illustrates the Synthesis of Mass Tag (27).

FmocGly($^{13}$C$_2$, $^{15}$N) (ISOTEC, 0.33 mmol), TSTU (0.66 mmol) and DIEA (0.66 mmol) were dissolved in DMF (2 ml). The mixture was shaken at room temperature for 40 minutes, and then transferred dropwise to a solution of L-Serine(Bzl) (NovaBiochem, 2 mmol) in DMA (4 mmol), DMSO (8 ml) and water (2 ml) while vortexing. The mixture was shaken at room temperature for 20 minutes. After filtration, the filtrate, which contained the product, was purified with preparative HPLC. The product, FmocGly($^{13}$C$_2$, $^{15}$N)-Ser(Bzl), was characterized with MS ([M+H]$^+$: 478.2, calculated; 478.2, found).

FmocGly($^{13}$C$_2$, $^{15}$N)-Ser(Bzl), TSTU (0.6 mmol) and DIEA (0.6 mmol) were dissolved in DMF (2 ml). The mixture was shaken at room temperature for 1 hour, and transferred dropwise to a solution of Gly($^{13}$C$_2$, $^{15}$N) (ISOTEC, 1 mmol) in water (2 ml) with sodium bicarbonate (2 mmol) while vortexing. More DMF (4 ml) was added. The mixture was shaken at room temperature for 30 minutes. After centrifugation, the supernatant, which contained the product, was purified with preparative HPLC. The product, FmocGly($^{13}$C$_2$, $^{15}$N)-Ser(Bzl)-Gly($^{13}$C$_2$, $^{15}$N), was characterized with MS ([M+H]$^+$: 538.2, calculated; 538.2, found).

FmocGly($^{13}$C$_2$, $^{15}$N)-Ser(Bzl)-Gly($^{13}$C$_2$, $^{15}$N) (4 mg) was exposed to 0.2 ml of 20% piperidine in DMF at room temperature for 10 minutes to remove the Fmoc-protecting group. After removal of all the solvents, the deprotected amine was acylated using Protocol I to furnish Mass Tag (27) ([M+H]$^+$: 484.1, calculated; 484.0, found).

B. Synthesis of Mass Tag (28)

Figure 23:
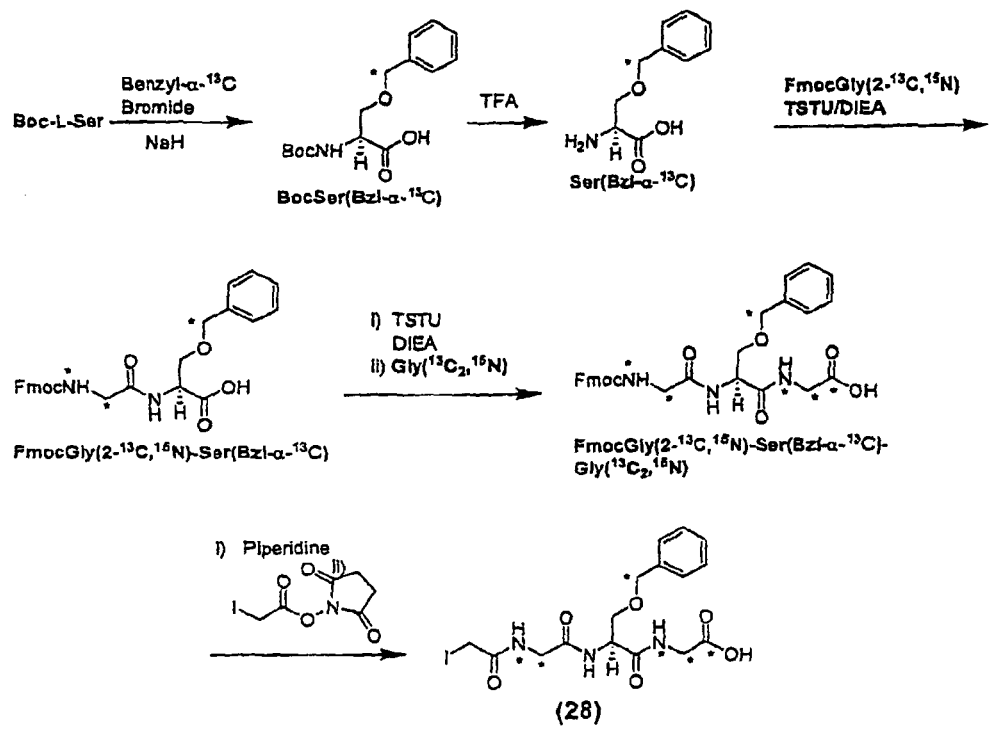
FIG. 23 illustrates the synthesis of Mass Tag (28).

FIG. 23 Illustrates the Synthesis of Mass Tag (28).

Boc-L-Ser (NovaBiochem, 5.82 mmol) was dissolved in DMF (6 ml), and cooled with an ice-water bath. Sodium hydride (17.46 mmol) was added while vortexing. The mixture was shaken at room temperature for 15 minutes. After no more gas was released, benzyl ($\alpha$-$^{13}$C) bromide (ISOTEC, 2.91 mmol) was added while vortexing. The mixture was shaken at room temperature for 4 hours, and then purified with preparative HPLC. The product, BocSer(Bzl-$\alpha$-$^{13}$C), was characterized with MS ([M+H]$^+$: 297.1, calculated; 297.2, found).

BocSer(Bzl-$\alpha$-$^{13}$C) (300 mg) was deprotected with 10 ml of 30% TFA in methylene chloride for 30 minutes, and then extracted with water twice (3 mL each). The aqueous layers were combined, and purified with preparative HPLC. The product, Ser(Bzl-$\alpha$-$^{13}$C), was characterized with MS ([M+H]$^+$: 197.1, calculated; 197.0, found).

FmocGly(2-$^{13}$C, $^{15}$N) (ISOTEC, 1 mmol), TSTU (2 mmol) and DIEA (2 mmol) were dissolved in DMF (3 ml). The mixture was shaken at room temperature for 1 hour, and then transferred to Ser(Bzl-$\alpha$-$^{13}$C) in 3 ml of 0.2 M aqueous sodium bicarbonate solution while vortexing. The mixture was shaken at room temperature for 20 minutes, and purified with preparative HPLC. The product, FmocGly(2-$^{13}$C, $^{15}$N)-Ser(Bzl-$\alpha$-$^{13}$C), was characterized with MS ([M+H]$^+$: 478.2, calculated; 478.2, found).

FmocGly(2-$^{13}$C, $^{15}$N)-Ser(Bzl-$\alpha$-$^{13}$C) (0.021 mmol), TSTU (0.042 mmol) and DIEA (0.042 mmol) were dissolved in DMF (0.5 ml). The mixture was shaken at room temperature for 1 hour, and transferred to Glycine($^{13}$C$_2$, $^{15}$N) (ISOTEC, 0.1 mmol) in 0.5 ml of 0.2 M aqueous sodium bicarbonate solution. The mixture was shaken at room temperature for 20 minutes, and purified with preparative HPLC. The product, FmocGly(2-$^{13}$C, $^{15}$N)-Ser(Bzl-$\alpha$-$^{13}$C)-Gly($^{13}$C$_2$, $^{15}$N), was characterized with MS ([M+H]H$^+$: 538.2, calculated; 538.0, found).

FmocGly(2-$^{13}$C, $^{15}$N)-Ser(Bzl-$\alpha$-$^{13}$C)-Gly($^{13}$C$_2$, $^{15}$N) (12 mg) was deprotected with 0.8 ml of 20% piperidine in DMF at room temperature for 10 minutes. After evaporation of all the solvents, the free amine was acylated using Protocol I to furnish Mass Tag (28) ([M+H]$^+$: 484.1, calculated; 484.0, found).

Solid Supports with Isobaric Mass Tags

I. Synthesis of FmocGly-Ser(Bzl-$^{13}$C$_6$)

Figure 24:
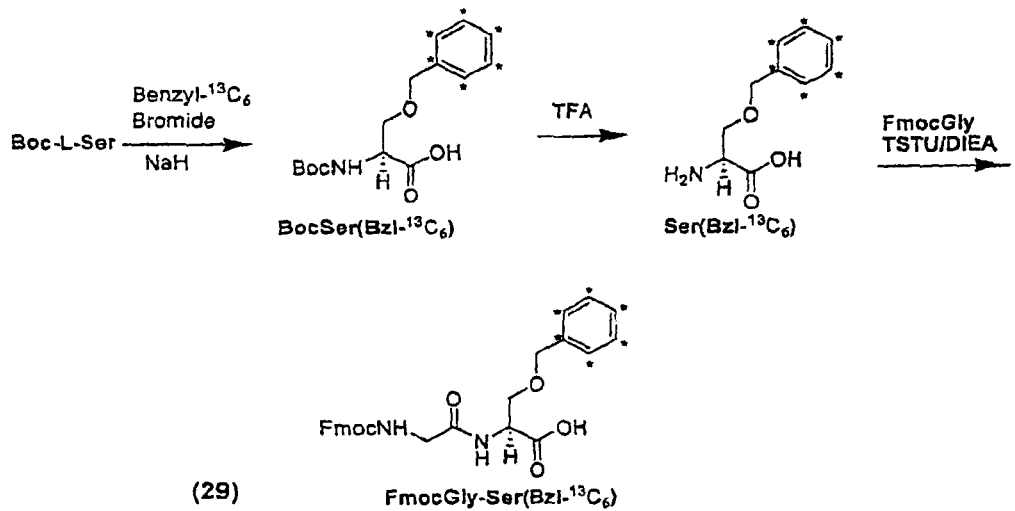
FIG. 24 illustrates the synthesis of FmocGly-Ser(Bzl-$^{13}C_6$)(29)

FIG. 24 Illustrates the Synthesis of FmocGly-Ser(Bzl-$^{13}$C$_6$) (29)

The compound was prepared with the same procedures as those for preparing. FmocGly(2-$^{13}$C, $^{15}$N)-Ser(Bzl-$\alpha$-$^{13}$C) ([M+H]$^+$ in MS: 481.2, calculated; 481.2, found) (see: Syntheses of Isobaric Mass Tags Isotopically Coded with heavy atom isotopes, §IIB).

II. Syntheses of Resin Bound Mass Tags

Figure 25:
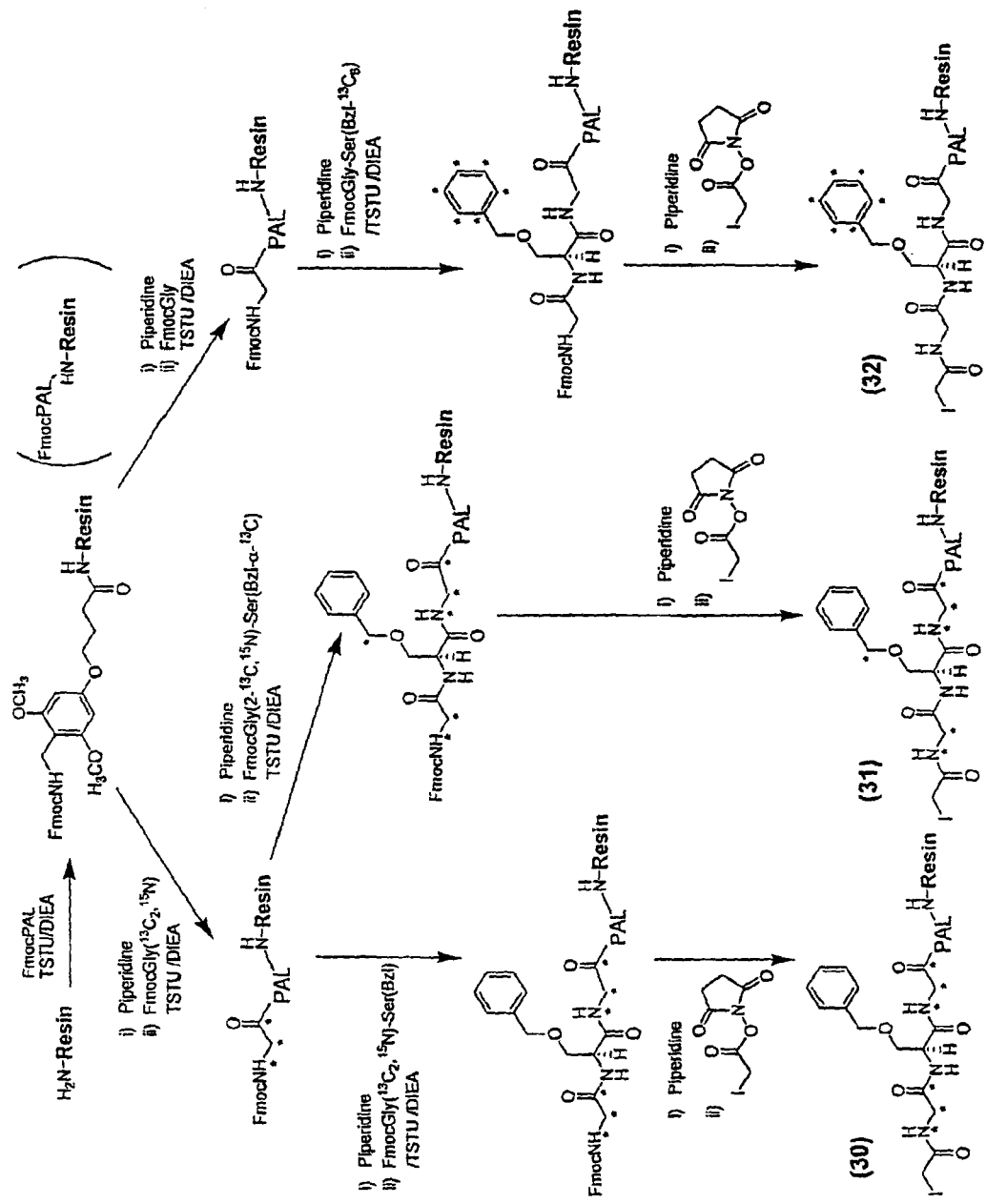
FIG. 25 illustrates the syntheses of resin bound Mass Tags (30), (31) and (32).

FIG. 25 Illustrates the Syntheses of Resin Bound Isobaric Isotopically Coded Mass Tags (30), (31) and (32).

A. Synthesis of Resin Bound Isobaric Isotopically Coded Mass Tag (30)

1 g of wet amino PEGA resin (NovaBiochem, 0.05 mmol substitution) was washed with water, DMF, DCM, methanol, DCM and DMF. The resin was typically washed twice with each solvent (approximately 5 ml of each). FmocPAL linker (Applied Biosystems, 0.15 mmol), TSTU (0.15 mmol) and DIEA (0.225) were dissolved in DMF (1 ml). The mixture was shaken at room temperature for 20 minutes, and then transferred to the resin suspended in around 1 ml of DMF. The mixture was shaken at room temperature for 1 hour. After filtration, the resin was washed twice with DMF, DCM, methanol, DCM and DMF.

The resin was washed with 5 ml of 20% piperidine in DMF once, and then fully deprotected with 5 ml of 20% piperidine at room temperature for 10 minutes. After filtration, the resin was washed twice with DMF, DCM, methanol, DCM and DMF.

FmocGly($^{13}$C$_2$, $^{15}$N) (ISOTEC, 0.1 mmol), TSTU (0.1 mmol) and DIEA (0.15 mmol) were dissolved in DMF (1 ml). The mixture was shaken at room temperature for 20 minutes, and then transferred to the resin suspended in approximately 1 ml of DMF. The mixture was shaken at room temperature for 2 hours. After filtration, the resin was washed twice with DMF, DCM, methanol, DCM and DMF.

The resin was washed with 5 ml of 20% piperidine in DMF once, and then fully deprotected with 5 ml of 20% piperidine at room temperature for 10 minutes. After filtration, the resin was washed twice with DMF, DCM, methanol, DCM and DMF.

FmocGly($^{13}C_2$, $^{15}N$)-Ser(Bzl) (0.1 mmol), HBTU/HOBT (Applied Biosystems, 0.1 mmol) and DIEA (0.15 mmol) were dissolved in DMF (1 ml). The mixture was shaken at room temperature for 2 hours. After filtration, the resin was washed twice with DMF, DCM, methanol, DCM and DMF.

The resin was washed with 5 ml of 20% piperidine in DMF once, and then fully deprotected with 5 ml of 20% piperidine at room temperature for 10 minutes. After filtration, the resin was washed twice with DMF, DCM, methanol, DCM and DMF.

Iodoacetic acid (0.15 mmol) and N-hydroxysuccinimide (0.15 mmol) were dissolved in DMF (0.5 ml). DCC (Aldrich, 0.15 mmol) in DMF (0.5 ml) was added while vortexing. The mixture was shaken at room temperature for 1 hour. After filtration, the solution was added to the resin suspended in 1 ml DMF with sodium bicarbonate (0.15 mmol). The mixture was shaken at room temperature for 1 hour. After filtration, resin bound Mass Tag (30) was washed twice with water, DMF, DCM, methanol, DCM, DMF and DCM. The resin bound mass tag was split into equal portions within cartridges (Millipore UFC3OLG25), dried with a SpeedVac, and stored in a freezer (−30° C.) for future uses. Each cartridge had around 4 mg of dry resin bound Mass Tag (30).

B. Synthesis of Resin Bound Isobaric Isotopically Coded Mass Tag (31)

The procedure for synthesizing resin bound Mass Tag (31) was same as that for synthesizing resin bound Mass Tag (30), except that FmocGly($^{13}C_2$, $^{15}N$)-Ser(Bzl) was replaced with FmocGly(2-$^{13}C$, $^{15}N$)-Ser(Bzl-α-$^{13}C$).

C. Synthesis of Resin Bound Isobaric Isotopically Coded Mass Tag (32)

The procedure for synthesizing resin bound Mass Tag (31) was same as that for synthesizing resin bound Mass Tag (30), except that FmocGly($^{13}C_2$, $^{15}N$) and FmocGly($^{13}C_2$, $^{15}N$)-Ser(Bzl) were replaced with FmocGlycine and FmocGly-Ser(Bzl-$^{13}C_6$), respectively.

Figure 26:
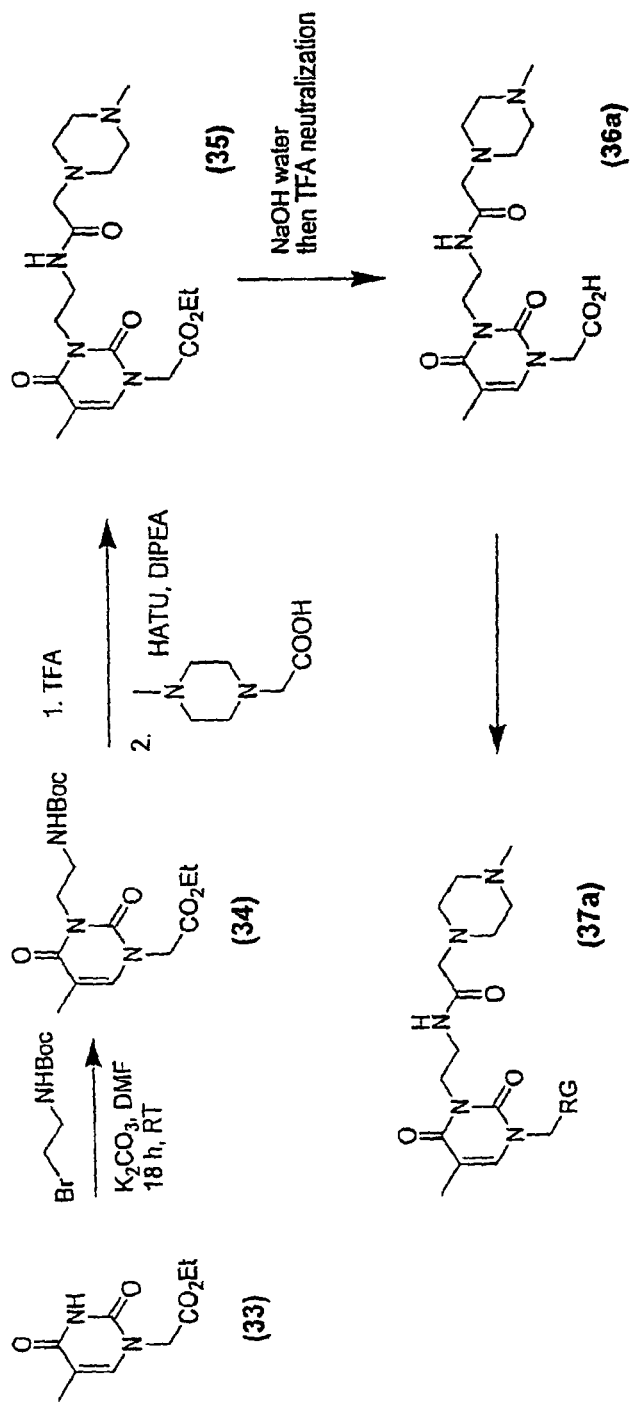
FIG. 26 illustrates the synthesis of a labeling reagent/mass tag (XX) ((37a)) comprising a thymine nucleobase.

Synthesis of Nucleobase Comprising Labeling Reagents: FIG. 26 illustrates the incorporation of the nucleobase (thymine) into Mass Tag (36a) starting from compound (33) and proceeding through intermediate compounds (34) and (35). A procedure for such conversion was performed and is described as follows:

Synthesis of Compound (34):

To a solution of thymine acetic acid ethyl ester (33) (500 mg, 2.35 mmol) and 2-Boc-(amino)-ethyl bromide (634 mg, 2.82 mmol) in DMF (50 mL), was added $K_2CO_3$ (974 mg, 7.05 mmol). The reaction was stirred for 18 h at ambient temperature. Thin layer chromatography (TLC) analysis indicated the formation of a single product (Silica plate, EtOAc solvent; $R_f$=0.7; UV, ninhydrin). After the DMF was removed under reduced pressure, the product was purified by flash chromatography (ISCO Companion purification system; 40 g $SiO_2$ column, detection at 260 nm, Flow=40 mL/min; 0-7 min 50% EtOAc in hexanes to remove unreacted 2-Boc-(amino)-ethyl bromide, then 100% EtOAc to elute the product). ES-MS (Direct infusion in methanol) [M+H]$^+$ 356.18 calculated, 356.18 found).

Note: Compound (33) can be prepared according to: "Building blocks for polyamide nucleic acids: Facile synthesis using potassium fluoride doped natural phosphate as basic catalyst. Alahiane, A.; Taourirte, M.; Rochdi, A.; Redwane, N.; Sebti, S.; Engels, J. W.; Lazrek, H. B. Nucleosides, Nucleotides & Nucleic Acids (2003), 22(2), 109-114", the entire teachings of which are incorporated herein by reference for all purposes.

Synthesis of Compound 35:

Compound (34) (465 mg, 1.3 mmol) was treated with 90% TFA in dichoromethane (DCM) for 30 min at ambient temperature, when TLC analysis showed complete Boc deprotection. The TFA-DCM solution was removed under reduced pressure and the foam so obtained was dissolve in DMF (25 mL). The solution was then neutralized by addition of diisopropylethylamine (checked with moist pH paper). To this neutral solution was added a mixture of piperazine acetic acid (206 mg, 1.3 mmol), HATU (494 mg, 1.3 mmol) and diisopropylethylamine (0.679 mL, 3.9 mmol) in DMF (25 mL). After 30 minutes, TLC analysis indicated the formation of product (Silica plate, EtOAc-MeOH (1:1) solvent; $R_f$=0.2; UV, ninhydrin). After DMF removal under reduced pressure, the product was purified by flash chromatography (ISCO Companion purification system; 40 g $SiO_2$ column, detection at 260 nm, Flow=40 mL/min; 0-1 min 95% EtOAc in MeOH, 1-10 min 50% EtOAc in MeOH, 10-30 min 10% EtOAc in MeOH). ES-MS (Direct infusion in water) [M+H]$^+$396.22 calculated, 396.28 found).

Synthesis of Compound (36a):

To a solution of compound (35) (300 mg, 0.76 mmol) in water (20 mL) was added NaOH solution (1.14 mL, 1N). The solution was stirred for 3 h at ambient temperature. TLC analysis indicated completion of ethyl ester hydrolysis. The reaction mixture was then acidified with TFA and then concentrated under reduced pressure. The oil so obtained was used directly without any further purification. ES-MS (Direct infusion in water) [M+Na]$^+$390.18 calculated, 390.40 found).

Synthesis of Compound (37a):

Compound (37a), which comprises a reactive group RG, can be prepared by well known methods discussed in the section entitled "The Reactive Group."

Figure 27:
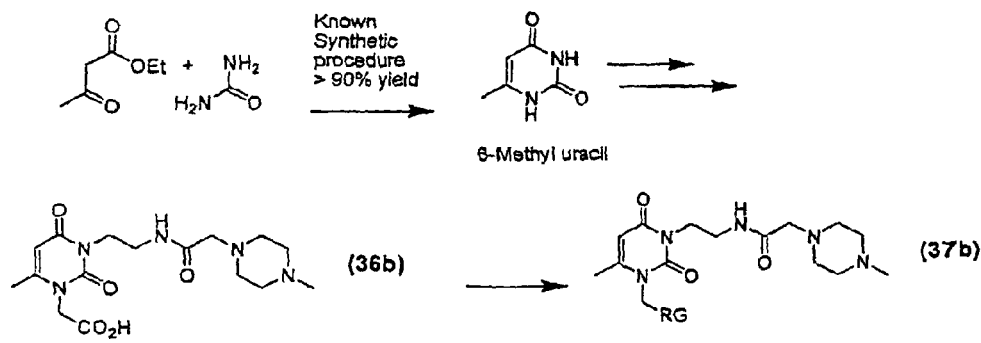
FIG. 27A illustrates a known procedure for the synthesis of 6-methyl uracil from which a labeling reagent (mass tag) comprising the 6-methyl uracil nucleobase ((37b)) can be prepared.
FIG. 27B illustrates various commercially available isotopically substituted versions of ethyl acetoacetate that can be used in the preparation of isotopically enriched versions of 6-methyl uracil.
FIG. 27C illustrates various commercially available isotopically substituted versions of urea that can be used in the preparation of isotopically enriched versions of 6-methyl uracil.
Figure 27:
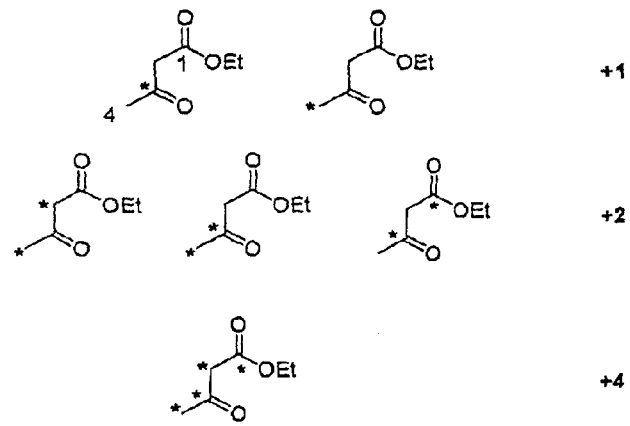
Figure 27:
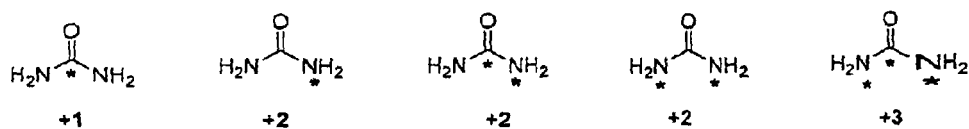

Preparation of other labeling reagents comprising nucleobases & methods for isotopically coding said labeling reagents: FIG. 27A illustrates a known synthetic procedure for the synthesis of 6-methyl uracil in greater than 90% yield. The general procedure outlined in FIG. 26 can be used to convert the 6-methyl uracil to the isomer (36b) analogous to Compound (36a), and similarly to compounds (37a) and (37b) containing reactive groups RG. Compounds (36a) and (37b) are embodiments of compounds of the general formula RP—X-LK—Y-RG wherein the nucleobase is a component of the linker (LK) and the N-methyl piperazine is a component of the reporter (RP).

FIGS. 27B and 27C identify commercially available isotopically substituted starting materials (Cambridge Isotope Labs, Andover Mass.) that can be used to produce isotopically enriched versions of 6-methyl uracil as illustrated in FIG. 27A. As illustrated, the symbol "*" next to a carbon atom indicates that the carbon is a $^{13}C$ isotope and the symbol "*'" next to a nitrogen atom indicates that the nitrogen is a $^{15}N$ isotope. Thus, by employing known synthetic procedures and isotopically substituted starting materials, a variety of isotopically substituted labeling reagents, and precursors thereto, can be created.

Figure 28A:
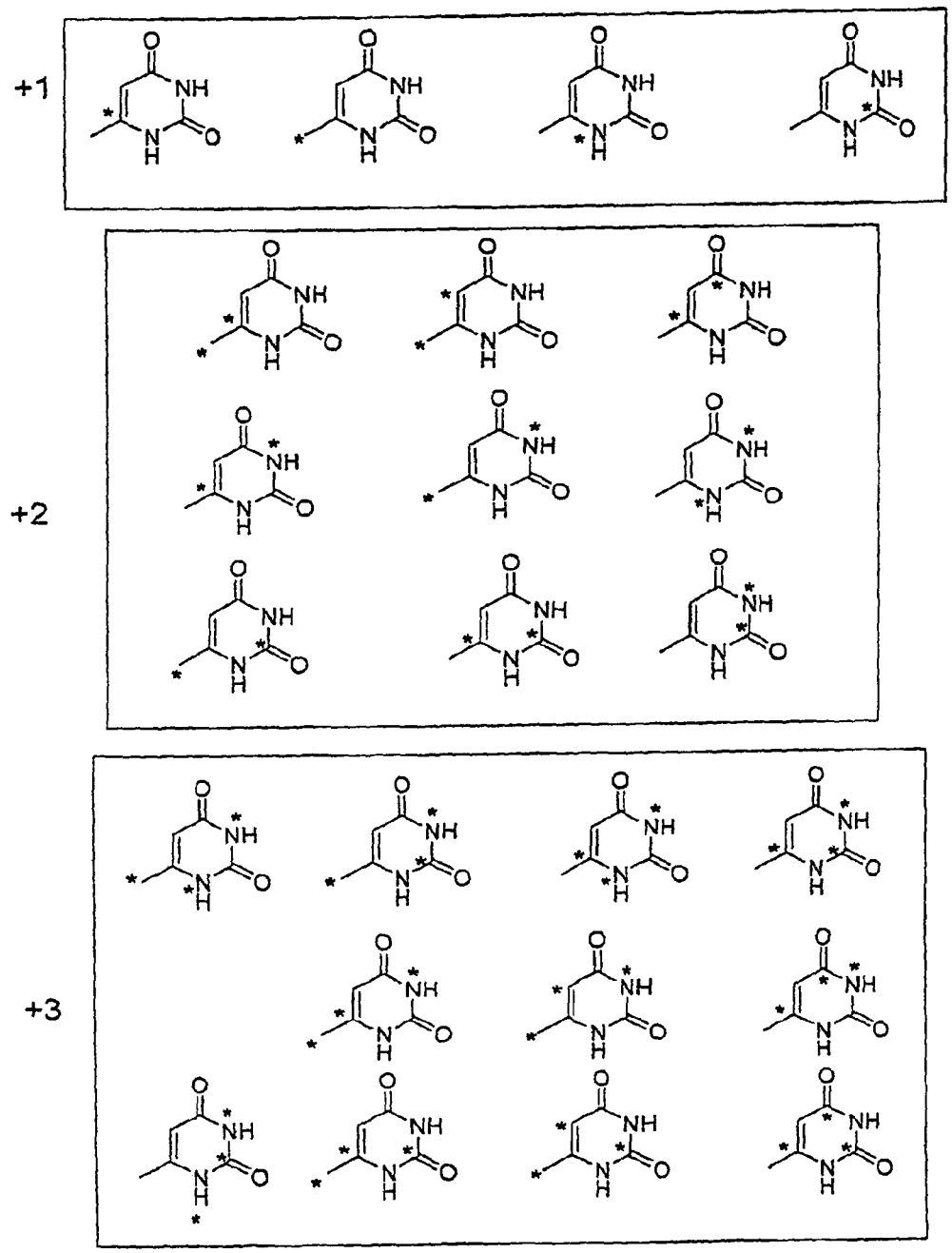
FIGS. 28A and 28B illustrate various isotopically enriched versions of 6-methyl uracil that can be prepared using the compounds illustrated in FIGS. 27B and 27C in combination with the procedure illustrated in FIG. 27A. Atoms labeled with * are heavy atom isotopes.
Figure 28B:
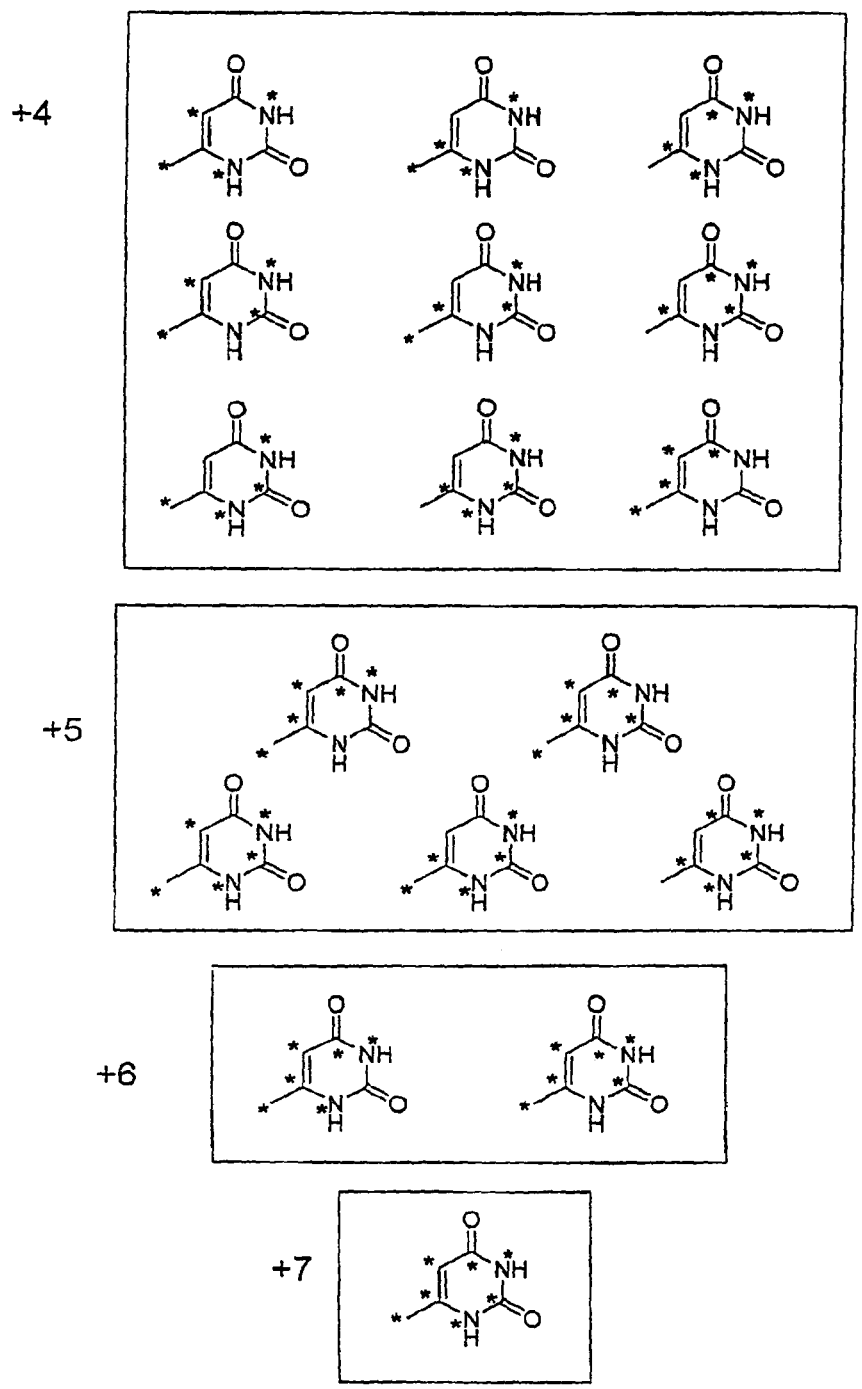
Figure 29A:
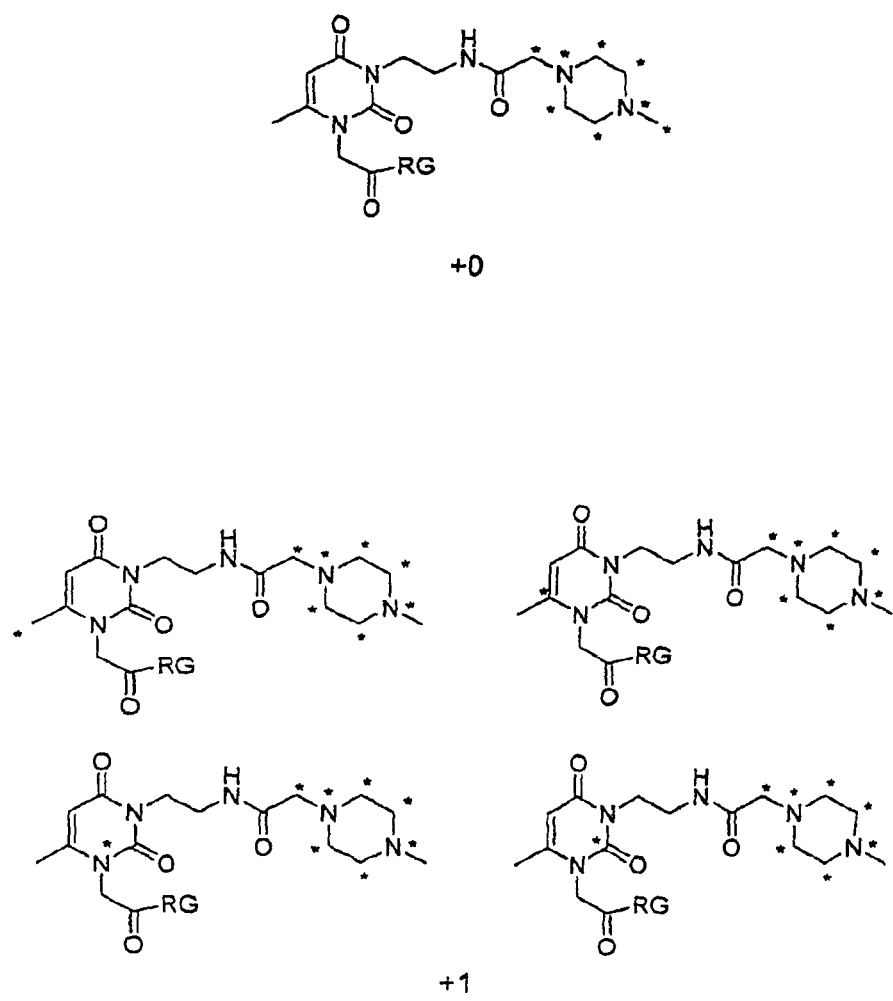
FIGS. 29A-E illustrates various isotopically encoded labeling reagents that can be prepared using the procedures and commercially available compounds illustrated in FIGS. 26, 27A, 27B, 27C, and isotopically substituted 6-methyl uracils illustrated in FIGS. 28A and 28B.
Figure 29B:
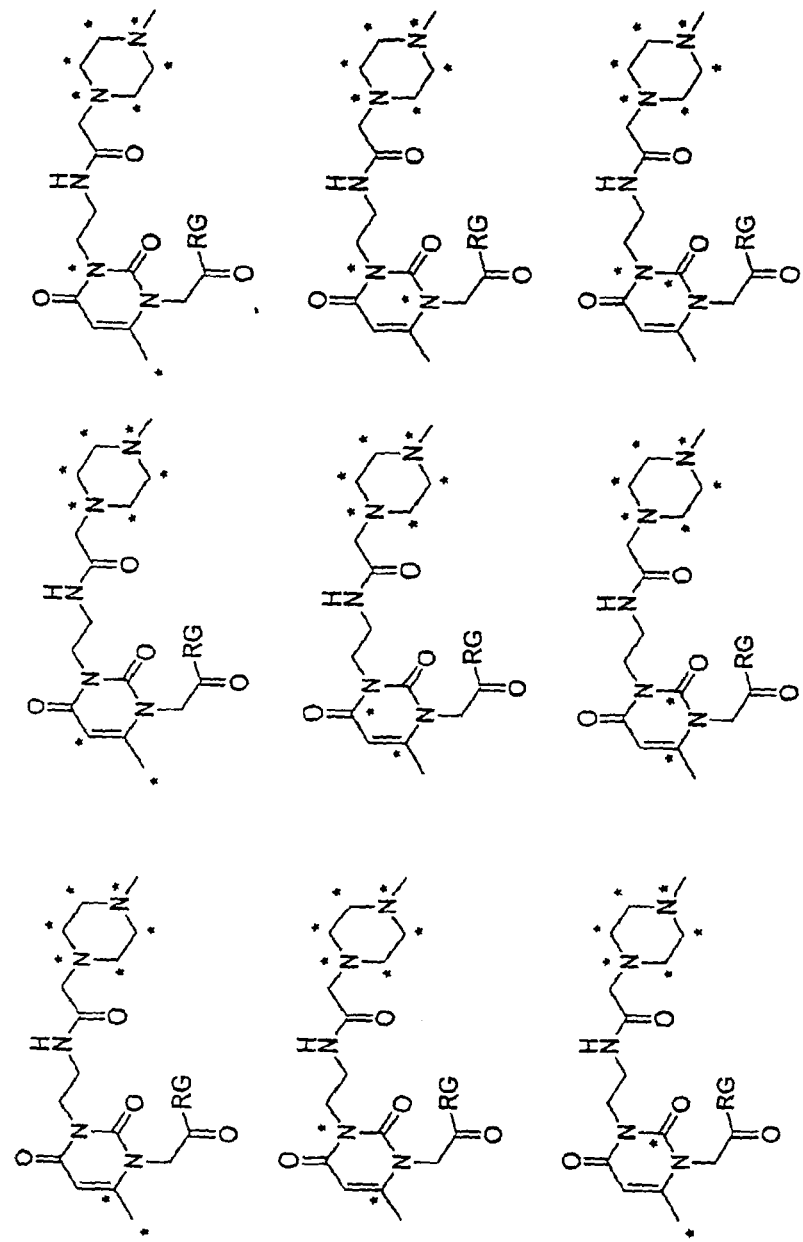
Figure 29C:
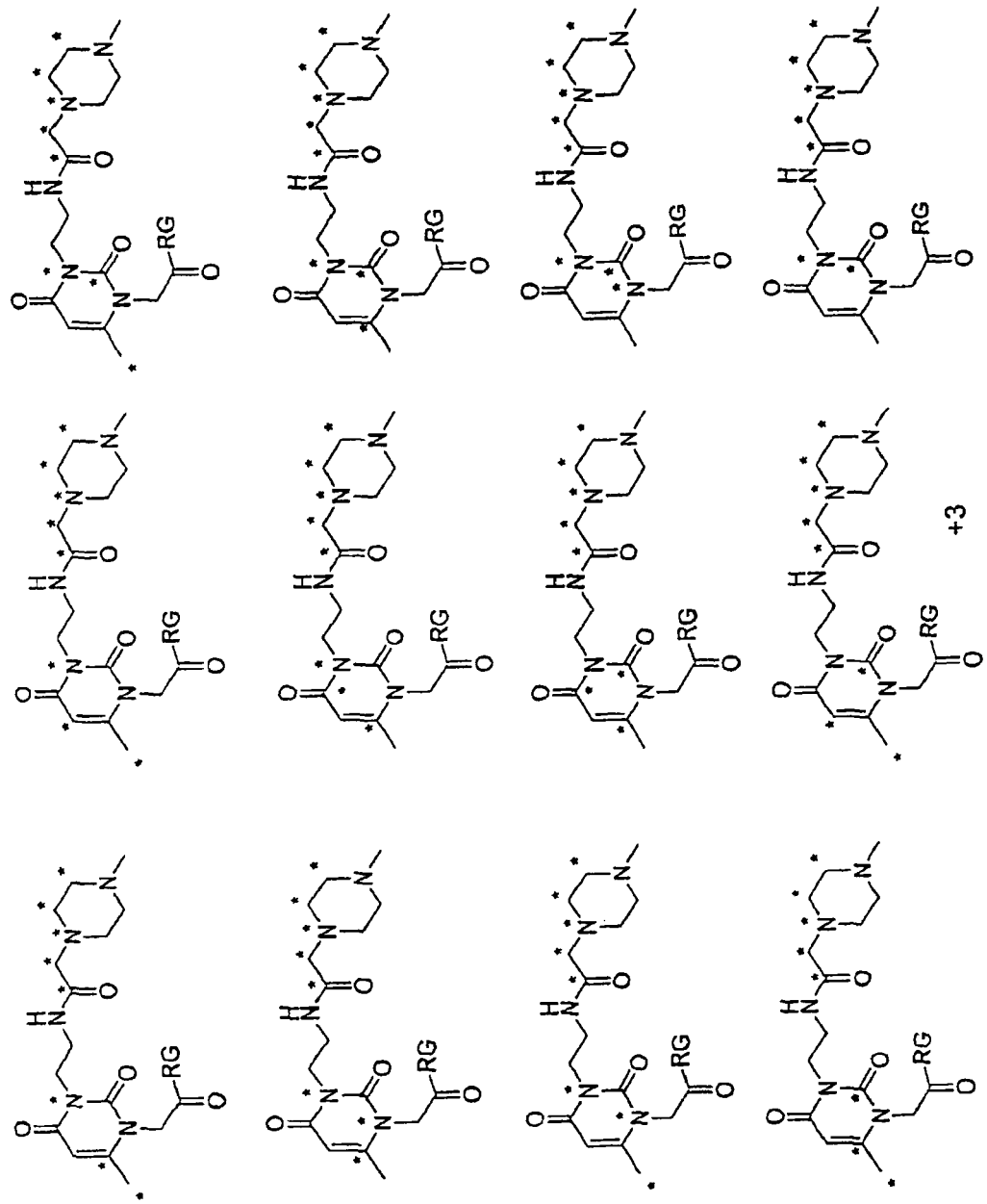
Figure 29D:
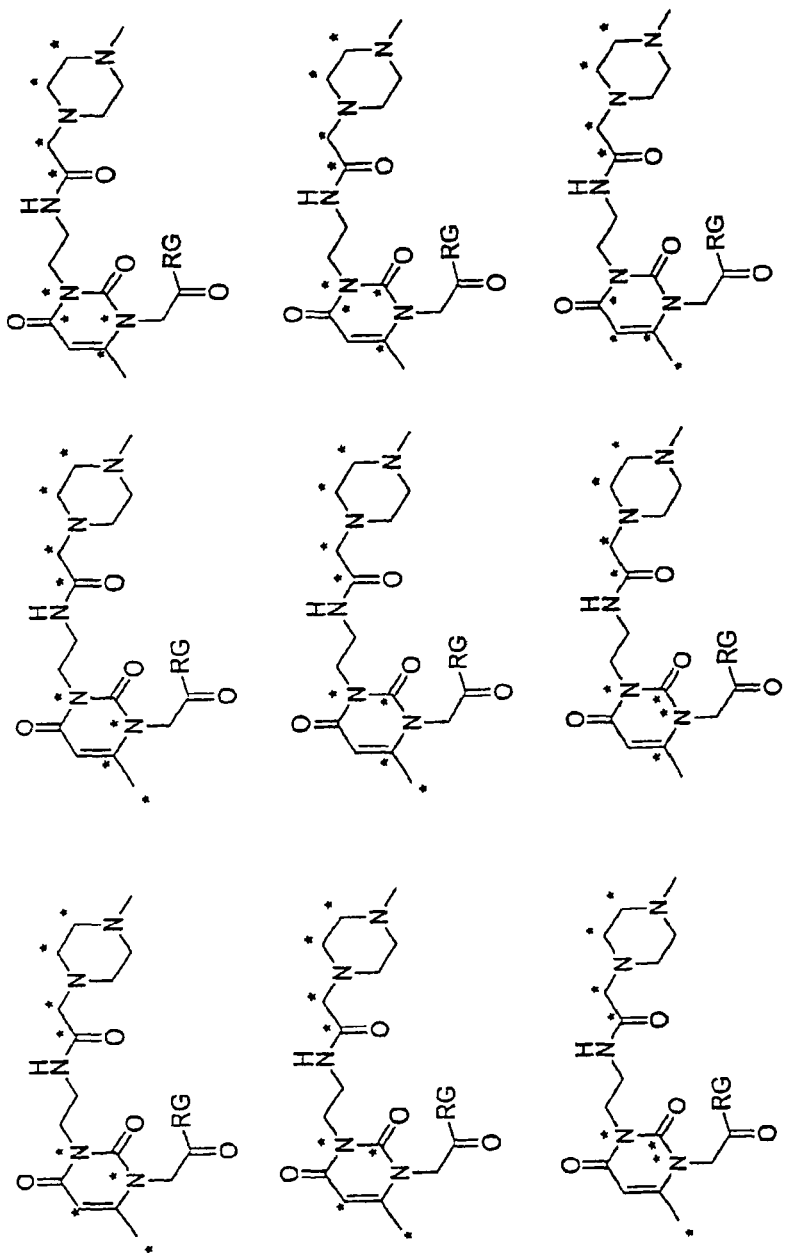
Figure 29E:
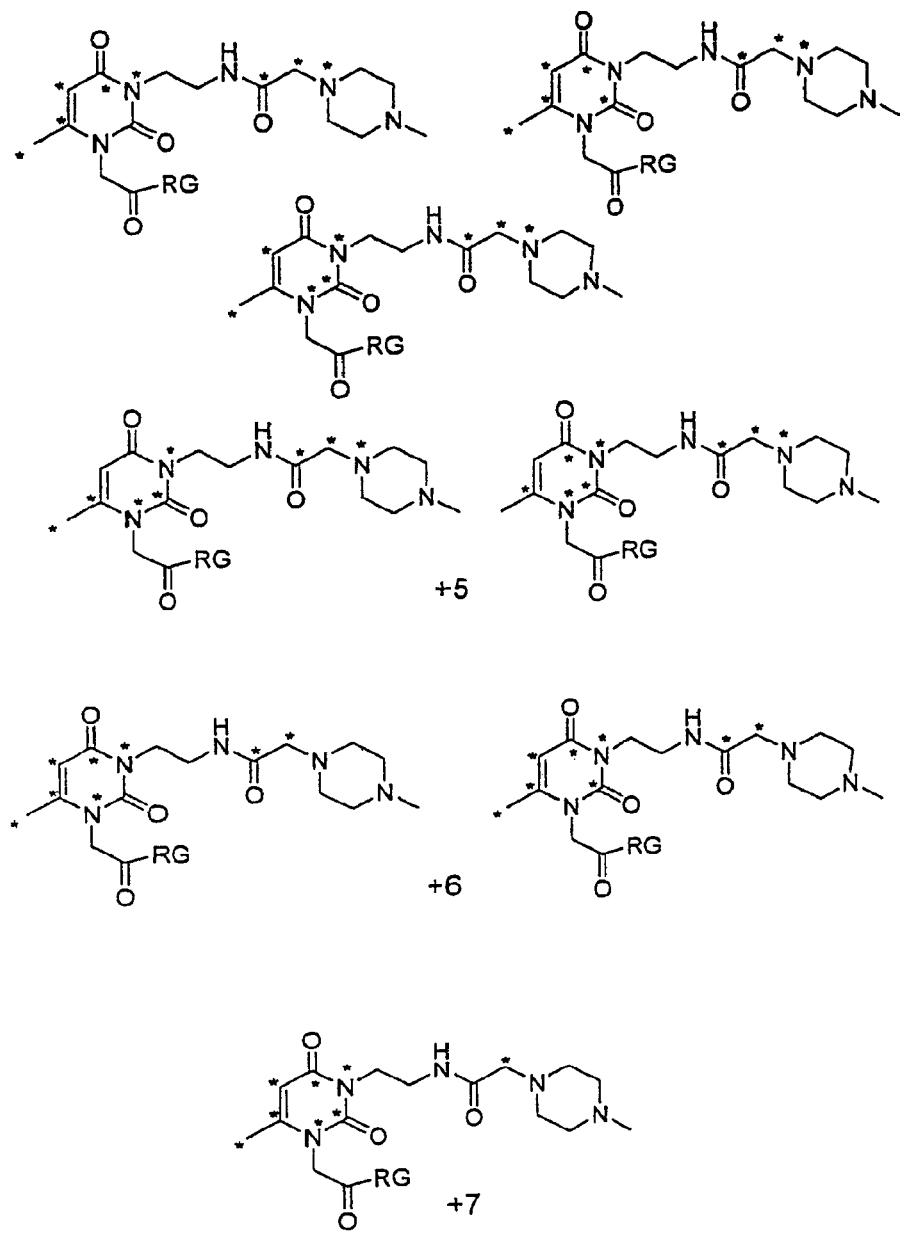

FIGS. 28A-28B illustrate numerous isotopically enriched versions of 6-methyl uracil that can be prepared using these commercially available isotopically substituted starting materials and the procedure illustrated in FIG. 27A. In FIGS. 28A and 28B, the designations +1, +2, +3, +4, +5, +6 and +7, are used to denote versions of 6-methyl uracil comprising 1, 2, 3, 4, 5, 6 and 7 heavy atom isotopes, respectively. Because versions of 6-methyl uracil can be prepared with any where from no heavy atom isotopes to those with up to 7 heavy atom isotopes, it is possible to prepare at least 8 different isobaric labeling reagents of the general formula (37b). Some exemplary isotopically coded labeling reagents are illustrated in FIG. 28C.

Note: 6-methyl uracil can be prepared according to: 1. Donleavy, J. J.; Kise, M. A. 6-Methyl Uracil, *Organic Syntheses*, Coll. Vol. 2, p. 422; Vol. 17, p. 63; 2. Jiang, Z.; Wang, Z.; Ma, D.; Zhou, Y. Improved synthesis of 6-methyluracil. Tongji Daxue Xuebao, Ziran Kexueban, 2003, 31(2), 250-252: 3. 6-Methyluracil. SAIJIYOU SHIGEYA; NISHINAKA TOSHIYOSHI (Yodogawa Pharmaceutical Co., Ltd., Japan). Jpn. Kokai Tokkyo Koho (1981), 2 pp. JP 56139467; Patent written in Japanese. Abstract: Refluxing MeCOCH$_2$CO$_2$Me with urea and p-MeC$_6$H$_4$SO$_3$H in hexane 6 h with azeotropic removal of H$_2$O gave Me$_3$-ureidocrotonate, which was heated with 10% NaOH 0.5 h at 95° to give 92.6% 6-methyluracil.

III. Protocol for One Step Solid-Phase iTRAQ

A. Protein Digestion a. A protein sample (50-100 µg) was dissolved in 50 µl of Denaturing Buffer (0.2 M aqueous NH$_4$HCO$_3$, containing 8 M urea and 20 mM CaCl$_2$).

b. 2 µl of tris[2-carboxyethyl]phosphine (TCEP, Sigma, 50 mM) was added to the sample solution and incubated for 1 hour at 37° C.

c. 1 µl of the methyl methanethiosulfonate (MMTS) reagent (Aldrich, 200 mM) was added and the sample solution was vortexed for 10 minutes.

d. The sample solution was diluted with 0.1 M NH$_4$HCO$_3$ (1:1, 50 µl).

e. 2 µl of LysC (Wako, 1 µg/µl) was added to the sample solution and the sample solution was incubated at 37° C. for 1 hour to digest the protein.

f. The digest solution was diluted with water (1:1, 100 µl).

g. 10 µl (~5 µg) of the Trypsin (Promega V5113, 0.5 µg/µl) was added to the digest solution and the digest solution was incubated at 37° C. for 4-6 hours.

h. 4 µl of the TCEP was added to the digest solution and the digest solution was incubated at 37° C. for 1 hour.

B. Capturing and Tagging Peptides Having Cysteine Amino Acids a. A resin bound isobaric isotopically coded mass tag in the Millipore Cartridge (UFC3OLG 25, as prepared above) was washed with 50 mM Tris buffer (pH 8) (3×300 µl).

b. A protein digestion solution (~200 µl) was transferred into the pre-conditioned cartridge of step a.

c. The cartridge was vortexed at low speed for 30-60 minutes.

d. The cartridge was spun to remove the unbound peptides. The filtrate was analyzed by HPLC (to determine the capturing completion).

e. The resin in the cartridge was washed with 0.1% aqueous TFA solution (3×300 µl).

f. The resin was further dried in a SpeedVac.

C. Release of the Tagged Peptides from the Resin a. 200 µl of a cleavage cocktail of TFA (95%) and TIPS (Aldrich, 5%) was added to the cartridge.

b. The cartridge was allowed to stand at room temperature for 90 minutes.

c. The cartridge was spun down at low speed (6×1000 g) and the filtrate was retained.

d. An additional 100 µl of 0.1% TFA was added to the cartridge and the cartridge was spun down the tube again and the filtrate was retained.

e. The filtrates were pooled and then dry down in the SpeedVac yielding a residue containing the mass tagged peptides.

Analyses of Peptides Labeled with Isobaric Mass Tags Using MS and LC/MS/MS

Mass tags (38) and (39) are a pair of mass tags that were tested extensively. Mass tags (38) and (39) have the following structural formulae:

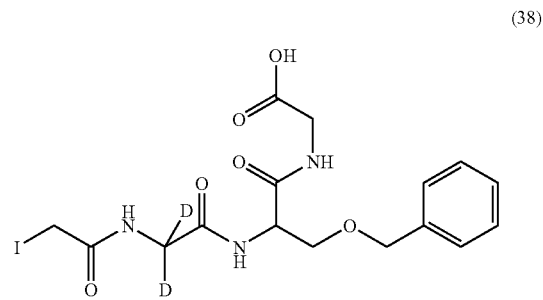

(38)

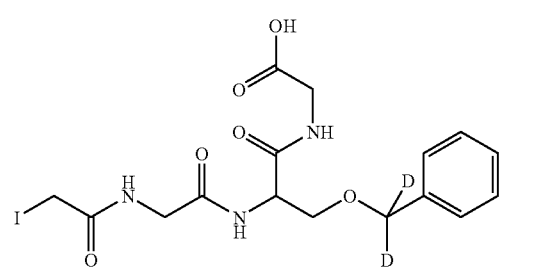

(39)

Mass tags (38) and (39) can be synthesized by employing appropriate isotopically substituted starting materials with any known amino acid syntheses, for example, appropriate isotopically substituted starting materials can be employed with the methods shown in FIG. 25 in combination with a cleavage step to release the mass tags from the solid resin support.

Both mass tags (38) and (39) have a mass of 479.05 Da and are expected to lose a benzyl group when subjected to dissociative energy levels. However, because of the placement of the deuterium substituents on each mass tag, mass tag (38) will have a signature ion having a mass of 91.05 Da and mass tag (39) will have a signature ion of 93.07 Da.

A. QTRAP™ 2000 Analysis of Peptides Alkylated with Mass Tag (38)

The cysteine amino acid residues of synthetic peptides SEQ ID No.: 1 and SEQ ID No.: 2 having the following formulae:

```
SEQ ID No.: 1        IAVAAQNCYK

Figure 2A:
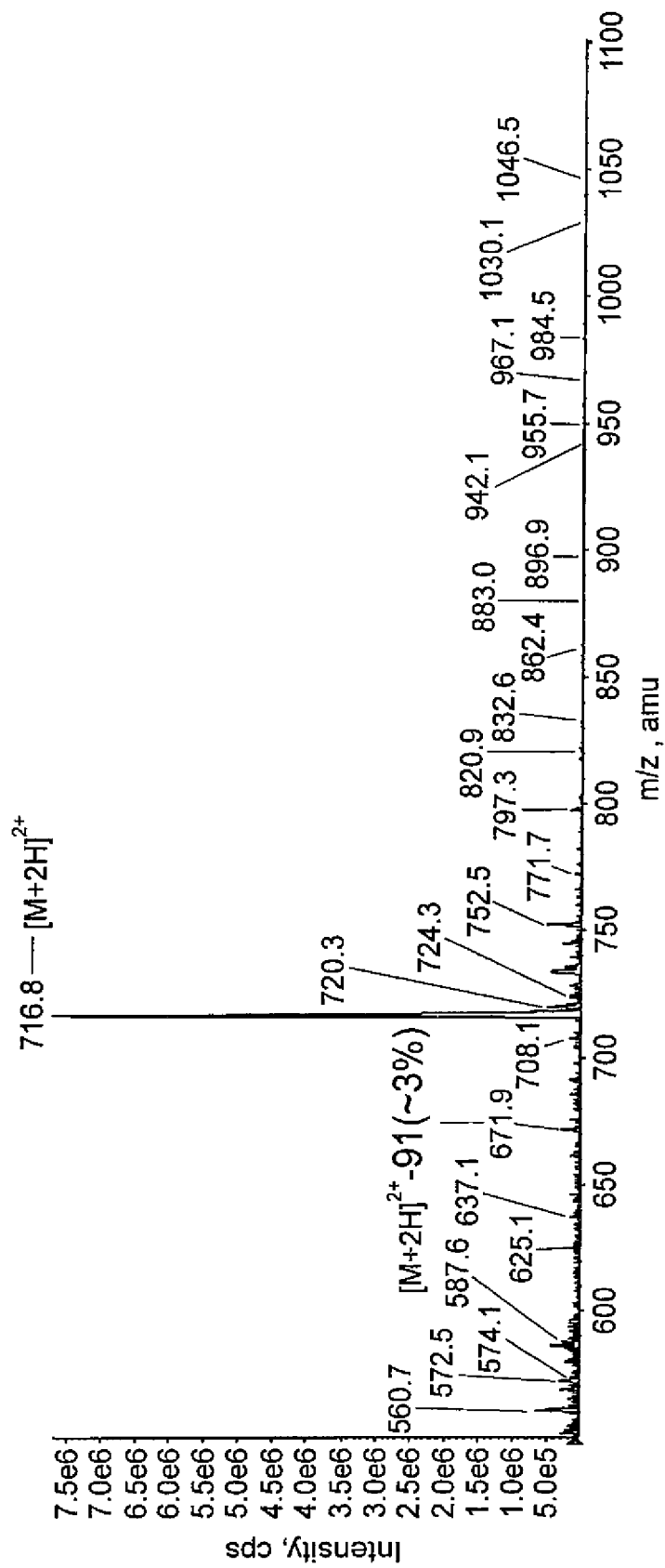
FIG. 2A is a QTRAP™ 2000 MS analysis of SEQ ID No.: 1 which was alkylated with mass tag (32).
Figure 2B:
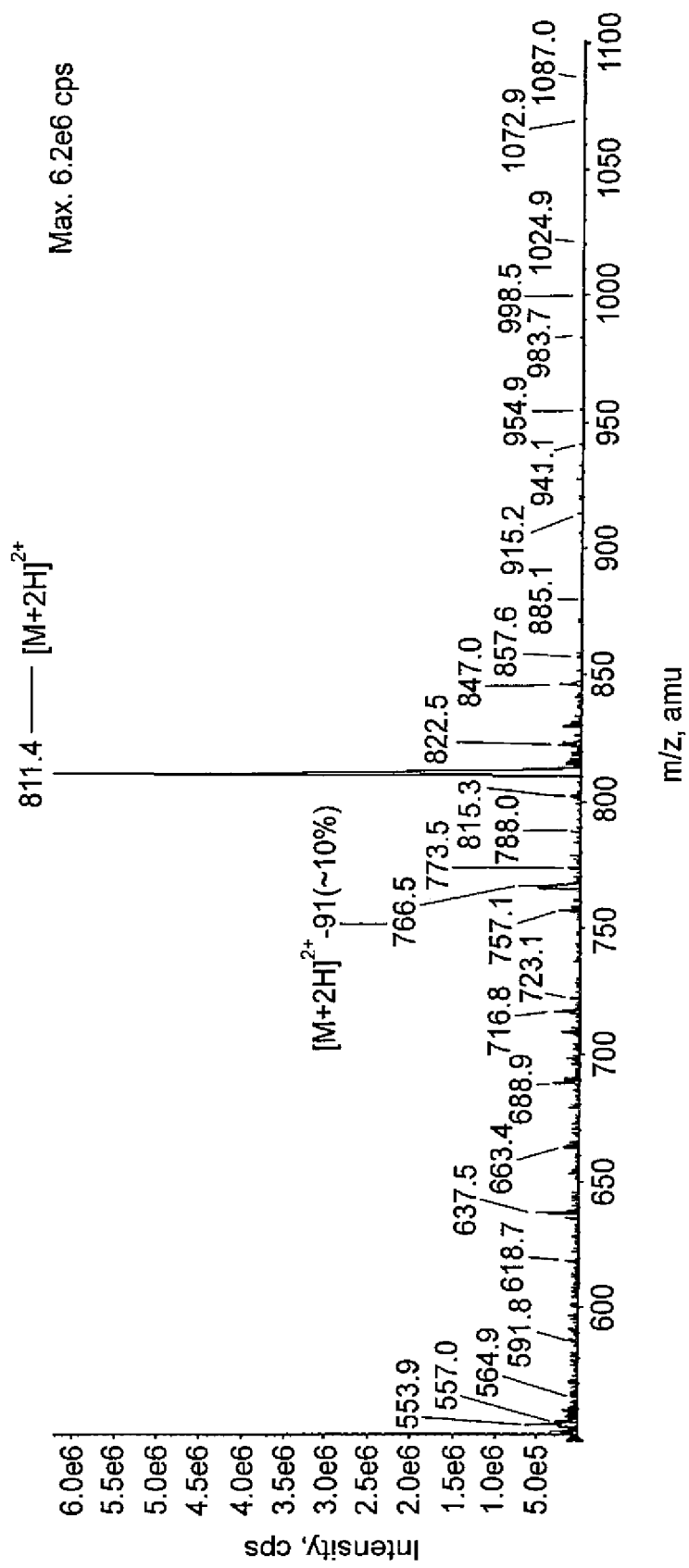
FIG. 2B is a QTRAP™ 2000 MS analysis of SEQ ID No.: 2 which was alkylated with mass tag (32).
Figure 3A:
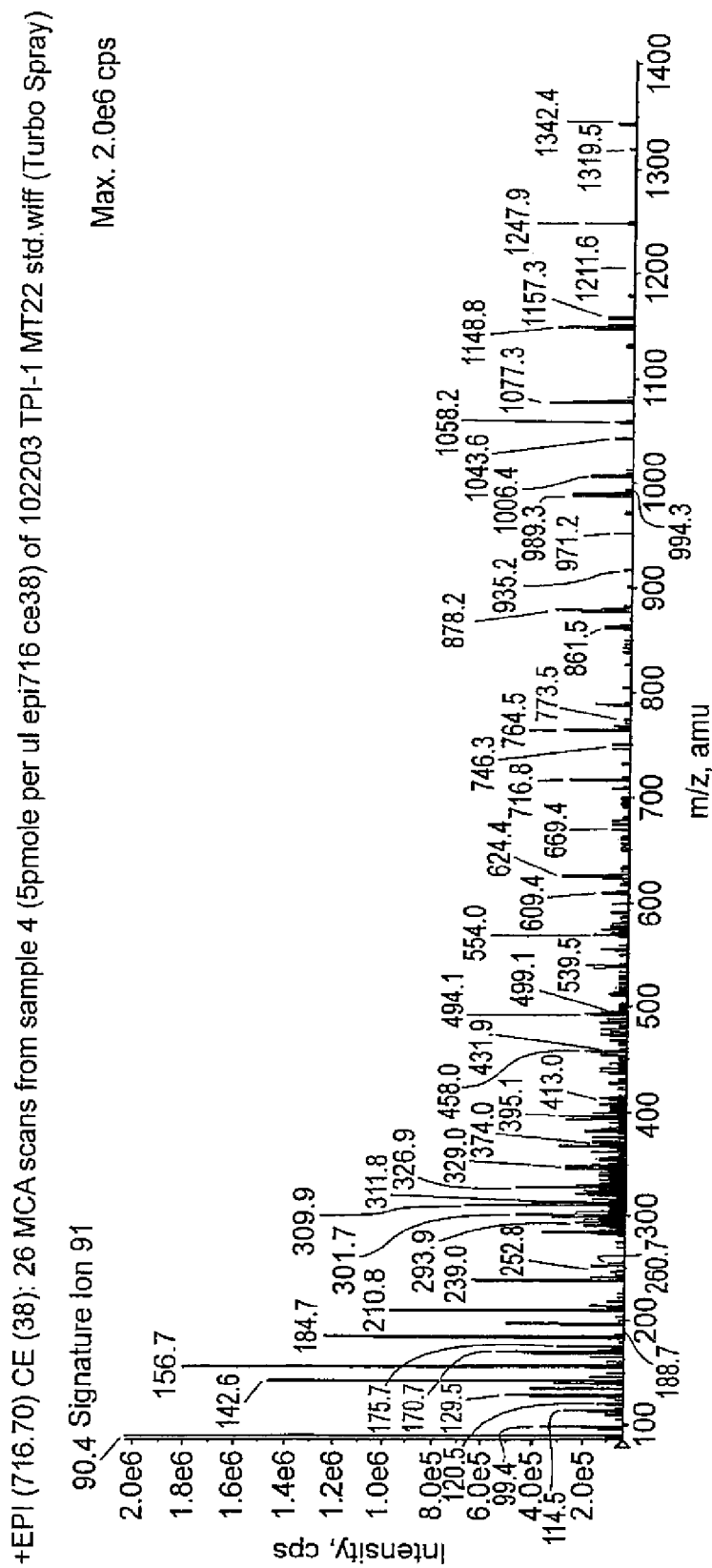
FIG. 3A is a QTRAP™ 2000 MS/MS analysis of SEQ ID No.: 1 which was alkylated with mass tag (32).
Figure 3B:
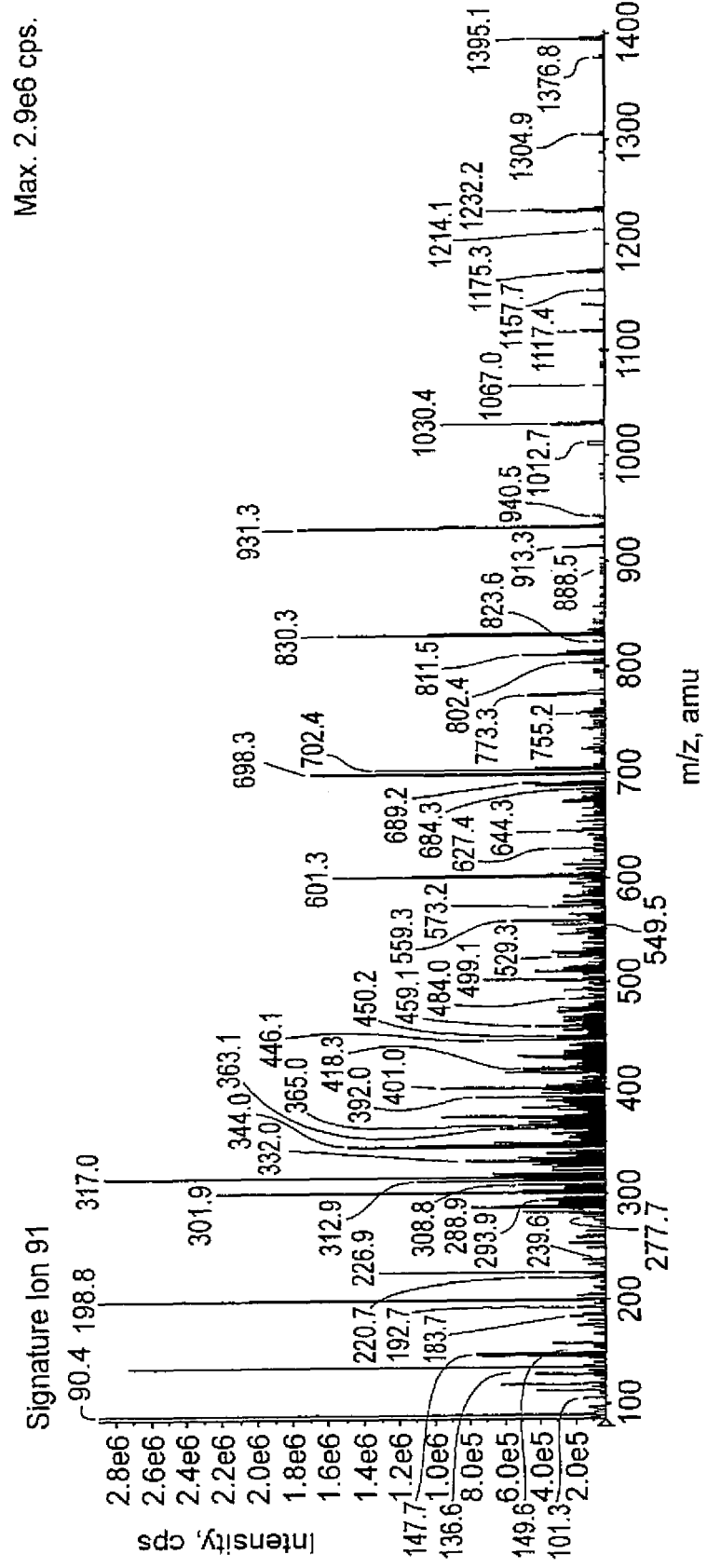
FIG. 3B is a QTRAP™ 2000 MS/MS analysis of SEQ ID No.: 2 which was alkylated with mass tag (32).

SEQ ID No.: 2        IIYGGSVTGATCK
``` were alkylated with a mass tag (38) and were purified by RP-HPLC. The purified tagged-peptides were reconstituted in 0.1% TFA with a concentration at 1 µM. A mass spectra was generated by infusion experiment on the QTRAP™ 2000 System using TurboIonSpray operation. Total 0.5 min (40 scans) were collected. As shown in FIGS. 2A and 2B, there were small percentages of fragmentations (losing 91 Da) of the molecular ions for tagged SEQ ID Nos.: 1 and 2 (approximately 3% and 10%, respectively). In the MS/MS mode in QTRAP™ 2000, tagged SEQ ID Nos.: 1 and 2 generated signature ions of 91 Da (see FIGS. 3A and 3B, respectively). Their intensities were peptide dependent and were typically at least about as intense as those of immonium ions. The sequence ions of the tagged peptides were comparable with those of corresponding peptides alkylated with iodoacetic acid in both presence and intensities.

B. Analysis of Peptides Alkylated with Mass Tag (38) or (39) Using a 4700 Proteomic Analyzer.

SEQ ID No.: 1 and SEQ ID No.: 3 (DCGATWVVLGH-SER) were alkylated with mass tag (38), purified by RP-HPLC, and diluted to 100 μL with 0.1% aqueous TFA. Each sample (1 μL) was mixed with the matrix (1 μL saturated solution), and each mixture (1 μL) was then loaded on a MALDI plate for analysis. The parent ions for tagged SEQ ID No.: 1 and SEQ ID No.: 3 were m/z 1431.7 and 1880.8, respectively. Both peptides were stable, and loss of the signature ion by the parent ion in the MS stage was not observed (see FIGS. 4A and 4B).

Figure 5A:
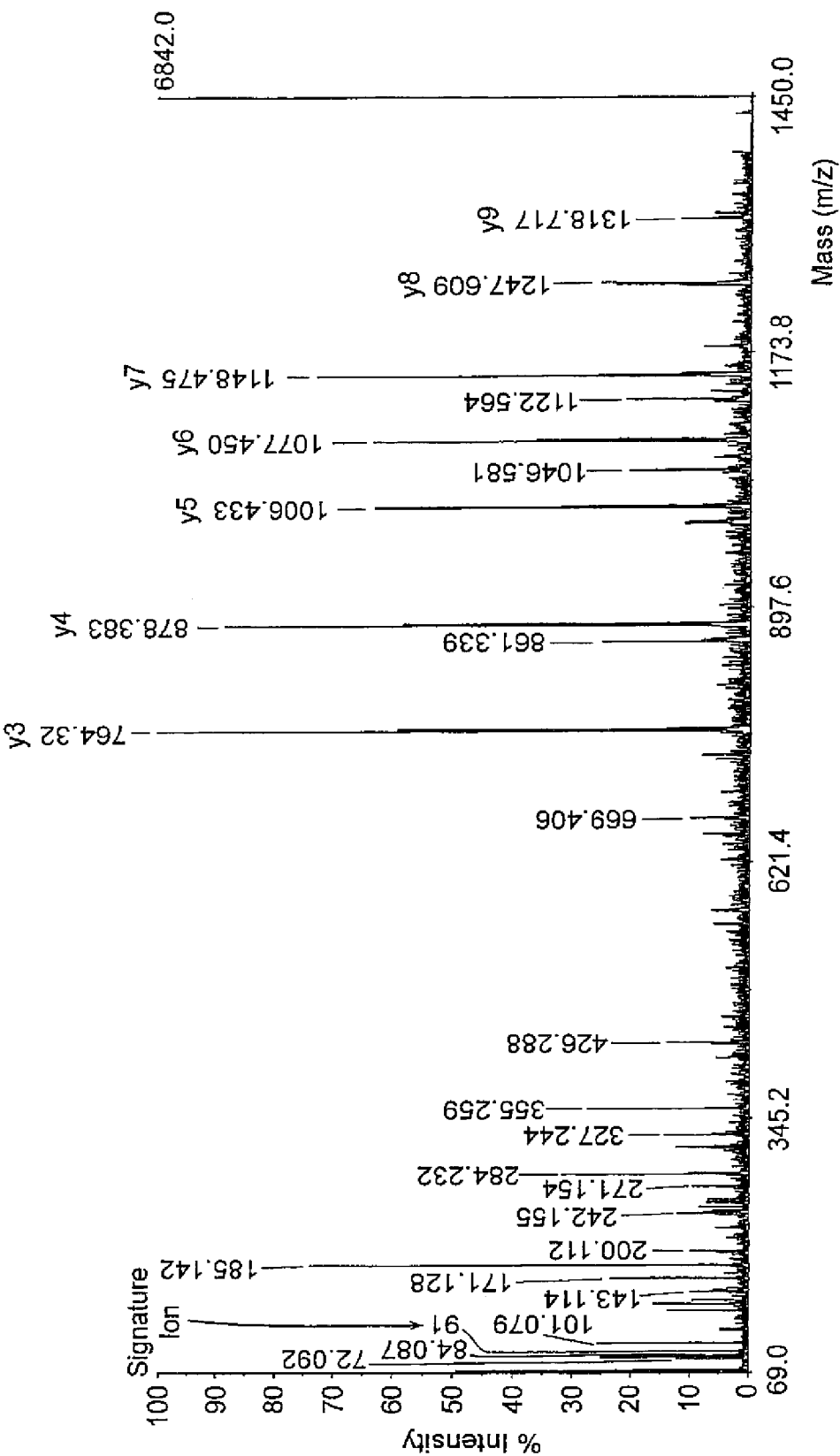
FIG. 5A is a MS/MS analysis of SEQ ID No.: 1, which was alkylated with mass tag (32), using a 4700 Proteomic Analyzer.
Figure 5B:
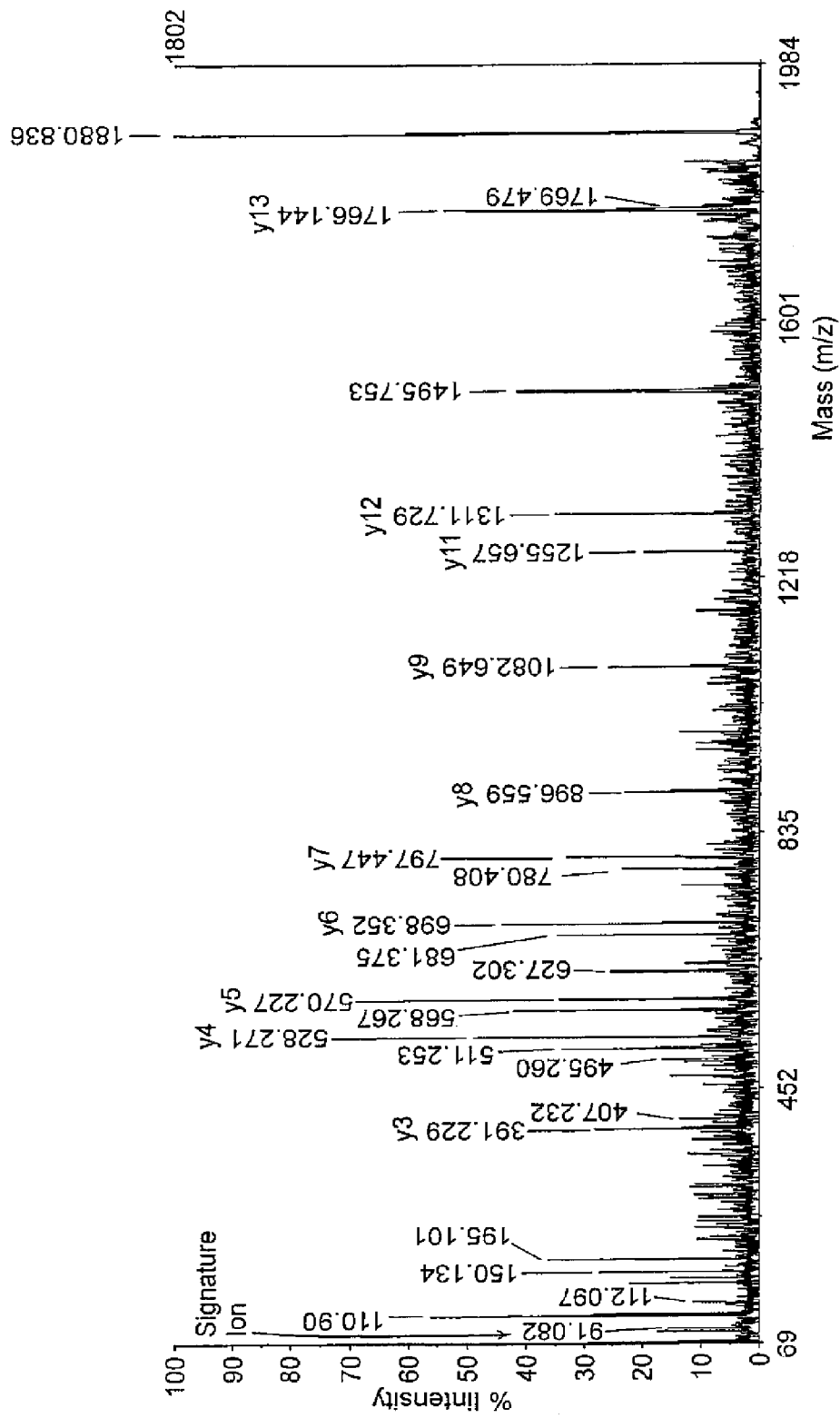
FIG. 5B is a MS/MS analysis of SEQ ID No.: 3, which was alkylated with mass tag (32), using a 4700 Proteomic Analyzer.

The MS/MS spectra for tagged SEQ ID No.: 1 at M/z 1431.7 and tagged SEQ ID No.: 3 at m/z 1880.8 were generated using CID gas pressure set at $1 \times 10^{-3}$ Torr and a total of 2,000 shots were collected (see FIGS. 5A and 5B). The signature ions and the sequence ions are indicated on the figure. The intensities of the signature ions in the MS/MS stage were peptide dependent and were typically less than the intensities obtained using QTRAP™ 2000. However, the intensities could be enhanced significantly when CID was increased (data not shown). The sequence coverage was consistent with that obtained for corresponding peptides alkylated with iodoacetic acid.

C. Quantitation of Peptides Using Mass Tags with QTRAP™ 2000

Figure 6A:
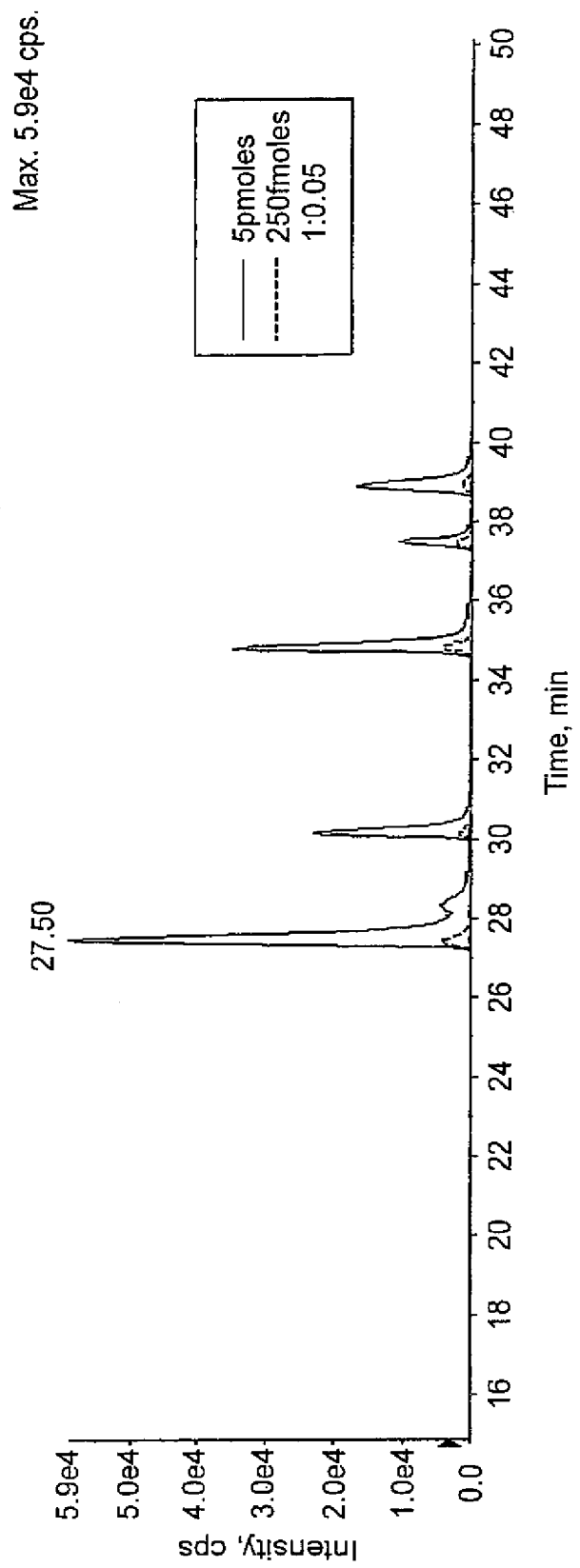
FIG. 6A shows a MRM experiment performed on a QTRAP™ 2000 of two samples, in which one sample has been alkylated with mass tag (32) and the other which has been alkylated with mass tag (33), wherein the ratio of the sample label with mass tag (32) to the sample labeled with mass tag (33) is 1:0.05.
Figure 6B:
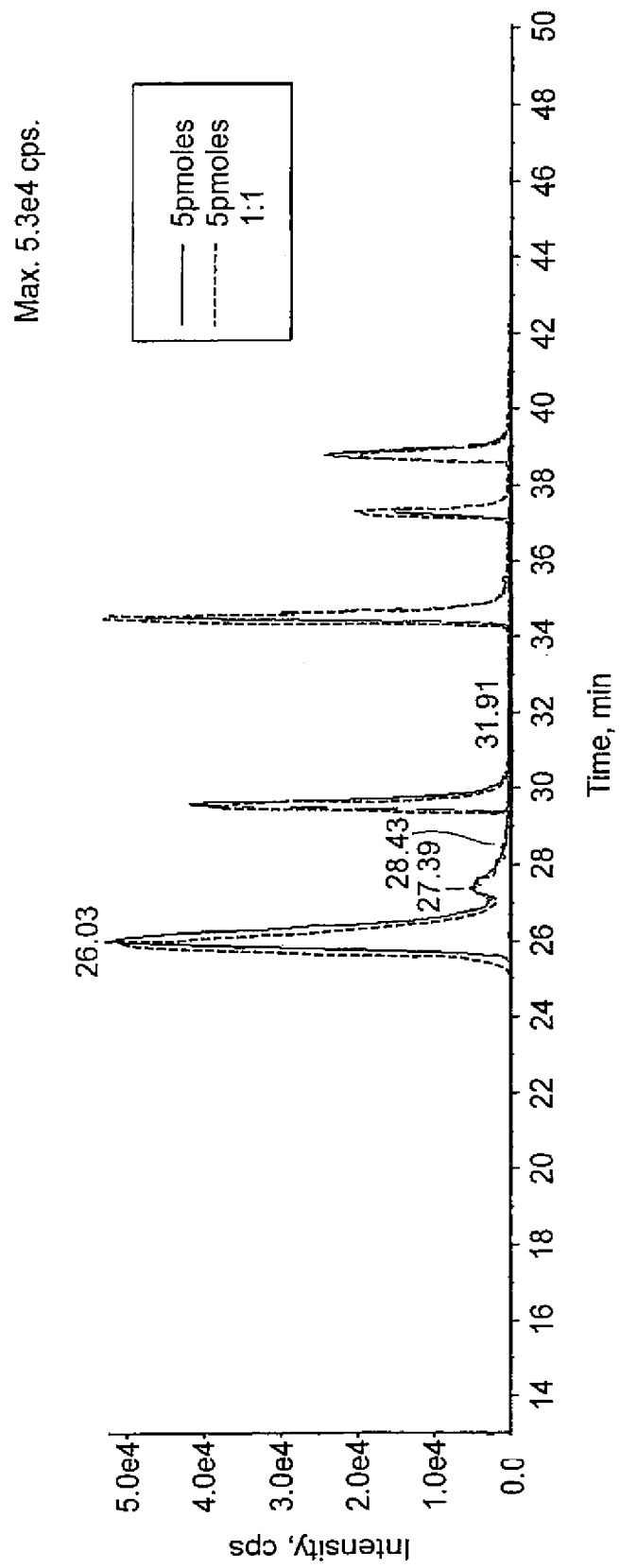
FIG. 6B shows a MRM experiment performed on a QTRAP™ 2000 of two samples, in which one sample has been alkylated with mass tag (32) and the other which has been alkylated with mass tag (33), wherein the ratio of the sample label with mass tag (32) to the sample labeled with mass tag (33) is 1:1.
Figure 6C:
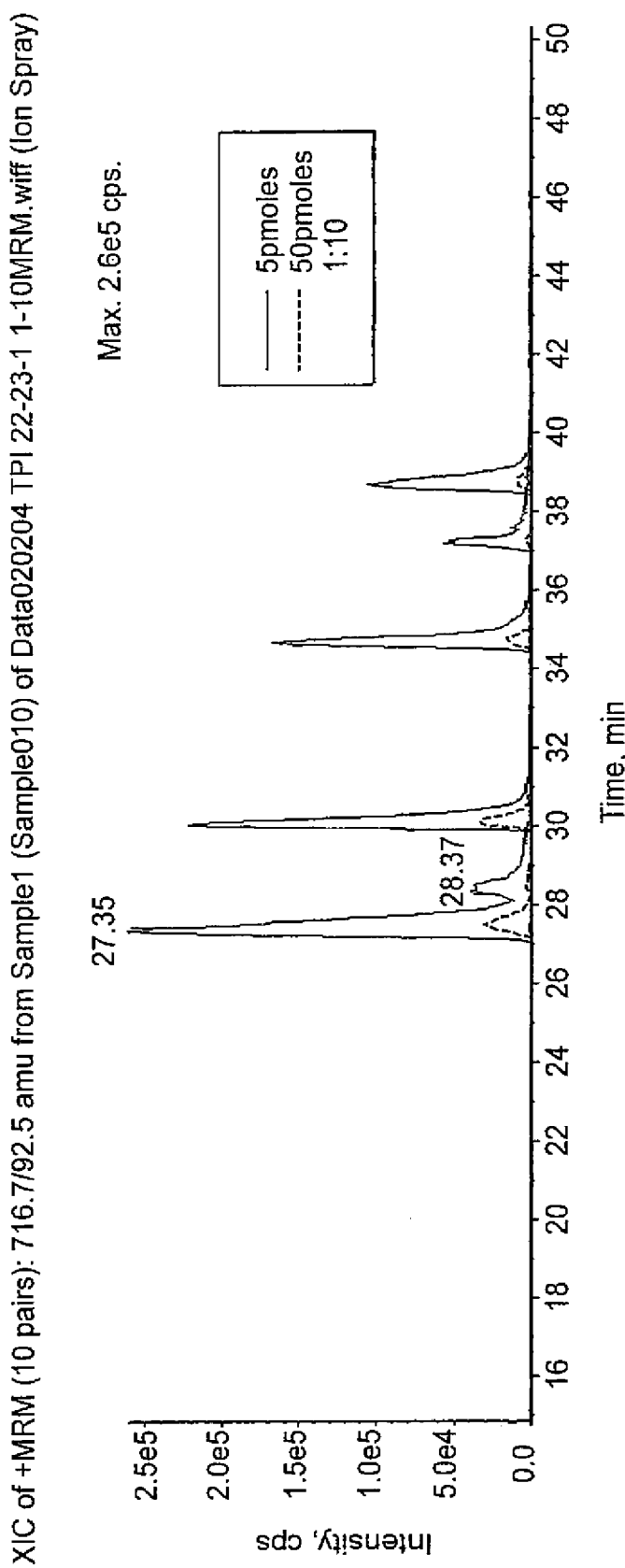
FIG. 6C shows a MRM experiment performed on a QTRAP™ 2000 of two samples, in which one sample has been alkylated with mass tag (32) and the other which has been alkylated with mass tag (33), wherein the ratio of the sample label with mass tag (32) to the sample labeled with mass tag (33) is 1:10.

To evaluate the relative quantifications of protein expressions in a sample, two samples having five peptides were prepared. The HPLC chromatogram for the five peptides is as listed in FIGS. 6A-C. These peptides are named as SEQ ID Nos.: 1-5, based on their retention time from the earliest to the longest

```
SEQ ID No.: 1      IAVAAQNCYK
SEQ ID No.: 2      ITYGGSVTGATCK
SEQ ID No.: 3      DCGATWVVLGHSER
SEQ ID No.: 4      VPADTEVVCAPPTAYIDFAR
SEQ ID No.: 5      VAHALSEGLGVIACIGEK
```

The first sample was reduced, alkylated with mass tag (38), and digested with trysin. The second sample contained the same five peptides as the first sample, but was alkylated with mass tag (39) instead of mass tag (38). The first sample was aliquoted (5 pmoles each), and each aliquote was combined with varied amounts of the second sample from 250 fmoles to 50 pmoles. Each sample mixture was analyzed by LC-MS/MS experiment on QTRAP™ 2000 using the MRM scan mode. Peptides tagged with mass tag (38) generated a signature ion at 91 Da while peptides tagged with mass tag (39) generated a signature ion at 93 Da at MS/MS. In MRM experiments, the specific molecular ion-to-fragment ion transition was measured. As each sample mixture contained 5 cys-peptides which were alkylated with 2 different tags, a total of 10 MRM transition (or pairs) were monitored: 716.5/91 and 716.5/93 for SEQ ID No.: 1; 811.5/91 and 811.5/93 for SEQ ID No.: 2; 628.5/91 and 628.5/93 for SEQ ID No.: 3; 829.9/91 and 829.9/93 for SEQ ID No.: 4 and 707.5/91 and 707.5/93 for SEQ ID No.: 5. The spectra seen in FIG. 6 represented the abundance of the specific fragment ions (i.e., ions of 91 Da and 93 Da) from the corresponding molecular ions (i.e., intact peptide ions) as a function of RPLC-retention time.

As can be seen from Table 1, the expected ratios were consistent with the ratios obtained experimentally. The dynamic range was from 1/0.05 to 1/10, spanning more than 2 orders of magnitude. Since the 91 Da ion from mass tag (38) for the ratio 1/0.1 and the 93 Da ion from mass tag (39) for the ratio 1/10 were still above the background noise, the dynamic range may be to 3 orders of magnitude or more.

D. Quantitation of Peptides Using Mass Tags with 4700 Proteomic Analyzer

A mixture of samples 1 and 2 from section C above was prepared. In the resulting mixture, the concentrations of peptides from sample 1 was fixed at 0.2 μM. Each (1 μL) was then mixed with the matrix (1 μL). Each mixture (1 μL) was then loaded on a MALDI plate, and analyzed on the 4700 Proteomic Analyzer. The CID was set at $9 \times 10^{-6}$ and total 3,000 shots were taken per each MS/MS experiment. The peak area intensities of the 91-ion and the 93-ion were used to calculate the experimental ratios (see Table 1).

The dynamic range was from 1/0.05 to 1/10, spanning more than 2 orders of magnitude. Since the 91 Da ion from mass tag (38) for the ratio 1/0.1 and the 93 Da ion from mass tag (39) for the ratio 1/10 were still above the background noise, the dynamic range may be to 3 orders of magnitude or more.

For relative quantifications, probes with dynamic ranges of 1-order of magnitude may be sufficient since typical relative protein expressions are less than 10-fold. However, for absolute quantifications, probes with a large, dynamic range are desirable. Since the mass tags of the invention have a dynamic range of greater than 2-orders of magnitude, they can be used for absolute quantification, as well as relative quantification of proteins.

TABLE 1

Relative quantification of mass tagged proteins in a sample using QTRAP ™ or 4700 Protein Analyzer.

| Expected Ratio of Signature Ions (91/93) | Ratio of Signature Ions (91/93) from QTRAP ™ | Ratio of Signature Ions (91/93) from 4700 Protein Analyzer |
|---|---|---|
| 1/0.1 | 1/0.094 | 1/0.14 |
| 1/0.2 | 1/0.195 | 1/0.27 |
| 1/0.5 | 1/0.473 | 1/0.60 |
| 1/1 | 1/1.11 | 1/1.16 |
| 1/2 | 1/2.06 | 1/2.3 |
| 1/5 | 1/5.06 | 1/4.85 |
| 1/10 | 1/9.9 | 1/10.1 |

E. Analysis of a Complexed Protein Mixture

Two identical protein mixtures, each containing 19 peptides were alkylated with mass tag (38) or mass tag (39). Thus, the peptides in the mixture alkylated with mass tag (38) will yield a signature ion of 91 Da, while the peptides in the mixture alkylated With mass tag (39) will yield a signature ion of 93 Da. The two protein mixtures were mixed in either a 1:1 ratio or a 1:2 ratio and the mixtures were analyzed by QTRAP™ to determine the ratio of each peptide in each sample based on the ratio of the signature ions (91/93) in the MS/MS stage for each molecular ion. As can be seen from the data in Table 2, the experimental results for the 1:1 mixture and the 1:2 mixture corresponded closely with the expected ratio for each of the nineteen peptides.

| Peptide | Peptide Sequence | (91/93) Ratio 1:1 Mixture | (91/93) Ratio 1:2 Mixture |
|---|---|---|---|
| BSA (aa 223-228) | CASIQK (SEQ ID No.: 6) | 1:1.07 | 1:2.04 |
| BSA (aa 413-420) | QNCDQFEK (SEQ ID No.: 7) | 1:0.89 | 1:1.8 |
| BSA (aa 460-468) | CCTKPESER (SEQ ID No.: 8) | 1:0.86 | 1:2.21 |
| BSA (aa 286-297) | YICDNQDTISSK (SEQ ID No.: 9) | 1:0.73 | 1:1.96 |
| BSA (aa 198-204) | GACLLPK (SEQ ID No.: 10) | 1:1.06 | 1:2.21 |
| BSA (aa 387-399) | DDPHACYSTVFDK (SEQ ID No.: 11) | 1:1.07 | 1:1.44 |
| BSA (aa 139-151) | LKPDPNLCDEFK (SEQ ID No.: 12) | 1:1.16 | 1:2.24 |
| BSA (aa 508-523) | RPCFSALTPDETYVPK (SEQ ID No.: 13) | 1:0.89 | 1:1.97 |
| Transferrin (aa 27-37) | WCAVSEHEATK (SEQ ID No.: 14) | 1:1.0 | 1:1.5 |
| Transferrin (aa 347-362) | EGTCPEAPTDECKPVK (SEQ ID No.: 15) | 1:1.28 | 1:2.44 |
| Transferrin (aa 652-659) | DDTVCLAK (SEQ ID No.: 16) | 1:1.05 | 1:1.7 |
| α-Lacta (aa 128-133) | ALCSEK (SEQ ID No.: 17) | 1:0.75 | 1:1.66 |
| α-Lacta (aa 25-29) | CEVFR (SEQ ID No.: 18) | 1:0.69 | 1:1.88 |
| α-Lacta (aa 134-141) | LDQWLCEK (SEQ ID No.: 19) | 1:0.94 | 1:1.93 |
| α-Lacta (aa 82-98) | DDQNPHSSNICNISCDK (SEQ ID No.: 20) | 1:0.58 | 1:1.16 |
| Lyso (aa 6-13) | CELAAAMK (SEQ ID No.: 21) | 1:1.62 | 1:3.24 |
| β-Lactoglobulin (aa 77-85) | WENGECAQK (SEQ ID No.: 22) | 1:1.3 | 1:1.61 |
|  | AVE (SEQ ID No.: 23) | 1:1.0226 | 1:1.8 |
|  | STDV (SEQ ID No.: 24) | 0.293 | 0.367 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method comprising:
   a) reacting two or more samples, each sample comprising one or more analytes, with a different labeling reagent, the labeling reagents being isotopic and/or isobaric to one another, to thereby produce two or more differently labeled samples each comprising one or more labeled analytes, wherein the labeling reagents are represented by the formula:

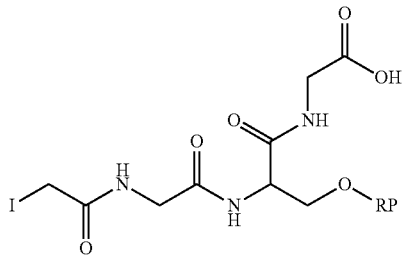

or a salt form and/or hydrate form thereof, wherein independently for each labeling reagent:
   RP is a reporter group represented by either formula:

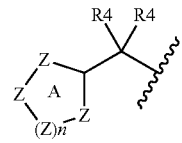

wherein ring A is aromatic; each Z can be independently CH, $CR^2$ or N provided that no more than two Z groups are N; and n can be 1 or 2, or

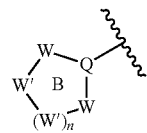

wherein ring B is non-aromatic; n is 1 or 2, each W is independently O, S, or NR$^4$; each W' is independently CH$_2$, CHR$^2$, C(R$^2$)$_2$, C(O), S(O), S(O)$_2$, or C=N—R$^4$; and Q is CH or CR$^2$;

and each R$^2$ is independently hydrogen, deuterium, —OH, halogen, —CN, —NO$_2$, alkyl, alkenyl, alkynyl, aryl, heteroaryl, arylalkyl, heteroarylalkyl, heteroalkyl, heterocycloalkyl, —R$^3$ or -T-R$^3$, each R$^3$ can be independently hydrogen, deuterium, alkyl, alkenyl, alkynyl, aryl, arylalkyl, heteroalkyl, heterocycloalkyl, heteroaryl, or heteroaralkyl; T can be —O—, —NR$^4$, —S—, —C(O)—, —S(O)—, —SO$_2$—, —NR$^4$C(O)—, —C(O)NR$^4$—, —NR$^4$SO$_2$—, —SO$_2$NR$^4$—, —C(O)O—, —OC(O)—, —NR$^4$C(O)O—, or —OC(O)NR$^4$—; and each R$^4$ is independently hydrogen, deuterium, alkyl, heteroalkyl, aryl, or aralkyl; and RP has a unique gross mass for each labeled analyte, and the remainder of the labeling reagent structure has a unique gross mass for each labeled analyte that compensates for the difference in unique gross mass between the RP for each labeled analyte such that the aggregate gross mass of the labeling reagent for each labeled analyte is the same; and b) producing a mixture by mixing together the two or more differently labeled samples, and optionally one or more calibration standards.

2. The method of claim 1 further comprising:

c) performing a first mass spectrometric analysis on the mixture, or a fraction thereof;

d) treating selected ions, of a selected mass to charge ratio, of the labeled analytes from the first mass spectrometric analysis to dissociative energy levels to thereby form signature ions and ionized daughter fragment ions of at least some of the selected ion; and e) performing a second mass analysis of the selected ions, the signature ions and the daughter fragment ions, or a fraction thereof.

3. The method of claim 2, further comprising:

f) determining the gross mass and relative amount of each signature ion moiety in the second mass analysis and the gross mass of the daughter fragment ions.

4. The method of claim 3, further comprising repeating steps (d) through (f) one or more times on selected ions of the labeled analytes at a different selected mass to charge ratio.

5. The method of claim 3, further comprising repeating steps (a) through (f) one or more times, each time with a different fraction of the mixture.

6. The method of claim 1, wherein the two or more samples are the products of an enzymatic digestion reaction.

7. The method of claim 1, wherein each sample is a fraction from a separations process.

8. The method of claim 1, wherein the one or more analytes are proteins, nucleic acid molecules, carbohydrates, lipids, steroids, amino acids, or small molecules of less than 1500 daltons.

9. The method of claim 1, wherein the one or more analytes are peptides.

10. The method of claim 2, wherein the reporter group does not substantially sub-fragment under conditions used to determine the analyte.

11. The method of claim 2, wherein the reporter group does sub-fragment under conditions used to determine the analyte.

12. The method of claim 1, wherein the one or more differentially labeled analytes each comprise a unique reporter group that identifies the sample from which it originated.

13. The method of claim 2, wherein the identity of the labeled analyte associated with the selected ions of a selected mass to charge ratio is determined by analysis of the daughter fragment ions.

14. The method of claim 2, wherein the relative amount of each signature ion in the second mass analysis is determined with respect to the other signature ions.

15. The method of claim 14, wherein the relative amount of each signature ion associated with the identified analyte is correlated with the amount of each sample added to form the mixture to thereby determine the relative amount of the analyte in each of the two or more of the samples combined to form the mixture.

16. The method of claim 15, wherein:

(i) the mixture further comprises a known amount of at least one calibration standard for the identified analyte and the absolute amount of each signature ion is determined with reference to the amount of signature ion associated with the calibration standard; and (ii) the absolute amount of the identified analyte in each different sample of the mixture is determined with reference to the amount of each signature ion.

17. The method of claim 15, further comprising repeating steps (d) through (f), on selected ions of the labeled analytes at a different selected mass to charge ratio, one or more times to thereby identify and/or determine the relative amount of one or more other analytes in each of the two or more of the samples combined to form the mixture.

18. The method of claim 15, further comprising repeating steps (d) through (f), on selected ions of the labeled analytes at a different selected mass to charge ratio, one or more times to thereby identify and/or determine the absolute amount of one of more other analytes in each of the two or more of the samples combined to form the mixture.

* * * * *

```
                    SEQUENCE LISTING

<160> NUMBER OF SEQ ID NOS: 25

<210> SEQ ID NO 1
<211> LENGTH: 10
<212> TYPE: PRT
<213> ORGANISM: Artificial Sequence
<220> FEATURE:
<223> OTHER INFORMATION: Synthetic Probe Sequence

<400> SEQUENCE: 1

Ile Ala Val Ala Ala Gln Asn Cys Tyr Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Probe Sequence

<400> SEQUENCE: 2

Ile Ile Tyr Gly Gly Ser Val Thr Gly Ala Thr Cys Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Probe Sequence
```

-continued

```
<400> SEQUENCE: 3

Asp Cys Gly Ala Thr Trp Val Val Leu Gly His Ser Glu Arg
1               5                   10

<210> SEQ ID NO 4
<211> LENGTH: 20
<212> TYPE: PRT
<213> ORGANISM: Artificial Sequence
<220> FEATURE:
<223> OTHER INFORMATION: Synthetic Probe Sequence

<400> SEQUENCE: 4

Val Pro Ala Asp Thr Glu Val Val Cys Ala Pro Pro Thr Ala Tyr Ile
1               5                   10                  15

Asp Phe Ala Arg
            20

<210> SEQ ID NO 5
<211> LENGTH: 18
<212> TYPE: PRT
<213> ORGANISM: Artificial Sequence
<220> FEATURE:
<223> OTHER INFORMATION: Synthetic Probe Sequence

<400> SEQUENCE: 5

Val Ala His Ala Leu Ser Glu Gly Leu Gly Val Ile Ala Cys Ile Gly
1               5                   10                  15

Glu Lys

<210> SEQ ID NO 6
<211> LENGTH: 6
<212> TYPE: PRT
<213> ORGANISM: Artificial Sequence
<220> FEATURE:
<223> OTHER INFORMATION: BSA (amino acids 223-228)

<400> SEQUENCE: 6

Cys Ala Ser Ile Gln Lys
1               5

<210> SEQ ID NO 7
<211> LENGTH: 8
<212> TYPE: PRT
<213> ORGANISM: Artificial Sequence
<220> FEATURE:
<223> OTHER INFORMATION: BSA (amino acids 413-420)

<400> SEQUENCE: 7

Gln Asn Cys Asp Gln Phe Glu Lys
1               5

<210> SEQ ID NO 8
<211> LENGTH: 9
<212> TYPE: PRT
<213> ORGANISM: Artificial Sequence
<220> FEATURE:
<223> OTHER INFORMATION: BSA (amino acids 460-468)

<400> SEQUENCE: 8

Cys Cys Thr Lys Pro Glu Ser Glu Arg
1               5

<210> SEQ ID NO 9
<211> LENGTH: 12
<212> TYPE: PRT
<213> ORGANISM: Artificial Sequence
```

```
<220> FEATURE:
<223> OTHER INFORMATION: BSA (amino acids 286-297)

<400> SEQUENCE: 9

Tyr Ile Cys Asp Asn Gln Asp Thr Ile Ser Ser Lys
1               5                   10

<210> SEQ ID NO 10
<211> LENGTH: 7
<212> TYPE: PRT
<213> ORGANISM: Artificial Sequence
<220> FEATURE:
<223> OTHER INFORMATION: BSA (amino acids 198-204)

<400> SEQUENCE: 10

Gly Ala Cys Leu Leu Pro Lys
1               5

<210> SEQ ID NO 11
<211> LENGTH: 13
<212> TYPE: PRT
<213> ORGANISM: Artificial Sequence
<220> FEATURE:
<223> OTHER INFORMATION: BSA (amino acids 387-399)

<400> SEQUENCE: 11

Asp Asp Pro His Ala Cys Tyr Ser Thr Val Phe Asp Lys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: BSA (amino acids 139-151)

<400> SEQUENCE: 12

Leu Lys Pro Asp Pro Asn Leu Cys Asp Glu Phe Lys
1               5                   10

<210> SEQ ID NO 13
<211> LENGTH: 16
<212> TYPE: PRT
<213> ORGANISM: Artificial Sequence
<220> FEATURE:
<223> OTHER INFORMATION: BSA (amino acids 508-523)

<400> SEQUENCE: 13

Arg Pro Cys Phe Ser Ala Leu Thr Pro Asp Glu Thr Tyr Val Pro Lys
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: Transferrine (amino acids 27-37)

<400> SEQUENCE: 14

Trp Cys Ala Val Ser Glu His Glu Ala Thr Lys
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Transferrine (amino acids 347-362)
```

-continued

```
<400> SEQUENCE: 15

Glu Gly Thr Cys Pro Glu Ala Pro Thr Asp Glu Cys Lys Pro Val Lys
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Transferrine (amino acids 652-659)

<400> SEQUENCE: 16

Asp Asp Thr Val Cys Leu Ala Lys
1               5

<210> SEQ ID NO 17
<211> LENGTH: 6
<212> TYPE: PRT
<213> ORGANISM: Artificial Sequence
<220> FEATURE:
<223> OTHER INFORMATION: alpha-Lacta (amino acids 128-133)

<400> SEQUENCE: 17

Ala Leu Cys Ser Glu Lys
1               5

<210> SEQ ID NO 18
<211> LENGTH: 5
<212> TYPE: PRT
<213> ORGANISM: Artificial Sequence
<220> FEATURE:
<223> OTHER INFORMATION: alpha-Lacta (amino acids 25-29)

<400> SEQUENCE: 18

Cys Glu Val Phe Arg
1               5

<210> SEQ ID NO 19
<211> LENGTH: 8
<212> TYPE: PRT
<213> ORGANISM: Artificial Sequence
<220> FEATURE:
<223> OTHER INFORMATION: alpha-Lacta (amino acids 134-141)

<400> SEQUENCE: 19

Leu Asp Gln Trp Leu Cys Glu Lys
1               5

<210> SEQ ID NO 20
<211> LENGTH: 17
<212> TYPE: PRT
<213> ORGANISM: Artificial Sequence
<220> FEATURE:
<223> OTHER INFORMATION: alpha-Lacta (amino acids 82-98)

<400> SEQUENCE: 20

Asp Asp Gln Asn Pro His Ser Ser Asn Ile Cys Asn Ile Ser Cys Asp
1               5                   10                  15

Lys

<210> SEQ ID NO 21
<211> LENGTH: 8
<212> TYPE: PRT
<213> ORGANISM: Artificial Sequence
<220> FEATURE:
<223> OTHER INFORMATION: Lyso (amino acids 6-13)
```

```
<400> SEQUENCE: 21

Cys Glu Leu Ala Ala Ala Met Lys
 1               5

<210> SEQ ID NO 22
<211> LENGTH: 9
<212> TYPE: PRT
<213> ORGANISM: Artificial Sequence
<220> FEATURE:
<223> OTHER INFORMATION: Beta-Lactoglobulin (amino acids 77-85)

<400> SEQUENCE: 22

Trp Glu Asn Gly Glu Cys Ala Gln Lys
 1               5

<210> SEQ ID NO 23
<211> LENGTH: 3
<212> TYPE: PRT
<213> ORGANISM: Artificial Sequence
<220> FEATURE:
<223> OTHER INFORMATION: Synthetic probe sequence

<400> SEQUENCE: 23

Ala Val Glu
 1

<210> SEQ ID NO 24
<211> LENGTH: 4
<212> TYPE: PRT
<213> ORGANISM: Artificial Sequence
<220> FEATURE:
<223> OTHER INFORMATION: Synthetic probe sequence

<400> SEQUENCE: 24

Ser Thr Asp Val
 1

<210> SEQ ID NO 25
<211> LENGTH: 13
<212> TYPE: PRT
<213> ORGANISM: Artificial Sequence
<220> FEATURE:
<223> OTHER INFORMATION: [Glu1]-Fibrinopeptide B human

<400> SEQUENCE: 25

Gly Val Asn Asp Asn Glu Glu Gly Phe Phe Ser Ala Arg
 1               5                   10
```